United States Patent
Mizrahi

(10) Patent No.: US 10,961,559 B2
(45) Date of Patent: Mar. 30, 2021

(54) REGULATION OF FEED EFFICIENCY AND METHANE PRODUCTION IN RUMINATING ANIMALS

(71) Applicant: The State of Israel, Ministry of Agriculture & Rural Development, Agricultural Research Organization (ARO) (Volcani Center), Rishon-LeZion (IL)

(72) Inventor: Itzhak Mizrahi, Tel-Aviv (IL)

(73) Assignee: The State of Israel Ministry of Agriculture & Rural Development, Agricultural Research Organization (ARO) (Volcani Center), Rishon-LeZion (IL)

(*) Notice: Subject to any disclaimer, the term of this patent is extended or adjusted under 35 U.S.C. 154(b) by 0 days.

(21) Appl. No.: 16/096,349

(22) PCT Filed: Nov. 3, 2016

(86) PCT No.: PCT/IL2016/051197
§ 371 (c)(1),
(2) Date: Oct. 25, 2018

(87) PCT Pub. No.: WO2017/187433
PCT Pub. Date: Nov. 2, 2017

(65) Prior Publication Data
US 2020/0123588 A1    Apr. 23, 2020

Related U.S. Application Data

(60) Provisional application No. 62/327,616, filed on Apr. 26, 2016.

(51) Int. Cl.
| | | |
|---|---|---|
| *C12Q 1/06* | (2006.01) | |
| *A23K 50/10* | (2016.01) | |
| *A23K 50/60* | (2016.01) | |
| *A23K 10/18* | (2016.01) | |
| *A61K 9/00* | (2006.01) | |
| *A61K 35/741* | (2015.01) | |
| *A61K 35/744* | (2015.01) | |
| *A61K 45/06* | (2006.01) | |
| *C12Q 1/689* | (2018.01) | |
| *A61K 35/00* | (2006.01) | |

(52) U.S. Cl.
CPC .............. *C12Q 1/06* (2013.01); *A23K 10/18* (2016.05); *A23K 50/10* (2016.05); *A23K 50/60* (2016.05); *A61K 9/0031* (2013.01); *A61K 9/0056* (2013.01); *A61K 35/741* (2013.01); *A61K 35/744* (2013.01); *A61K 45/06* (2013.01); *C12Q 1/689* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 7,291,328 B2 | 11/2007 | Garner et al. | |
| 8,771,723 B2* | 7/2014 | Perdok | A23K 20/20 |
| | | | 424/438 |
| 2014/0099406 A1* | 4/2014 | Hoffmann Pegoraro | |
| | | | A61K 33/06 |
| | | | 426/69 |
| 2014/0199281 A1 | 7/2014 | Henn et al. | |
| 2016/0015757 A1 | 1/2016 | Mizrahi et al. | |

FOREIGN PATENT DOCUMENTS

| | | |
|---|---|---|
| EP | 0299183 | 1/1989 |
| WO | WO 2014/141274 | 9/2014 |
| WO | WO 2017/187433 | 11/2017 |

OTHER PUBLICATIONS

International Preliminary Report on Patentability dated Nov. 8, 2018 From the International Bureau of WIPO Re. Application No. PCT/IL2016/051197. (9 Pages).
International Preliminary Report on Patentability dated Sep. 24, 2015 From the International Bureau of WIPO Re. Application No. PCT/IL2014/050277.
International Search Report and the Written Opinion dated Jun. 15, 2014 From the International Searching Authority Re. Application No. PCT/IL2014/050277.
International Search Report and the Written Opinion dated Feb. 26, 2017 From the International Searching Authority Re. Application No. PCT/IL2016/051197. (15 Pages).
Invitation to Pay Additional Fees and Communication Relating to the Results of the Partial International Search dated Jan. 23, 2017 From the International Searching Authority Re. Application No. PCT/IL2016/051197. (5 Pages).
Official Action dated Dec. 1, 2017 From the U.S. Appl. No. 14/773,887. (15 pages).
Official Action dated Oct. 15, 2018 From the U.S. Appl. No. 14/773,887. (11 pages).
Restriction Official Action dated May 25, 2017 From the U.S. Appl. No. 14/773,887. (6 pages).

(Continued)

*Primary Examiner* — Heidi Reese

(57) ABSTRACT

A method of determining the feed efficiency and methane production of a ruminating animal comprising analyzing the number and/or diversity of a bacterial taxon of a microbiome of the animal or of a gene content of said microbiome, wherein a number and/or diversity of said taxon below a predetermined level is indicative of an animal having a high feed efficiency and low methane production, or a number of genes below a predetermined level is indicative of an animal having a high feed efficiency and low methane production.

7 Claims, 29 Drawing Sheets
(29 of 29 Drawing Sheet(s) Filed in Color)
Specification includes a Sequence Listing.

(56) References Cited

OTHER PUBLICATIONS

Carberry et al. "Effect of Phenotype Residual Feed Intake and Dietary Forage Content on the Rumen Microbial Community of Beef Cattle", Applied and Environmental Microbiology, 78(14): 4949-4958, Published Online May 4, 2012.
Carberry et al. "Rumen Methanogenic Genotypes Differ in Abundance According to Host Residual Feed Intake Phenotype and Diet Type", Applied and Environmental Microbiology, 80(2): 586-594, Published Online Nov. 8, 2013.
Chiquette et al. "Prevotella Bryantii 25A Used as A Probiotic in Early-Lactation Dairy Cows: Effect on Ruminal Fermentation Characteristics, Milk Production, and Milk Composition", Journal of Dairy Science, 91: 3536-3543, 2008.
Guan et al. "Linkage of Microbial Ecology to Phenotype: Correlation of Rumen Microbial Ecology to Cattle's Feed Efficiency", FEMS Microbiology Letters, 288(1): 85-91, Nov. 2008. p. 89, Left Col., Last Para—p. 90, Right Col., 1st Para.
Hernandez-Sanabria et al. "Correlation of Particular Bacterial PCR-Denaturing Gradient Gel Electrophoresis Patterns With Bovine Ruminal Fermentation Parameters and Feed Efficiency Traits", Applied and Environmental Microbiology, 76(19): 6338-6350, Oct. 2010.
Jami et al. "Composition and Similarity of Bovine Rumen Microbiota Across Individual Animals", PLoS ONE, 7(3): e33306-1-e33306-8, Mar. 2012. Figs.2, 4.
Jami et al. "Potential Role of the Bovine Rumen Microbiome in Modulating Milk Composition and Feed Efficiency", PLoS ONE, 9(1): e85423-1-e85423-6, Jan. 22, 2014.
Jami et al. "Similarity of the Ruminal Bacteria Across Individual Lactating Cows", Anaerobe, 18(3): 338-342, Apr. 21, 2012.
Kittelmann et al. "Two Different Bacterial Community Types Are Linked With the Low-Methane Emission Trait in Sheep", PLoS ONE, 9(7): e103171-1-e103171-9, Published Online Jul. 31, 2014.
Kong et al. "Composition, Spatial Distribution, and Diversity of the Bacterial Communities in the Rumen of Cows Fed Different Forages", FEMS Microbial Ecol 74: 612-622, Nov. 2010.
Krause et al. "Opportunities to Improve Fiber Degradation in the Rumen: Microbiology, Ecology, and Genomics", FEMS Microbiology Reviews, 27: 663-693, 2003.
Li et al. "Effect of Sampling Location and Time, and Host Animal on Assessment of Bacterial Diversity and Fermentation Parameters in the Bovine Rumen", Journal of Applied Microbiology, 107: 1924-1934, 2009.

Seo et al. "Direct-fed Microbials for Ruminant Animals", Asian-Australasian Journal of Animal Sciences, 23(12): 1657-1667, Dec. 2010.
Shabat et al. "Specific Microbiome-Dependent Mechanisms Underlie the Energy Harvest Efficiency of Ruminants", The ISME Journal, 10(12): 2958-2972, Published Online May 6, 2016.
Weimer et al. "Host Specificity of the Ruminal Bacterial Community in the Dairy Cow Following Near-Total Exchange of Ruminal Contents", Journal of Dairy Science, 93(12): 5902-5912, Dec. 2010. Abstract, Figs.5, 6, Discussion Section.
West et al. "Effects of Addition of Bacterial Inoculants to the Diets of Lactating Dairy Cows on Feed Intake, Milk Yield, and Milk Composition", The Professional Animal Scientist, 27: 122-126, 2011.
Zhou et al. "Assessment of the Microbial Ecology of Ruminal Methanogens in Cattle With Different Feed Efficiencies", Applied and Environmental Microbiology, 75(20): 6524-6533, Published Ahead of Print Aug. 28, 2009.
Advisory Action Before the Filing of An Appeal Brief dated Feb. 19, 2019 From the U.S. Appl. No. 14/773,887. (5 pages).
Notification of Necessity to Provide Additional Materials dated Feb. 21, 2020 From the Eurasian Patent Organization, Eurasian Patent Office Re. Application No. 201892404 and Its Translation Into English. (7 Pages).
Examination Report dated Dec. 17, 2019 From the Servico Publico Federal, Ministerio da Economia, Instututo Nacional da Propriedade Industrial do Brasil Re. Application No. BR112018072105-0. (4 Pages).
Translation Dated Jan. 23, 2020 of Examination Report dated Dec. 17, 2019 From the Servico Publico Federal, Ministerio da Economia, Instututo Nacional da Propriedade Industrial do Brasil Re. Application No. BR112018072105-0. (5 Pages).
Final Official Action dated Jun. 12, 2020 from the U.S. Appl. No. 14/773,887. (19 pages).
Singh et al. "Metagenomics in Animal Gastrointestinal Ecosystem: a Microbiological and Biotechnological Perspective", Indian Journal of Microbiology 48: 216-227, Jun. 2008.
Official Action dated Aug. 28, 2019 From the U.S. Appl. No. 14/773,887. (12 pages).
Krehbiel et al. "Bacterial Direct-Fed Microbials in Ruminant Dets: Performance Response and Mode of Action", Journal of Animal Science, 81(14_suppl_2): E120-E132, Feb. 1, 2003.

\* cited by examiner

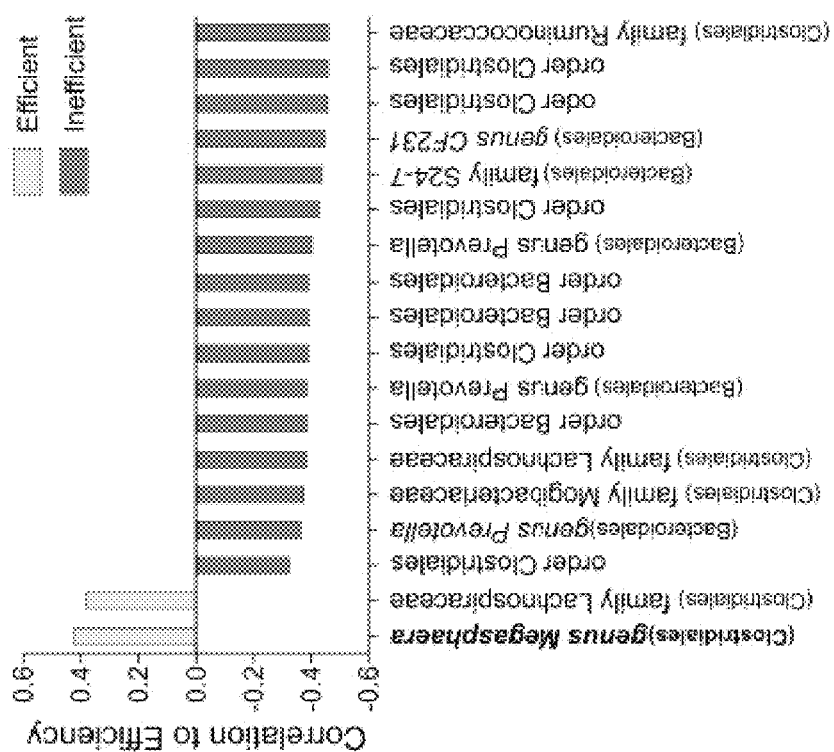

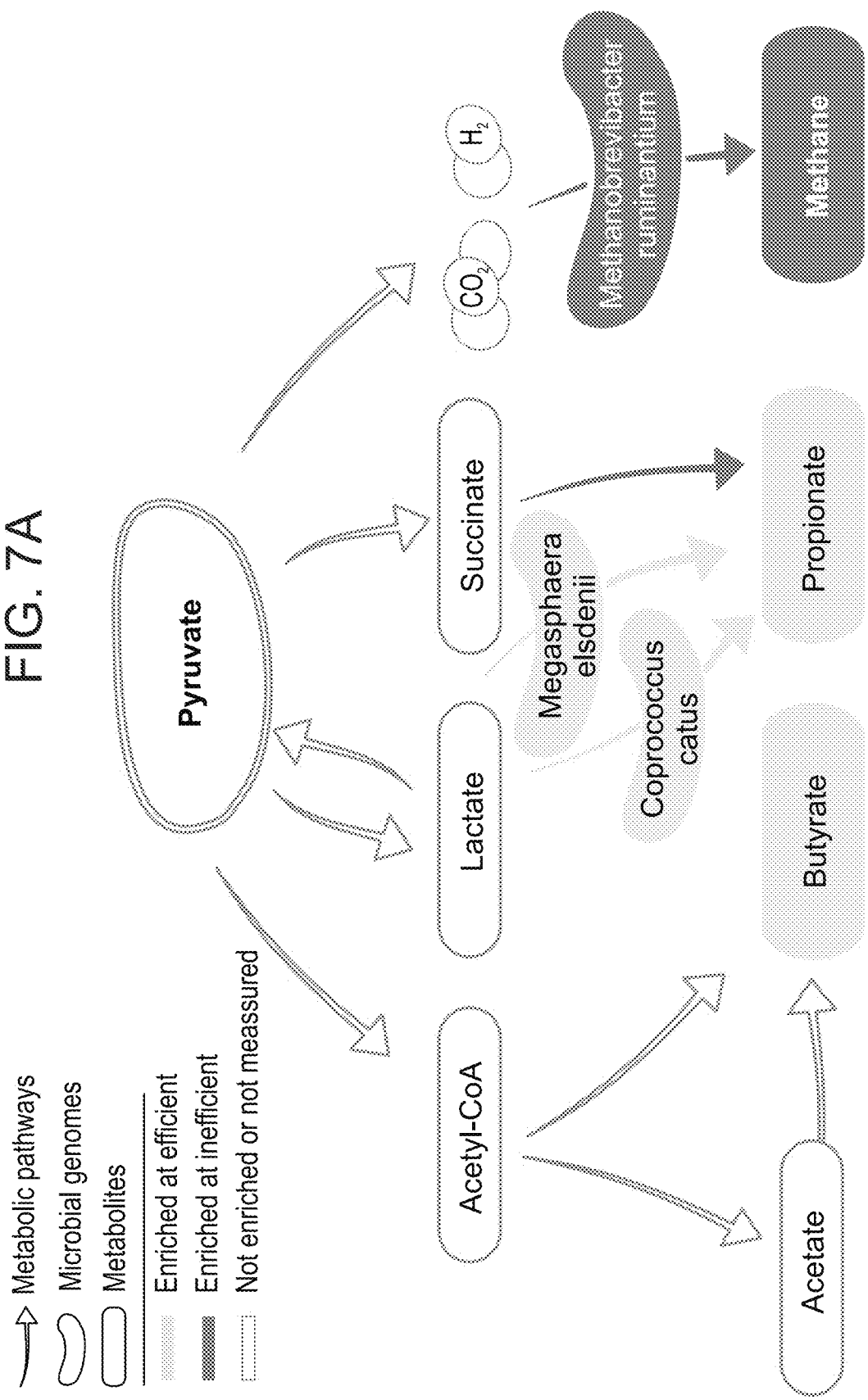

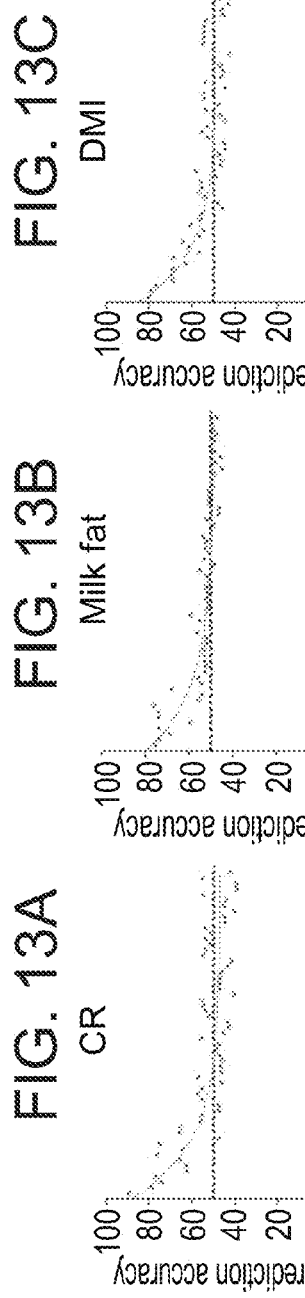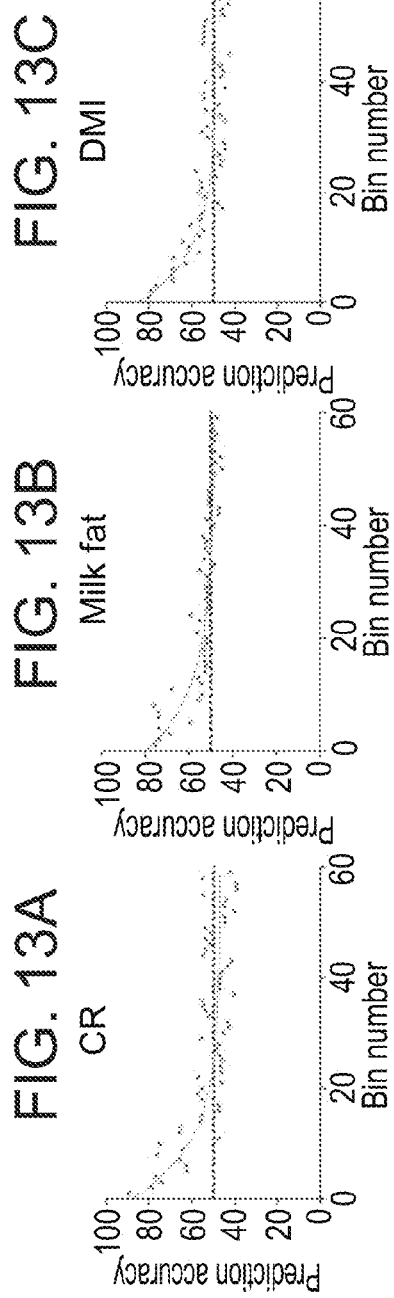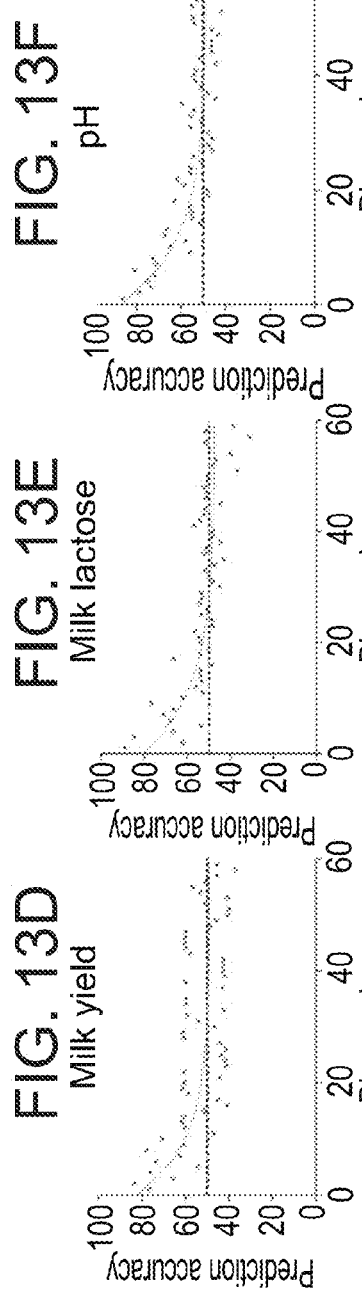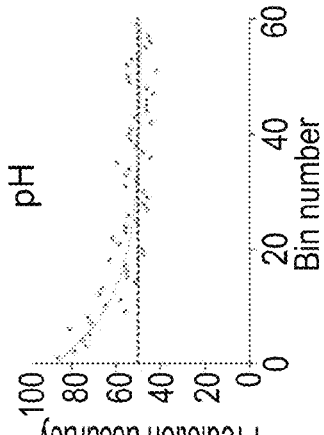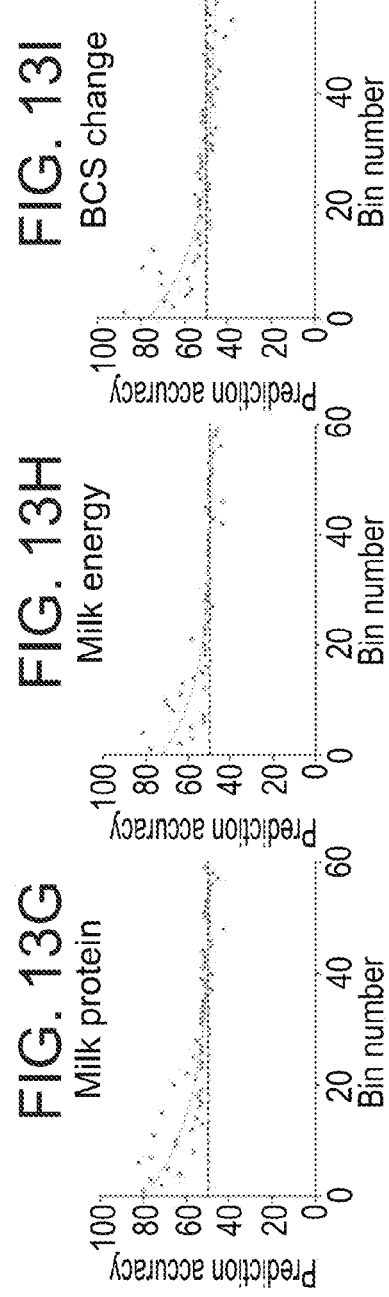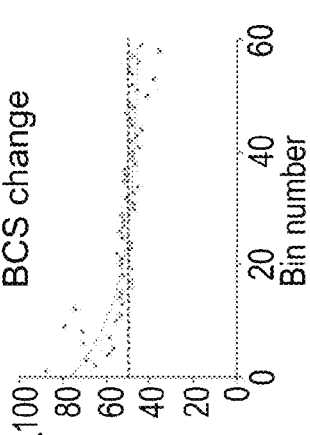

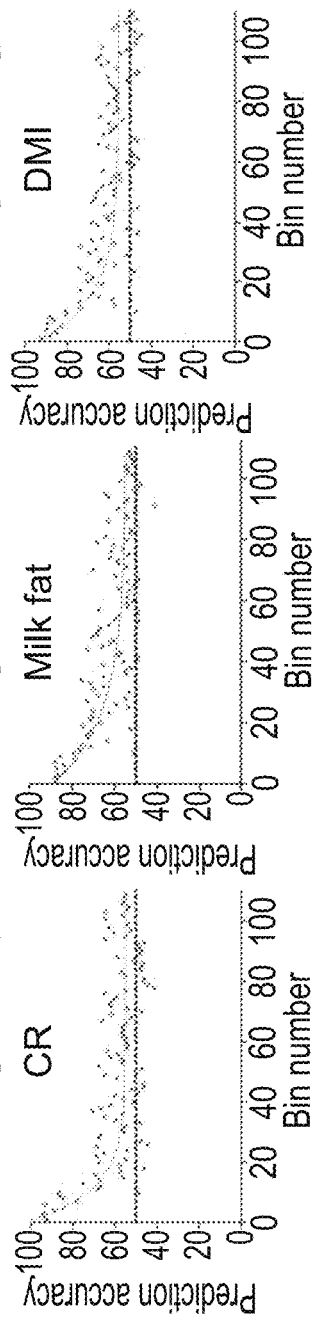
FIG. 14A CR
FIG. 14B Milk fat
FIG. 14C DMI
FIG. 14D Milk yield
FIG. 14E Milk lactose
FIG. 14F pH
FIG. 14G Milk protein
FIG. 14H Milk energy
FIG. 14I BCS change

REGULATION OF FEED EFFICIENCY AND METHANE PRODUCTION IN RUMINATING ANIMALS

RELATED APPLICATIONS

This application is a National Phase of PCT Patent Application No. PCT/IL2016/051197 having International filing date of Nov. 3, 2016, which claims the benefit of priority under 35 USC § 119(e) of U.S. Provisional Patent Application No. 62/327,616 filed on Apr. 26, 2016. The contents of the above applications are all incorporated by reference as if fully set forth herein in their entirety.

SEQUENCE LISTING STATEMENT

The ASCII file, entitled 75758SequenceListing.txt, created on Oct. 25, 2018, comprising 10,705 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to rumen microflora and uses thereof. In one embodiment, the present invention relates to rumen microflora in order to regulate feed efficiency and methane production in ruminating animals.

Ruminants hold enormous significance for man, as they convert the energy stored in plant-biomass polymers, which are indigestible for humans, to digestible food products. Humans domesticated these animals for this purpose in the Neolithic era and have been farming them ever since for the production and consumption of animal protein in the form of meat and milk. In today's extensive production regimes, ruminants consume 30% of the crops grown on earth and occupy another 30% of the earth's land mass. These animals also emit methane—a highly potent greenhouse gas—to the atmosphere and are considered to be responsible for a considerable portion of its emission due to anthropogenic activities. One way to tackle these problems is to increase the animals' energetic efficiency, i.e., the efficiency with which they convert energy from feed, thereby increasing food availability while lowering the environmental burden, as these animals would produce more and eat less.

Different methods are used to evaluate an animal's energetic efficiency; of these, the residual feed intake (RFI) method (Koch et al., 1963) is highly accepted and widely used as it is independent of growth and body size and is thus suitable for comparisons between animals. This parameter is an estimation of the difference between an animal's actual feed intake and its predicted feed intake based on its production level and body weight. The energetic efficiency varies considerably between different individuals from the same breed. Specific genomic regions, such as one that is suggested to be associated with a role in controlling energy metabolism, have been found to correlate to feed efficiency using genome wide association studies. Nevertheless, only a moderate genetic component (heritability ranging from 0.26 to 0.58) affects energy utilization, as has also been demonstrated by elevation of feed-efficiency via selection of animals according to their RFI.

One important factor that could greatly contribute to variations in these animals' feed-efficiency is the rumen microbiome. The ability of these animals to digest plant-biomass polymers is attributed to this complex microbiome that resides in their upper digestive tract in a compartment termed the rumen (Mizrahi, 2013). The anaerobic environment in the rumen and the highly complex food webs sustained by the rumen microbiome enable the fermentation of plant material into metabolic end products such as short-chain fatty acids (SCFAs) and methane. While SCFAs are absorbed through the rumen wall and serve to fulfill the animal's energy needs, methane is not absorbed; it is emitted to the atmosphere together with its retained energy, thereby contributing to energy loss from the feed as well as global warming (Mizrahi, 2011). Differences between high and low RFI animals have been reported in terms of methane production as well as of some differences in microbial composition (Nkrumah et al., 2006, Mizrahi, 2011, Hernandez-Sanabria et al., 2012, Jami et al., 2014, Kittelmann et al., 2014, Shi et al., 2014, Wallace et al., 2015). Nevertheless, a comprehensive and thorough understanding of microbiome structure patterns and how to translate them to functionality at the animal level is still lacking.

SUMMARY OF THE INVENTION

According to an aspect of the present invention there is provided a method of determining the feed efficiency and methane production of a ruminating animal comprising analyzing the number and/or diversity of a bacterial taxon of a microbiome of the animal or of a gene content of the microbiome, wherein a number and/or diversity of the taxon below a predetermined level is indicative of an animal having a high feed efficiency and low methane production, or a number of genes below a predetermined level is indicative of an animal having a high feed efficiency and low methane production.

According to an aspect of the present invention there is provided a method of determining feed efficiency and/or methane production in a ruminating animal comprising quantifying at least one bacterial species as set forth in Tables 4 and 5 in a microbiome of the animal, wherein when the level of at least one bacterial species in Table 4 is above a predetermined level it is indicative of a high feed efficiency or a low methane production and when the level of at least one bacterial species set forth in Table 5 is below a predetermined level, it is indicative of a high feed efficiency or a low methane production.

According to an aspect of the present invention there is provided a method of determining feed efficiency and/or methane production in a ruminating animal comprising quantifying at least one bacterial species of the genus *Megasphaera* in a microbiome of the animal, wherein when the level of the at least one bacterial species is above a predetermined level it is indicative of a high feed efficiency or a low methane production.

According to an aspect of the present invention there is provided a method of qualifying ruminating animals comprising:

(a) determining the feed efficiency or methane production of the ruminating animals as described herein; and (b) selecting the animals which have a high feed efficiency and low methane production.

According to an aspect of the present invention there is provided an anti-microbial composition comprising at least one agent which specifically downregulates at least one bacterial species which is set forth in Table 5.

According to an aspect of the present invention there is provided a method of determining the feed efficiency or methane production of a ruminating animal comprising analyzing the amount or composition of short chain fatty acids (SCFAs) of a metabolome of the animal, wherein the amount and/or composition of the SCFAs is indicative of the feed efficiency or methane production.

According to an aspect of the present invention there is provided a method of increasing the feed efficiency or decreasing the methane production of a ruminating animal comprising administering to the animal an agent which increases the amount of at least one bacterial species set forth in Table 4 in the rumen microbiome of the animal, thereby increasing the feed efficiency or decreasing the methane production of a ruminating animal.

According to an aspect of the present invention there is provided a method of increasing the feed efficiency or decreasing the methane production of a ruminating animal comprising administering to the animal an agent which increases the amount of the bacterial genus *Megasphaera* in the rumen microbiome of the animal, thereby increasing the feed efficiency or decreasing the methane production of a ruminating animal.

According to an aspect of the present invention there is provided a method of increasing the feed efficiency or decreasing the methane production of a ruminating animal comprising administering to the animal a composition comprising at least one agent which specifically down-regulates an amount of at least one bacteria set forth in Table 5, thereby increasing the feed efficiency or decreasing the methane production of a ruminating animal.

According to an aspect of the present invention there is provided a microbial composition comprising between 2-100 species of bacteria, wherein at least one of the species is as set forth in Table 4.

According to embodiments of the present invention, the at least one bacterial species is *Megasphaera elsdenii* or *Coprococcus catus*.

According to embodiments of the present invention, the microbiome is a non-pathogenic microbiome.

According to embodiments of the present invention, the microbiome comprises a rumen microbiome or fecal microbiome.

According to embodiments of the present invention, the determining an amount is effected by analyzing the expression of at least one gene of the genome of the at least one bacteria.

According to embodiments of the present invention, the at least one bacterial species is *Megasphaera elsdenii*.

According to embodiments of the present invention, when the amount of propionate, butyrate, valerate and/or isovalerate in the metabolome of the animal is above a predetermined level, it is indicative of the animal having a high feed efficiency and a low methane production.

According to embodiments of the present invention, the number of the taxon is analyzed up to the phylum level.

According to embodiments of the present invention the diversity of the taxon is analyzed at the species level.

According to embodiments of the present invention, when the amount of total SCFAs in the metabolome of the animal is above a predetermined level, it is indicative of the animal having a high feed efficiency and a low methane production.

According to embodiments of the present invention, when the ratio of propionate: acetate in the metabolome of the animal is higher than a predetermined amount, it is indicative of the animal having a high feed efficiency and a low methane production.

According to embodiments of the present invention, the agent comprises the at least one bacterial species.

According to embodiments of the present invention, the agent comprises the bacterial genus.

According to embodiments of the present invention, the agent is not an antibiotic.

According to embodiments of the present invention, the ruminating animal is younger than 6 months old.

According to embodiments of the present invention, the composition is comprised in a feed.

According to embodiments of the present invention, the composition is comprised in a silage.

According to embodiments of the present invention, the composition is comprised in an enema.

According to embodiments of the present invention, the animal is treated with an antibiotic composition prior to the administering.

According to embodiments of the present invention, the composition is devoid of fecal material.

According to embodiments of the present invention, the composition is formulated as a feed, a silage or an enema.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-G. Community parameters of efficient and inefficient cows' microbiomes. (A-B) Microbiome richness. Species (based on 16S amplicon sequencing) (A) and gene (based on metagenomics sequencing) (B) counts were calculated and expressed as simple richness. Kernel density of the efficient and inefficient histograms emphasizes the different distribution of counts in each microbiome group. P-values of the difference in richness between efficient and inefficient cows are shown. (C) Microbiome richness at different phylogenetic levels. (D-E) Alpha diversity (Shannon index) measurements according to species (D) and genes (E). (F-G) Dominance of the microbiome according to species (F) and genes (G). Data are expressed as mean±SEM. Wilcoxon rank-sum, *P<0.05, **P<0.01.

Figure 2A:
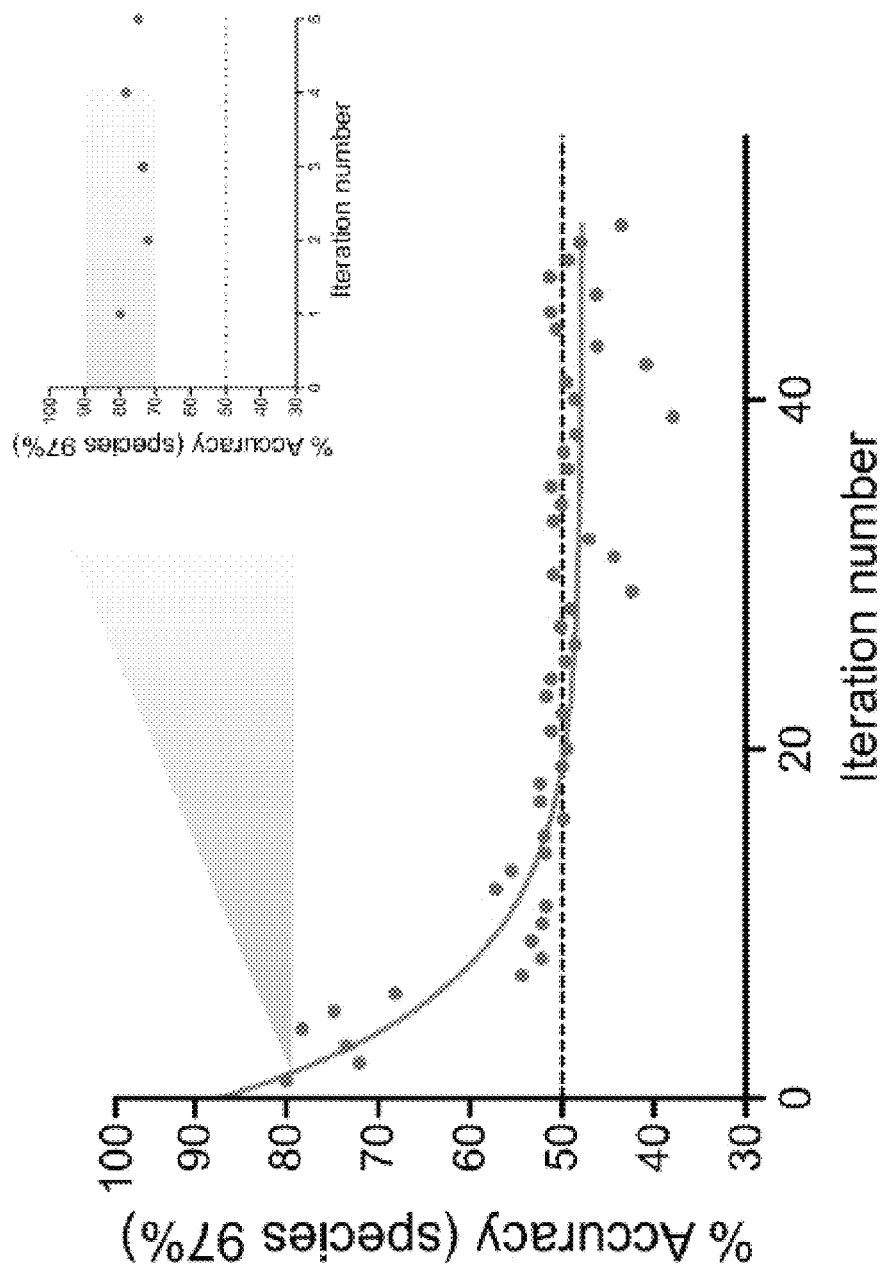
Figure 2B:
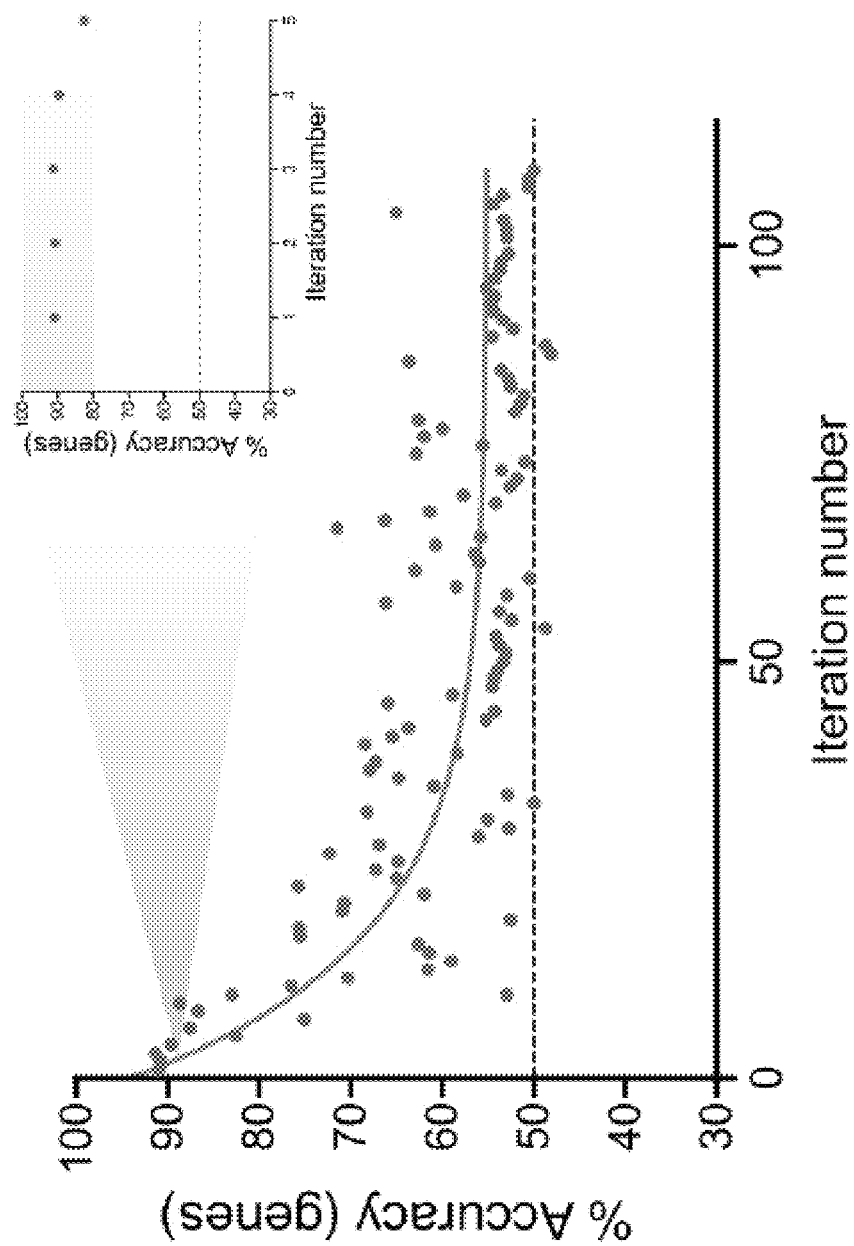

FIGS. 2A-B. Feed-efficiency predictions according to species and genes. Species (a) and genes (b) that differed in abundance between efficient and inefficient cows were ranked according to their P-values and grouped into bins of 100. The bins were used as predictive features for the RFI feed-efficiency parameter using the k-Nearest Neighbors (KNN) algorithm with k=3. Each iteration used a different bin as predictive features, in ascending P-value order. Inset in both graphs represents the first five prediction-accuracy values (Permutations of random classes shuffling, P-value=0.009).

Figure 3:
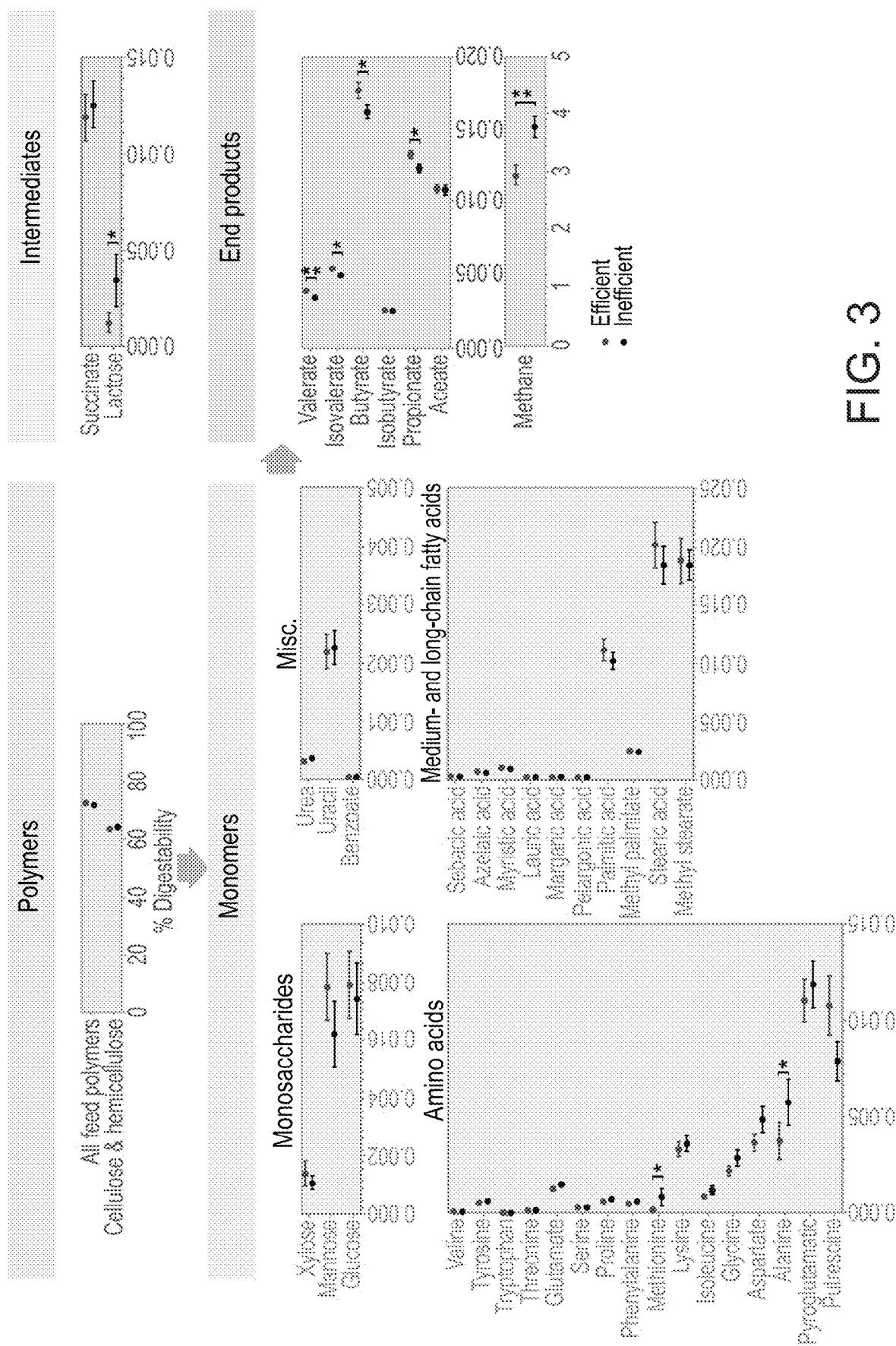

FIG. 3. Metabolome and microbial activity of rumen microbiomes of efficient and inefficient cows. In vivo and in vitro digestibility methods were performed on rumen fluid of efficient and inefficient cows in addition to extraction, identification and quantification of 41 different metabolites by GC and GC-MS. These metabolites were normalized to the organic matter content of the rumen fluid from which they were extracted. Metabolites are organized according to trophic levels. Multiple hypothesis correction with 9,999 permutations was performed individually for each metabolic or activity test using the t statistic (Methods).
Data are expressed as mean±SEM. *P<0.05, **P<0.01.

Figure 4A:
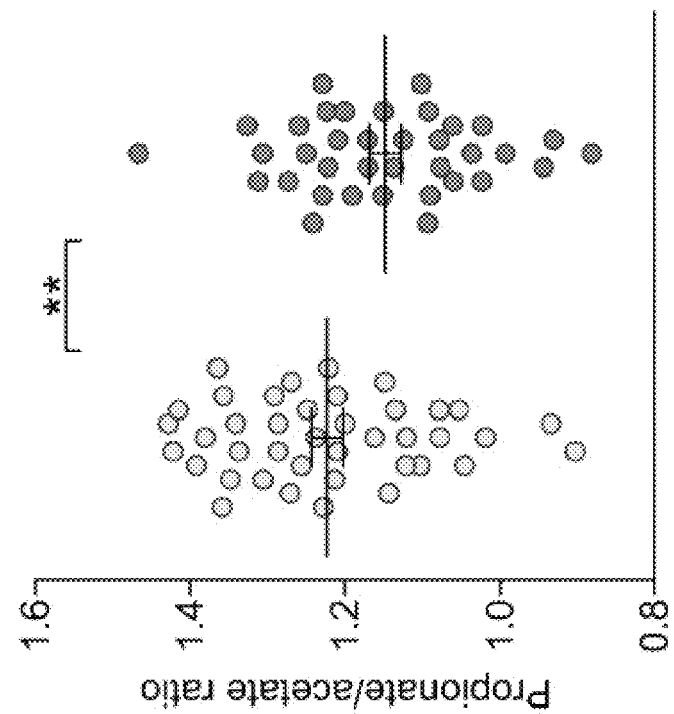
Figure 4B:
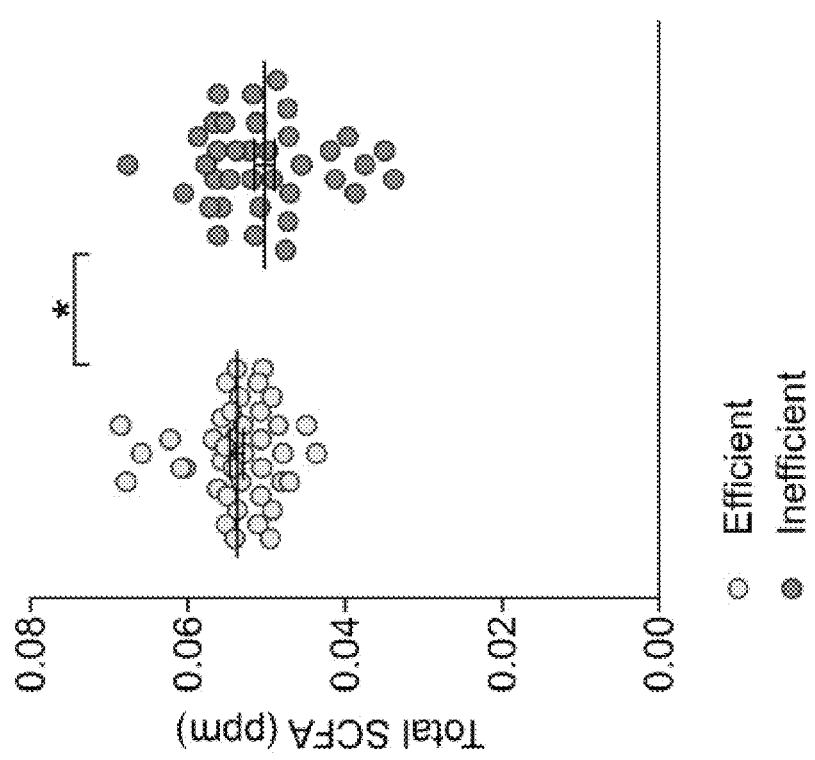

FIGS. 4A-B. SCFA concentration in rumen fluids of efficient and inefficient cows. (A) Total SCFA concentrations in efficient and inefficient rumen samples. (B) Propionate/acetate ratio in the efficient and inefficient rumen samples. Data are expressed as mean±SEM. *P<0.05, **P<0.01.

Figure 5B:
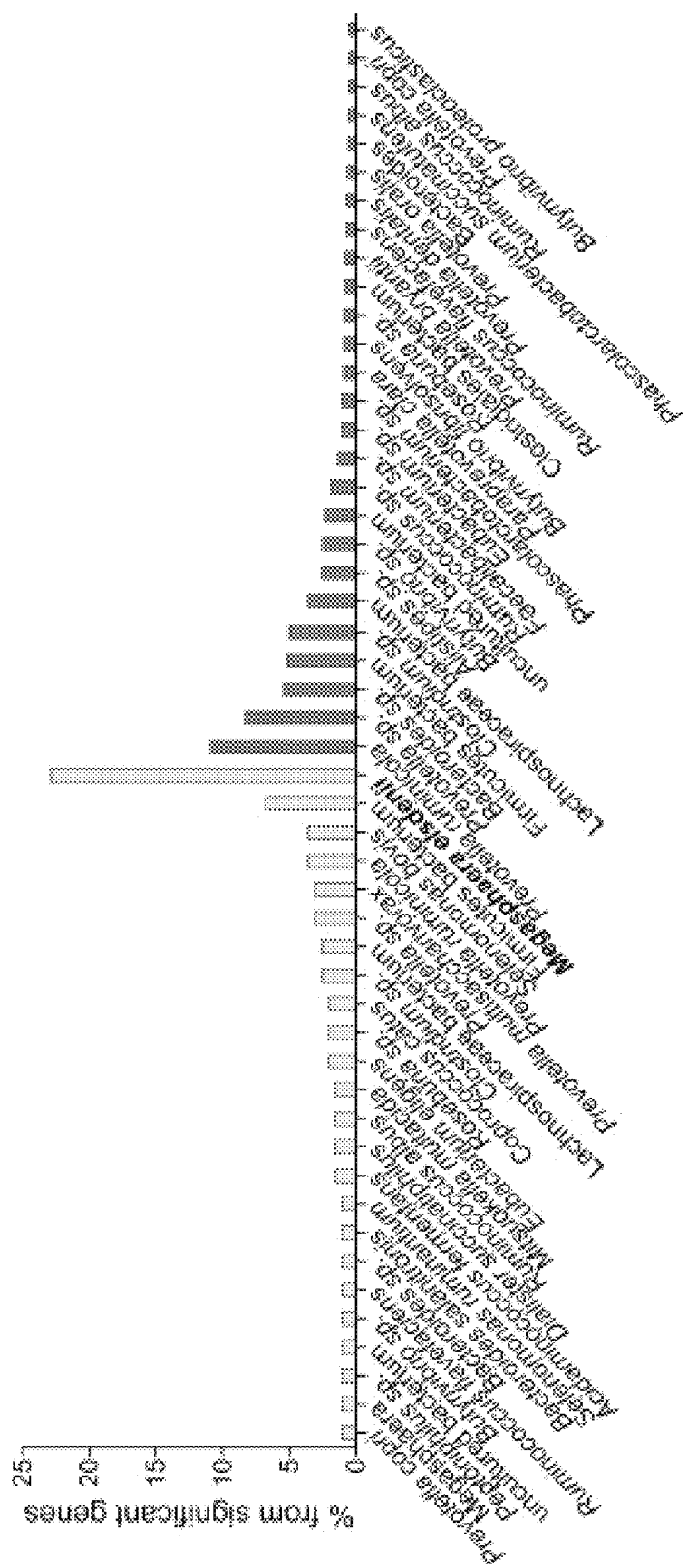

FIGS. 5A-B. Taxonomic annotations of species and genes enriched in each microbiome group. (A) Spearman's correlation of significantly enriched species to the feed-efficiency parameter. The annotations are presented at the lowest phylogenetic level obtained, as well as at the order level in parentheses. (B) The distribution of the phylogenetic annotations of genes enriched in each of the microbiome groups. Phylogenetic annotations above a threshold of 2% are presented.

Figure 6A:
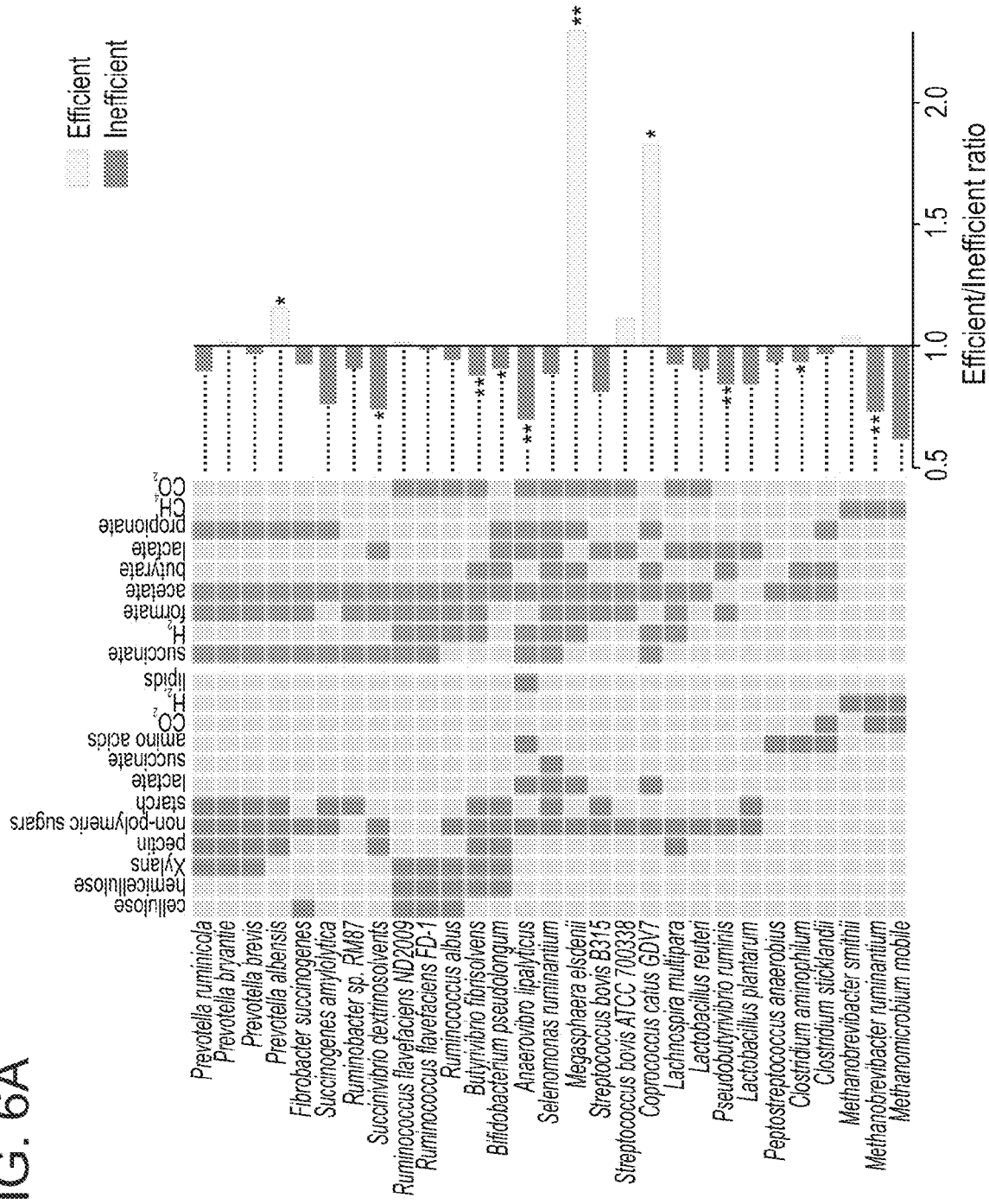
Figure 6B:
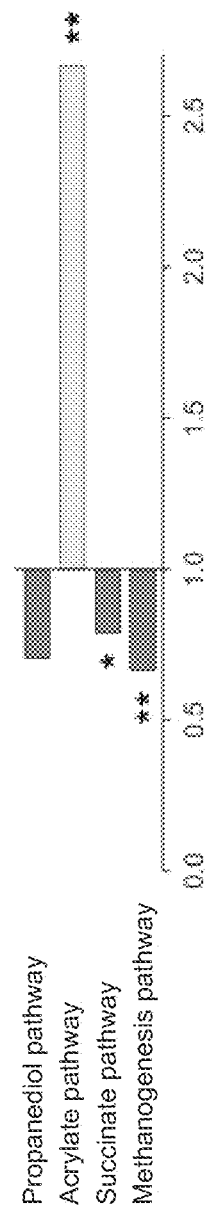

FIGS. 6A-B. Microbiome features enriched in each microbiome group. (A) Reads from each sample were aligned to sequenced genomes of known rumen microorganisms using the BWA tool. The ratios between alignments of efficient/inefficient samples to each genome are presented. The utilization and production of metabolites for each microorganism based on the known growth characteristics (Holdman & Moore, 1974, Russell & Rychlik, 2001, Duncan et al., 2009) are colored in blue and orange, respectively. (B) Reads from each sample were aligned to KEGG enzymes of different metabolic pathways using the BWA tool. Propanediol, acrylate and succinate pathways are different propionate production pathways. The ratios between alignments of efficient/inefficient samples to each pathway are presented. Data are expressed as ratio of means. Permutations t test,*P<0.05, **P<0.01.

Figure 7B:
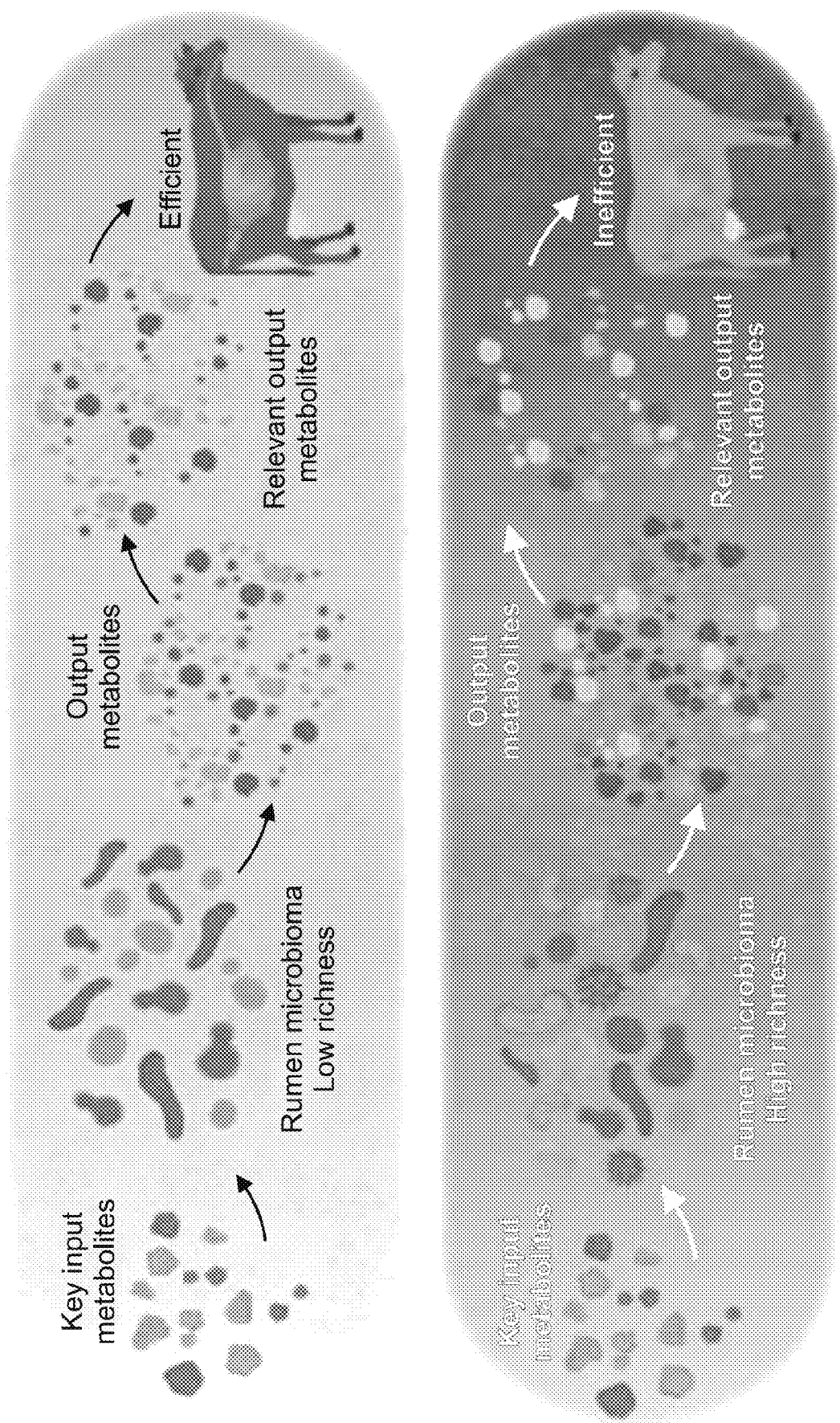

FIGS. 7A-B. Consolidated results and model. (A) Consolidation of results from the metabolomics, genome and pathway recruitment analyses. Green: pathways and metabolites that were not significantly different or that were not assessed. Red: enriched in efficient microbiomes. Grey: enriched in inefficient microbiomes. (B) Proposed model. From left to right: identical key input metabolites are ingested by the cow and presented to either an efficient microbiome (top panel) with lower richness and diversity, or an inefficient microbiome (bottom panel) with higher richness and diversity. Differences in richness result in the production of different metabolites. The efficient microbiome produces a smaller range of output metabolites than the inefficient microbiome, however with larger amounts of relevant output metabolites which are available for the animal's energetic needs.

Figure 8:
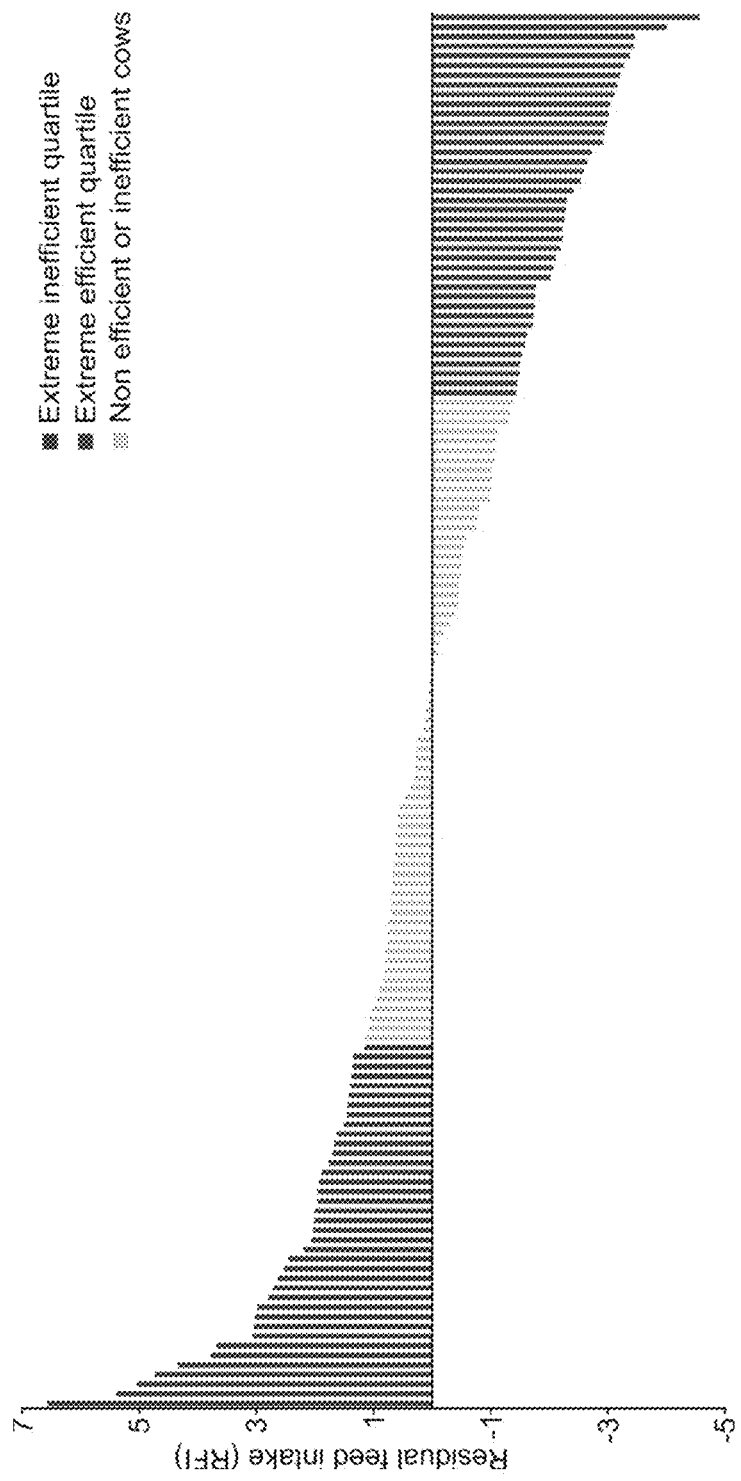

FIG. 8. RFI Population Distribution of the Trial Cohort (146 Cows). Cows with extreme low (n=40) and extreme high (n=38) RFI, are colored red and grey, respectively and represent the 25% most and 25% least efficient from a cohort of 146 cows. These 78 cows were chosen for rumen and fecal sampling.

Figure 9:
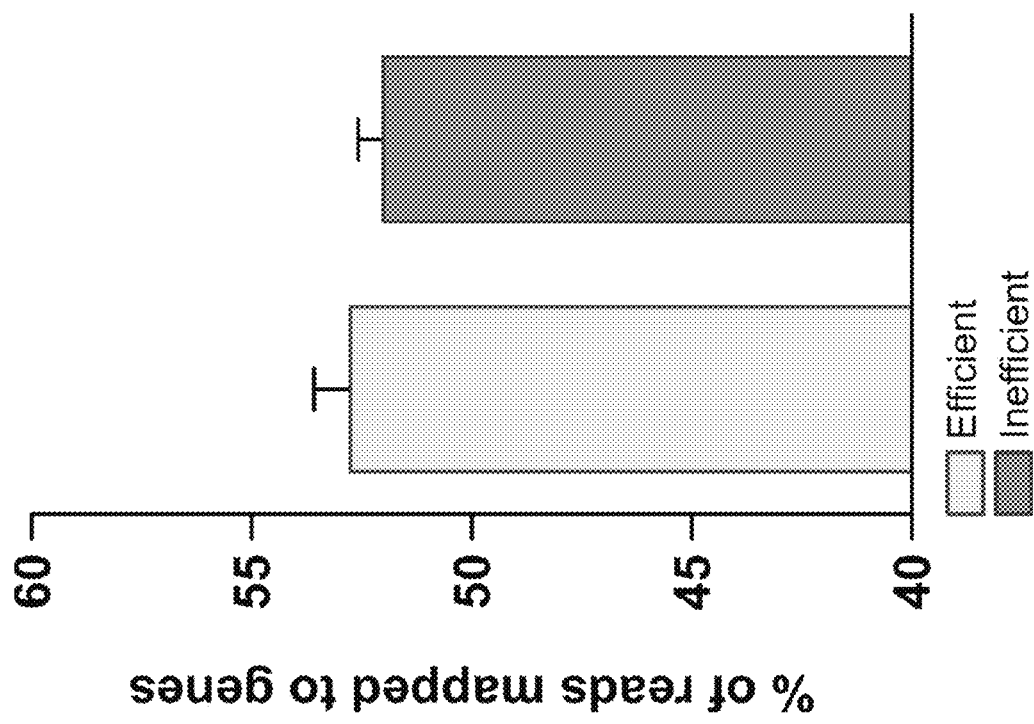

FIG. 9. Percentage of Mapped Reads From Efficient and Inefficient Cows' Samples to the Total Microbiome Genes. Data are expressed as mean±SEM.

Figure 10:
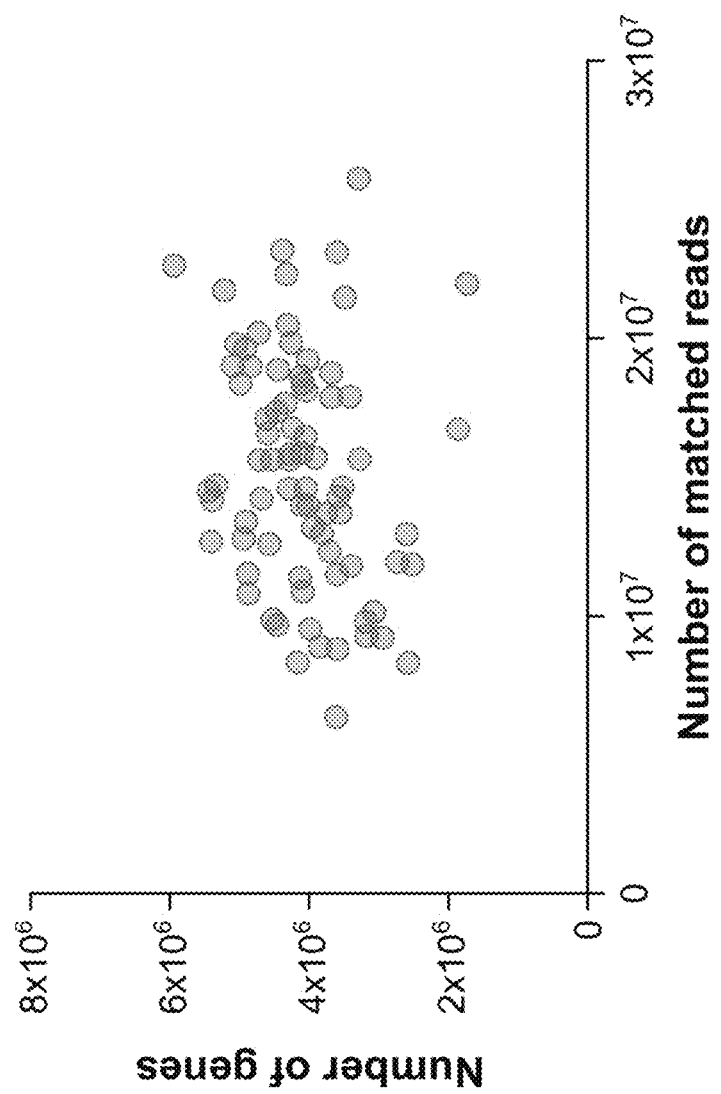

FIG. 10. Number of Genes in a Sample As a Function of the Number of Reads. Reads from each sample were aligned to the total genes. The number of aligned reads is plotted against the number of genes obtained for each sample. No correlation was found between the two variables (P-value=0.074).

Figure 11:
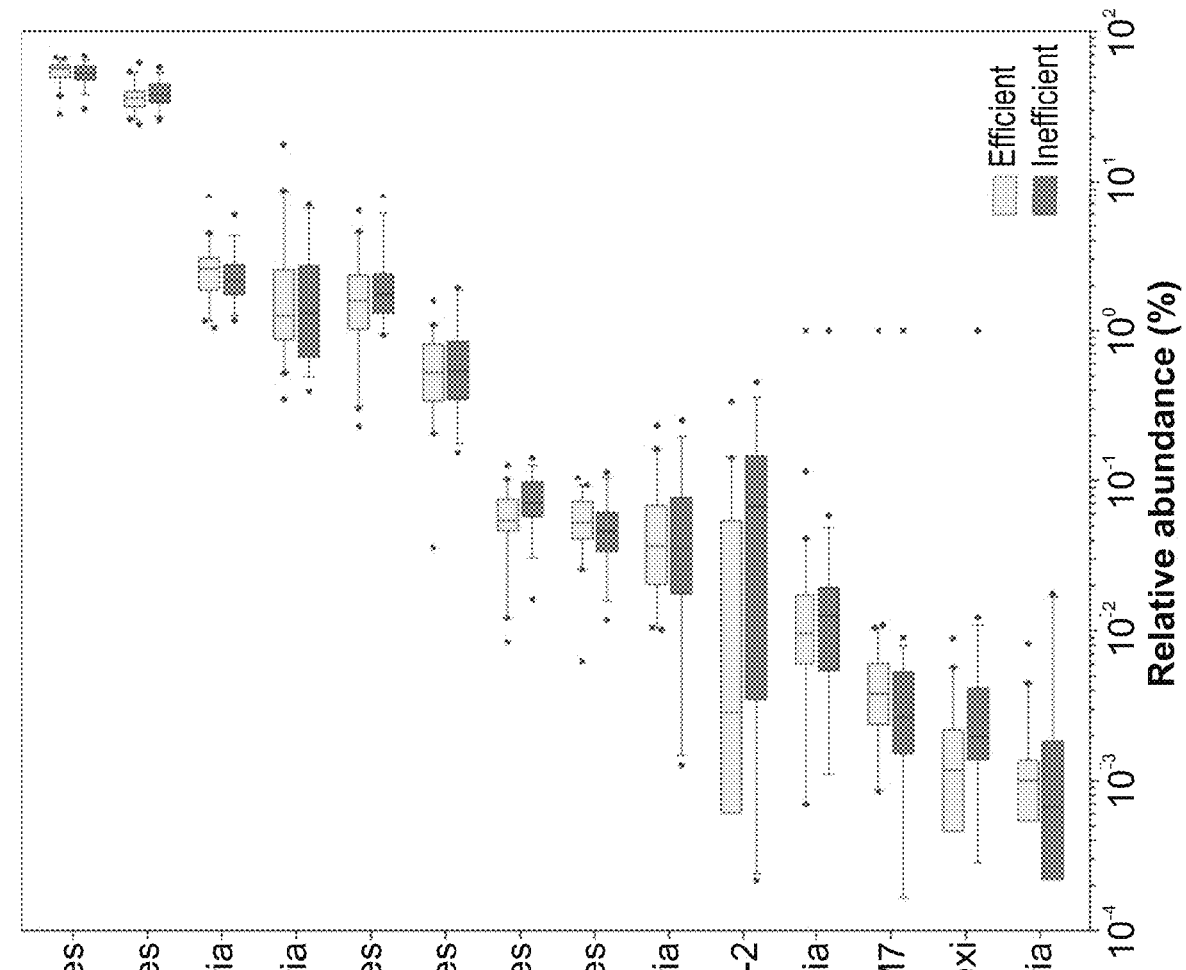

FIG. 11. Phyla Abundances. Microbiome composition of the two efficiency groups at the phylum level. Phyla with relative abundance above 0.001% are presented. Data are expressed as mean±SEM.

Figure 12A:
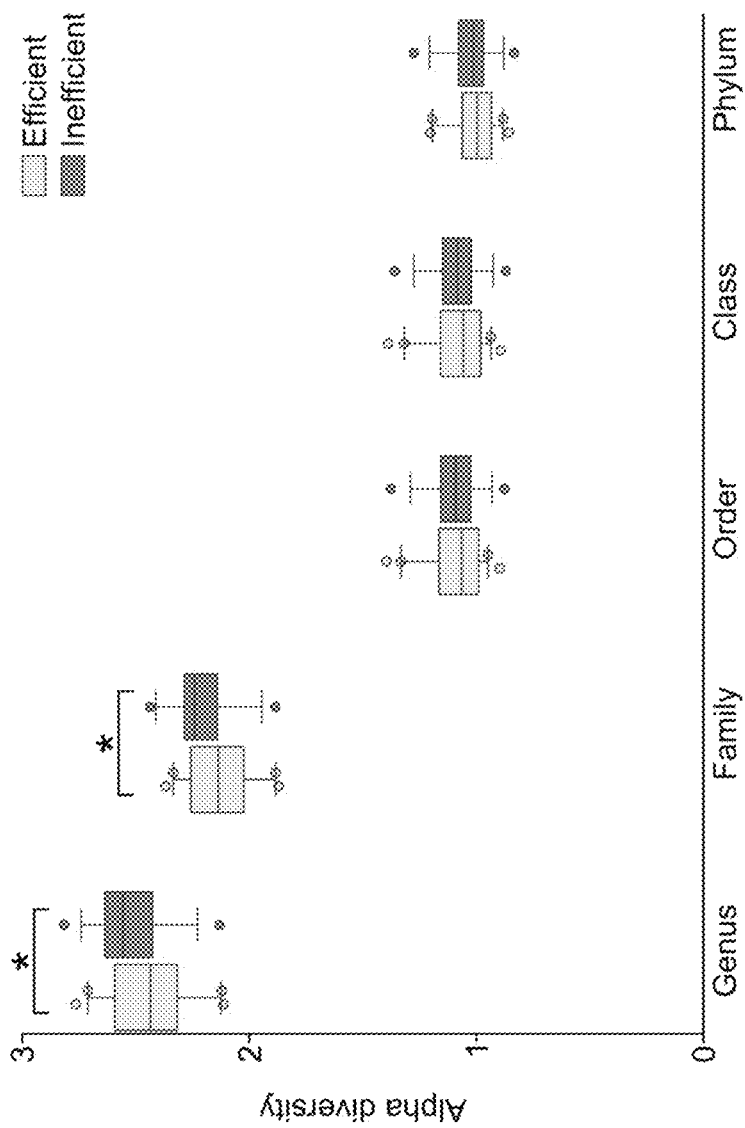
Figure 12B:
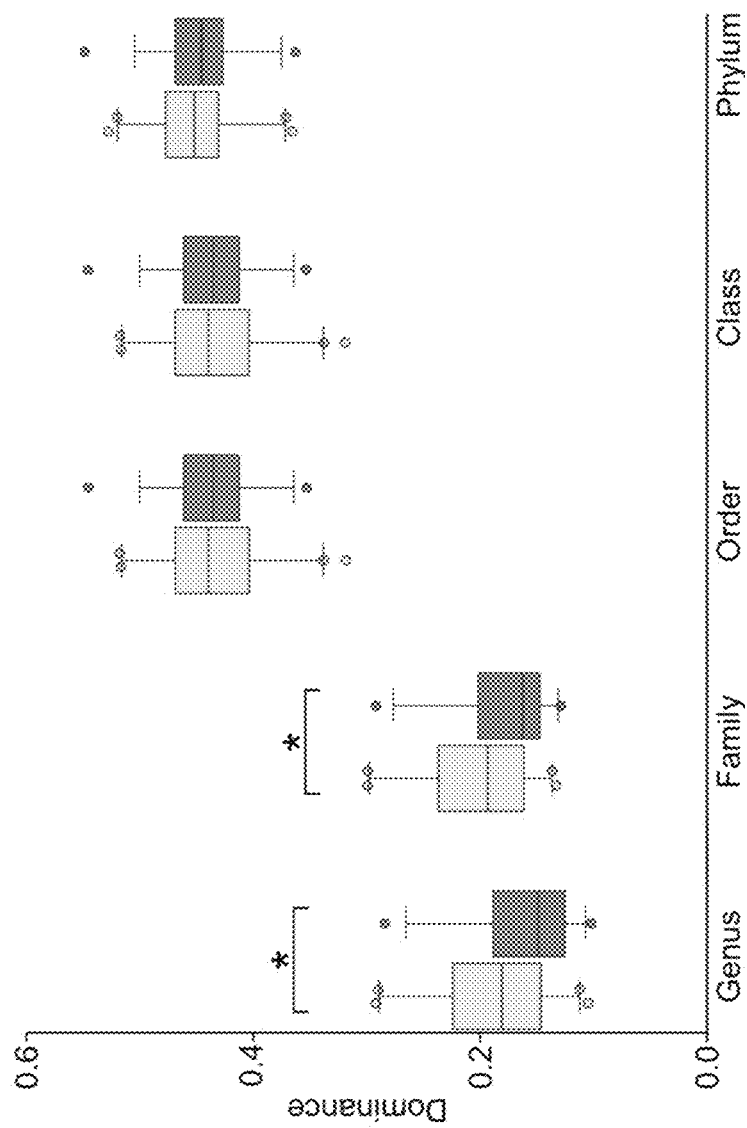
Figure 15A:
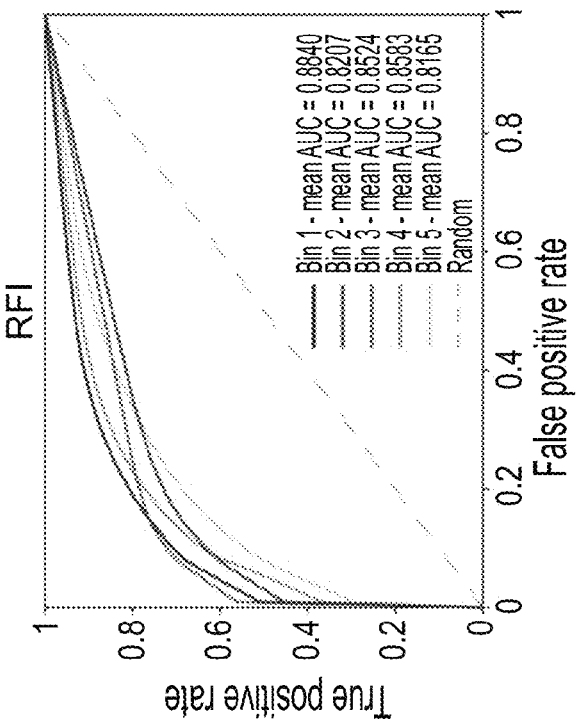
Figure 15B:
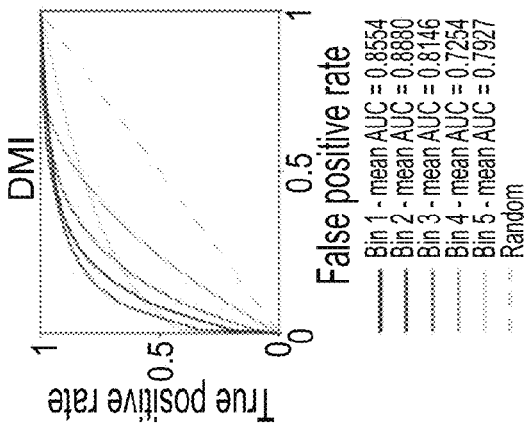
Figure 15C:
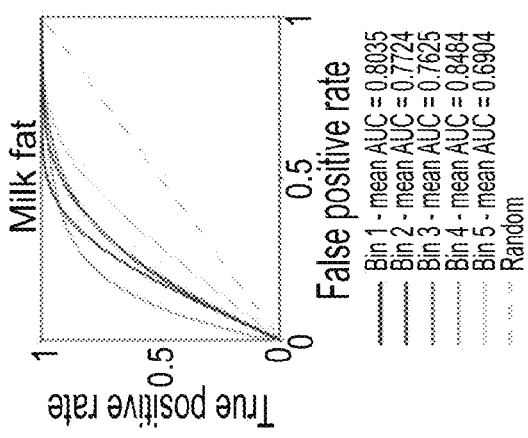
Figure 15D:
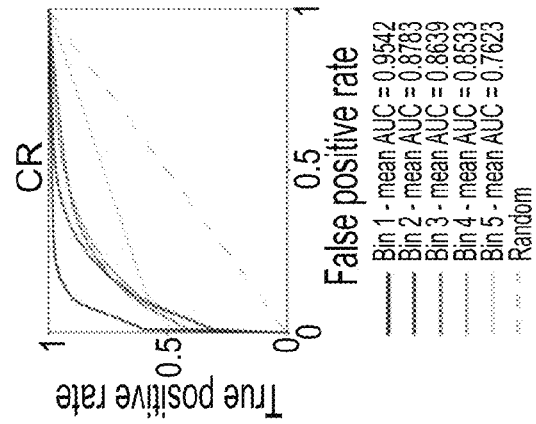
Figure 15G:
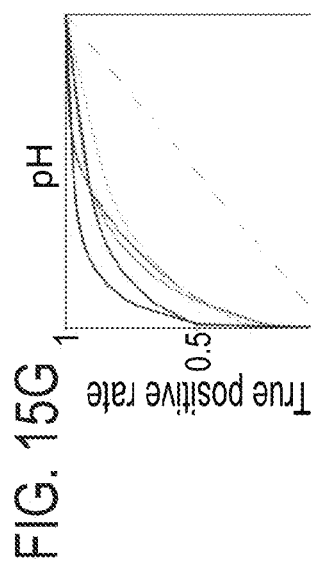
Figure 15F:
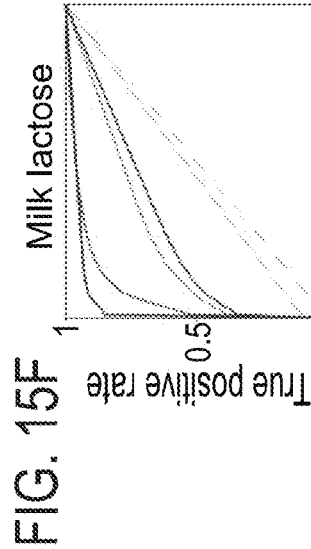
Figure 15E:
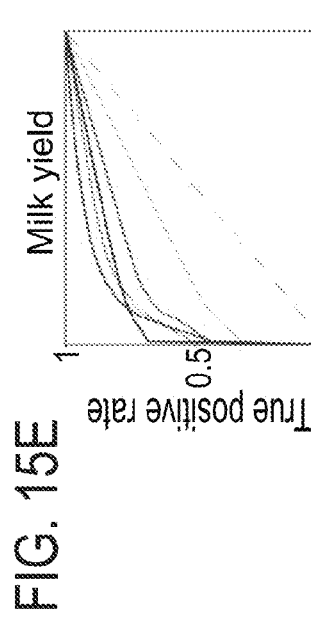
Figure 15J:
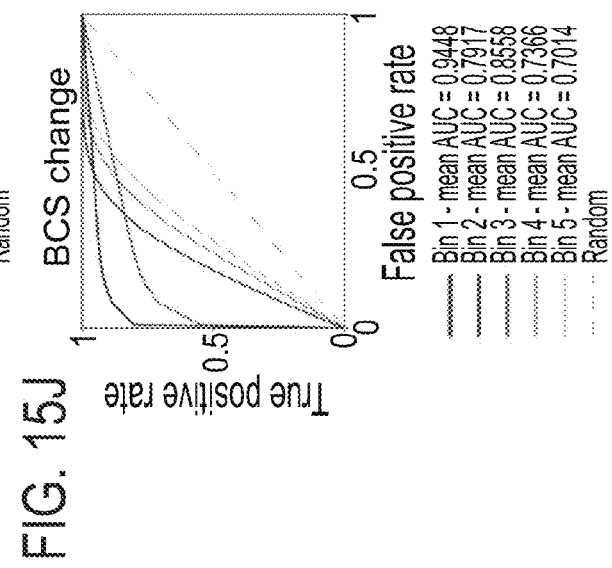
Figure 15I:
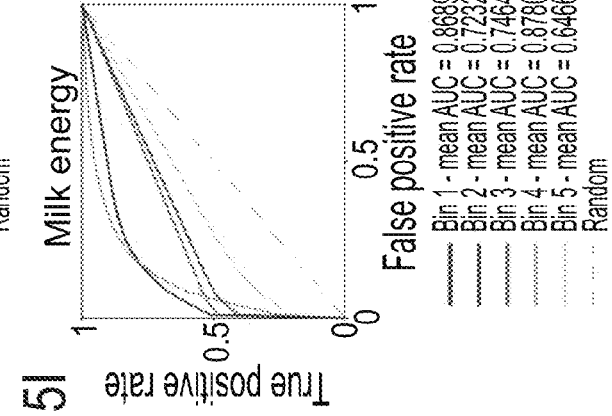
Figure 15H:
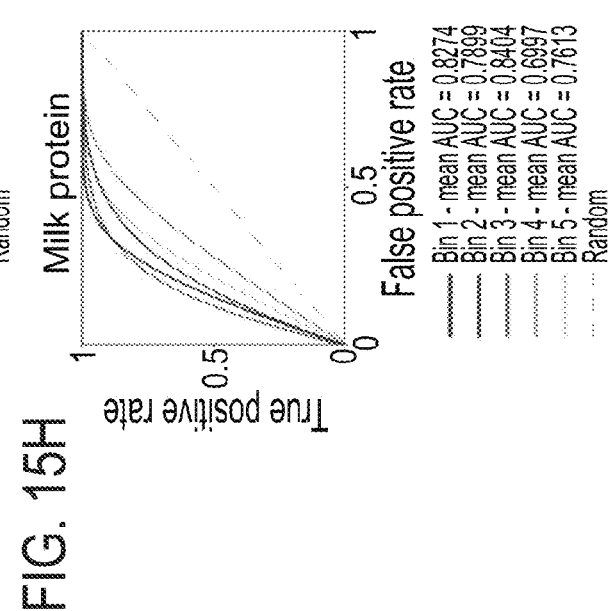
Figure 16A:
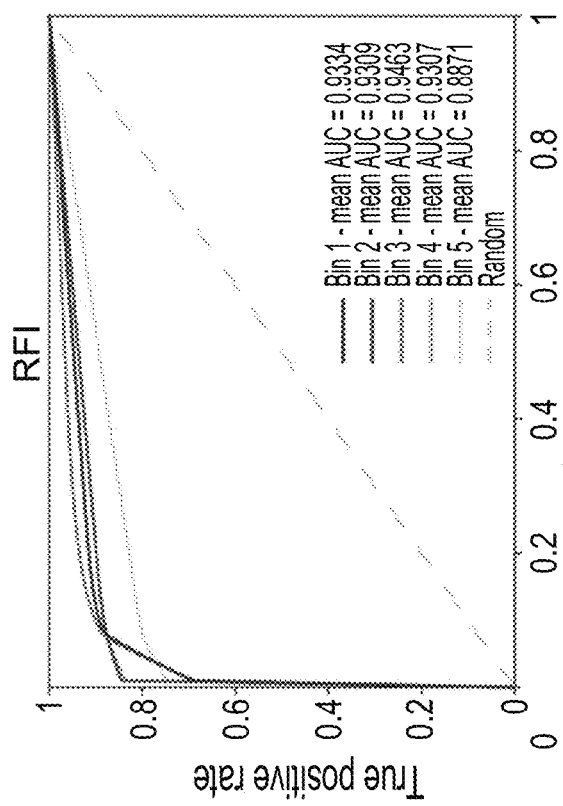
Figure 16D:
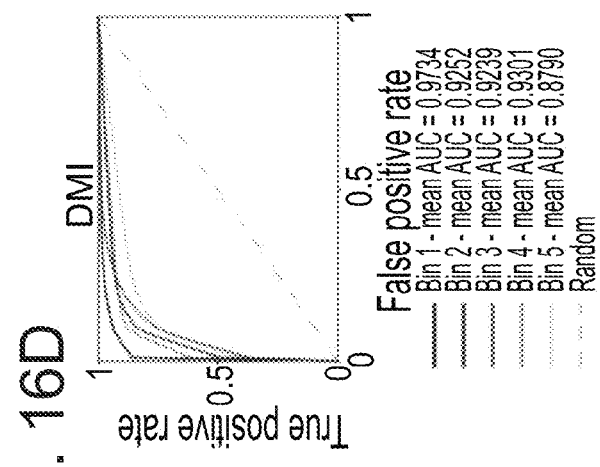
Figure 16C:
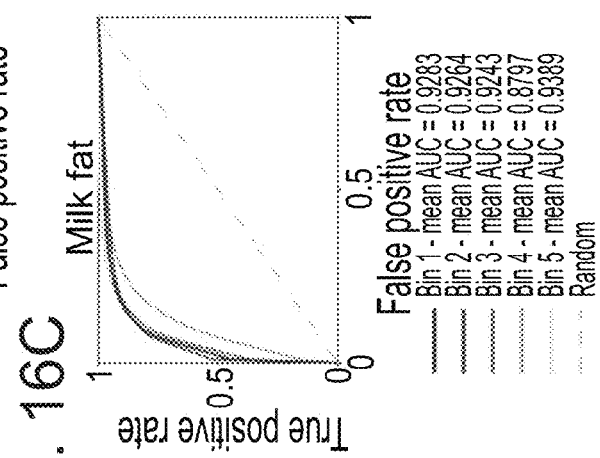
Figure 16B:
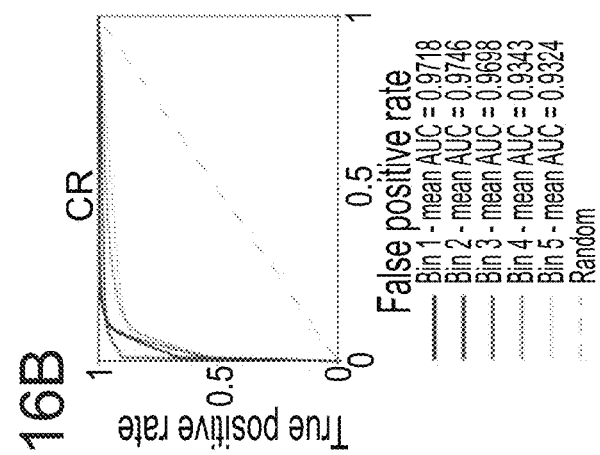
Figure 16E:
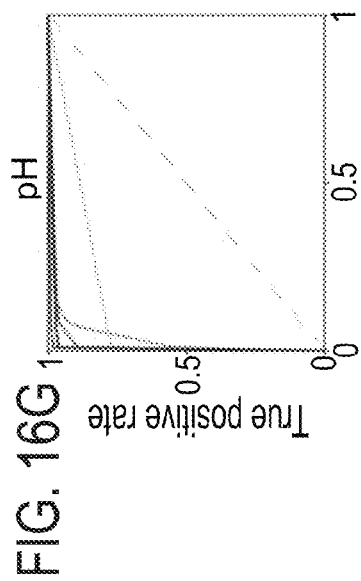
Figure 16F:
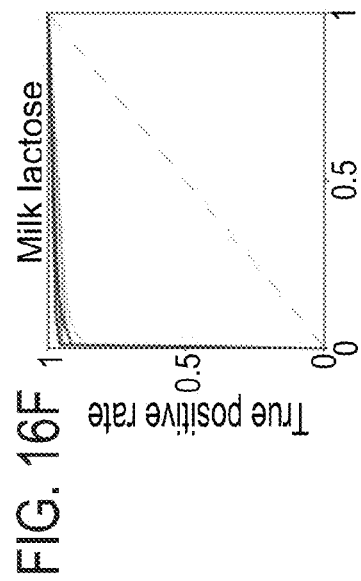
Figure 16H:
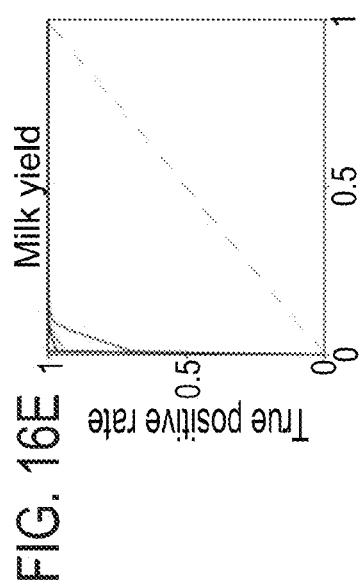
Figure 16G:
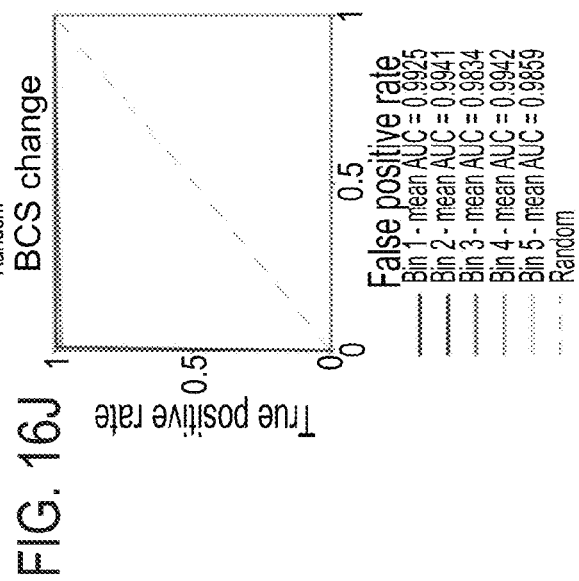
Figure 16I:
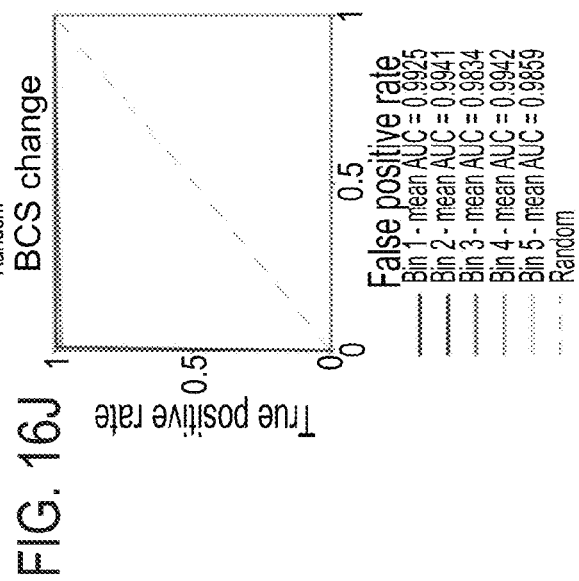
Figure 16J:
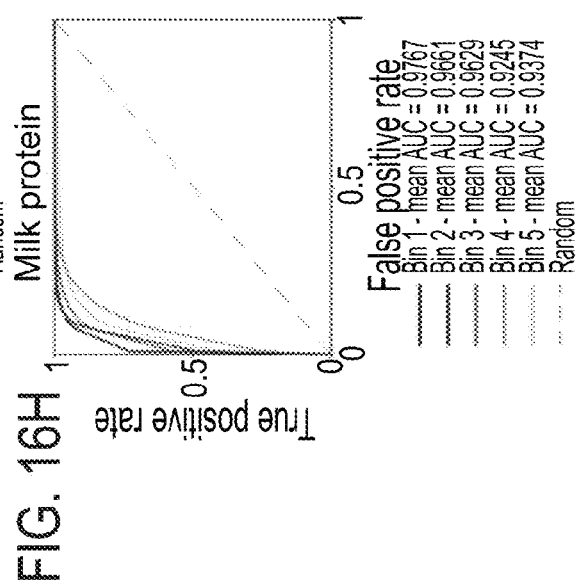
Figures 17A, 17B, 17C, 17D:
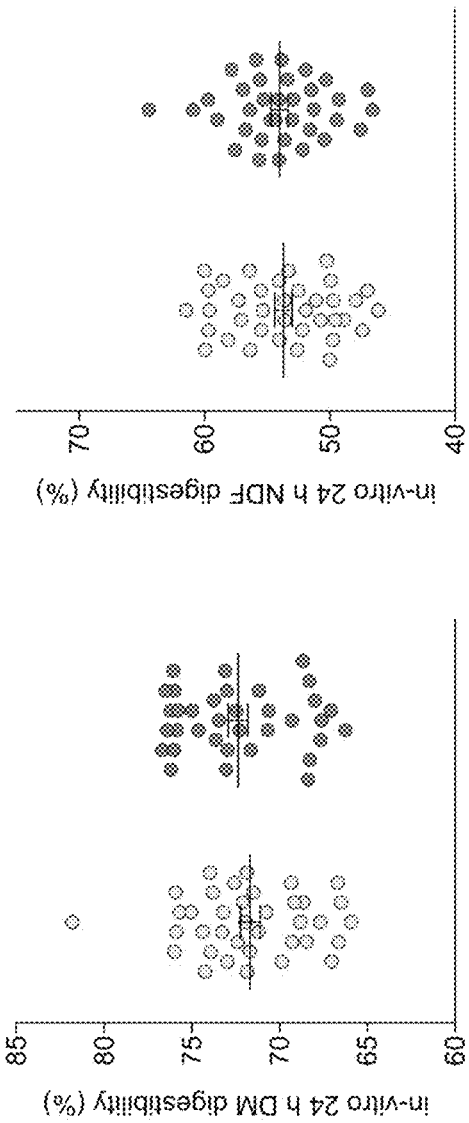

FIGS. 12A-B. Shannon Diversity and Dominance of Efficient and Inefficient Microbiomes. (A) Shannon diversity at different phylogenetic levels. (B) Dominance at different phylogenetic levels. Data are expressed as mean±SEM. Wilcoxon rank sum, *P<0.05.

FIGS. 13A-I. Prediction of Physiological and Metabolic Traits According to Species. Species that differed in abundance between efficient and inefficient cows were sorted according to their P-values and grouped into bins of 100. The bins were used as predictive features for the different physiological parameters using the k-Nearest Neighbors (KNN) algorithm with k=3. Each iteration used a different bin as predictive features, in ascending P-value order. (A) Conversion ratio (CR) prediction accuracy. (B) Milk fat prediction accuracy. (C) Dry matter intake (DMI) prediction accuracy. (D) Milk yield prediction accuracy. (E) Milk lactose prediction accuracy. (F) pH prediction accuracy. (G) Milk protein prediction accuracy. (H) Milk energy prediction accuracy. (I) Body conditioning score (BCS) change prediction accuracy.

FIGS. 14A-I. Prediction of Physiological and Metabolic Traits According to Genes. Genes that differed in abundance between efficient and inefficient cows were sorted according to their P-values and grouped into bins of 100. The bins were used as predictive features for the different physiological parameters using the k-Nearest Neighbors (KNN) algorithm with k=3. Each iteration used a different bin as predictive features, in ascending P-value order. Different graphs represent predictions of different physiological parameters. (A) CR prediction accuracy. (B) Milk fat prediction accuracy. (C) DMI prediction accuracy. (D) Milk yield prediction accuracy. (E) Milk lactose prediction accuracy. (F) pH prediction accuracy. (G) Milk protein prediction accuracy. (H) Milk energy prediction accuracy. (I) BCS change prediction accuracy.

FIGS. 15A-J. Specificity and Sensitivity Evaluation of Predictions of Physiological and Metabolic Traits According to Species. Receiver Operation Characteristics (ROC) curves and Area Under Curve (AUC) measures were obtained for the first five prediction bins (see FIG. 2A, FIG. 11) based on the average of 1,000 KNN cross-validation iterations. (A) RFI. (B) CR ROC analysis. (C) Milk fat ROC analysis. (D) DMI ROC analysis. (E) Milk yield ROC analysis. (F) Milk lactose ROC analysis. (G) pH ROC analysis. (H) Milk protein ROC analysis. (I) Milk energy ROC analysis. (J) BCS change ROC analysis.

FIGS. 16A-J. Specificity and Sensitivity Evaluation of Predictions of Physiological and Metabolic Traits According to Genes. Receiver Operation Characteristics (ROC) curves and Area Under Curve (AUC) measures were obtained for the first five prediction bins (see FIG. 2B, FIGS. 12A-B) based on the average of 1,000 KNN cross-validation iterations. (A) RFI. (B) CR ROC analysis. (C) Milk fat ROC analysis. (D) DMI ROC analysis. (E) Milk yield ROC analysis. (F) Milk lactose ROC analysis. (G) pH ROC analysis. (H) Milk protein ROC analysis. (I) Milk energy ROC analysis. (J) BCS change ROC analysis.

FIGS. 17A-D. In-Vitro Digestibility and In Vivo Digestibility. (A) In-vitro dry matter (DM) digestibility of feed after 24 h incubation with rumen fluid of efficient and inefficient cows. (B) In-vitro neutral detergent fiber (NDF) digestibility of feed after 24 h incubation with rumen fluid of efficient and inefficient cows. (C) In-vivo DM digestibility of efficient and inefficient stool samples. (D) In-vivo NDF digestibility of efficient and inefficient stool samples. Data are expressed as mean±SEM.

Figure 18:
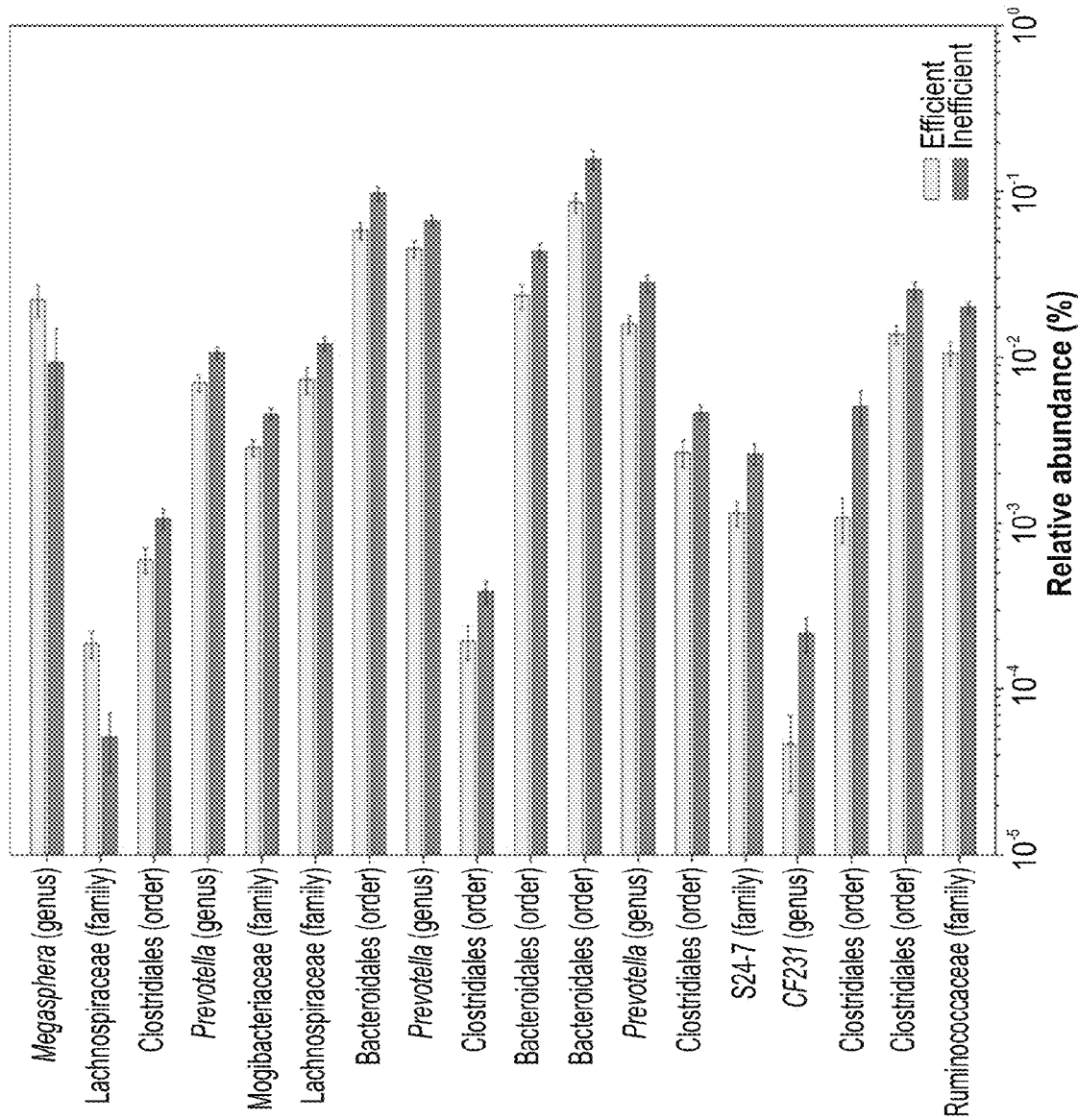

FIG. 18. Relative Abundance of Significantly Different Species. Relative abundance of the 18 species that were found to be significantly different between the two efficiency groups. Data are expressed as mean±SEM.

Figure 19:
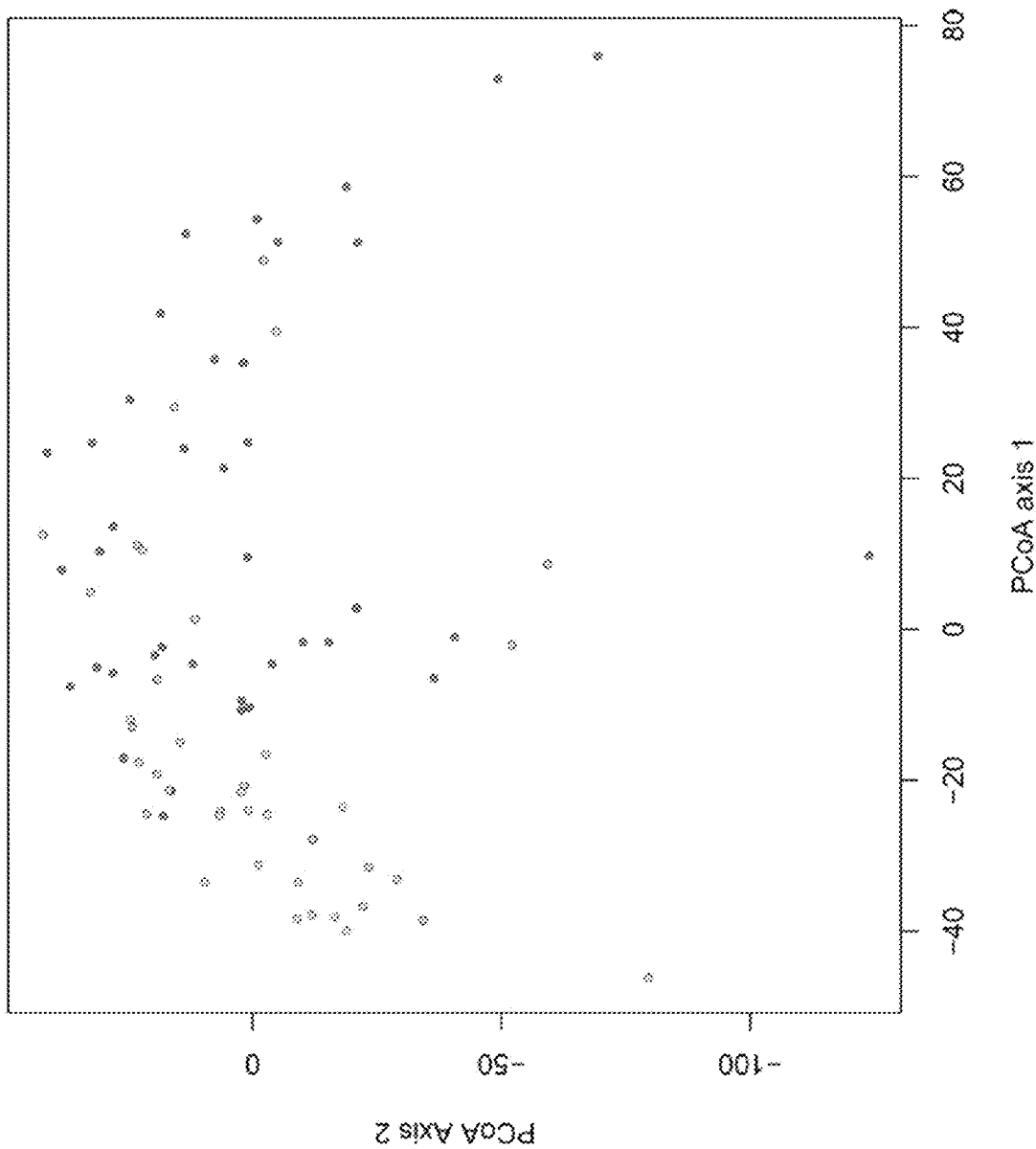

FIG. 19. Principal Component Analysis (PCA) of Genes Enriched in the Two Efficiency Groups—PCA was performed for the efficient and inefficient cows' microbiomes using the 34,166 genes that were significantly different between the two efficiency groups.

Figure 20:
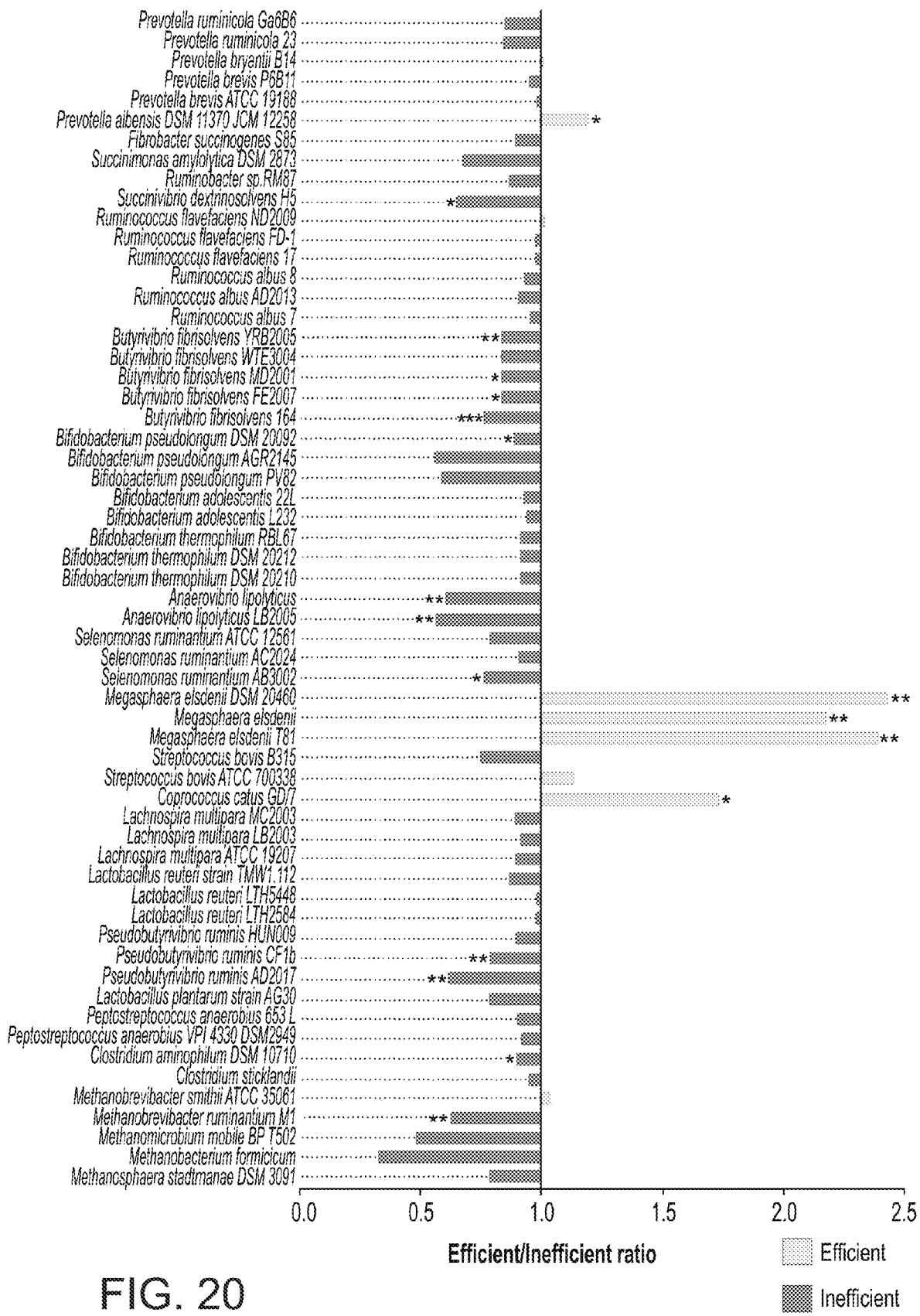

FIG. 20. Read Alignment to Known Rumen Microbial Genomes. Reads from each sample were aligned to sequenced genomes of known rumen microorganisms using the BWA tool. The ratios between recruitment of efficient/inefficient samples to each genome are presented. Data are expressed as mean±SEM. Permutations t test, *$P<0.05$, $P<0.01$, *$P<0.001$.

Figure 21:
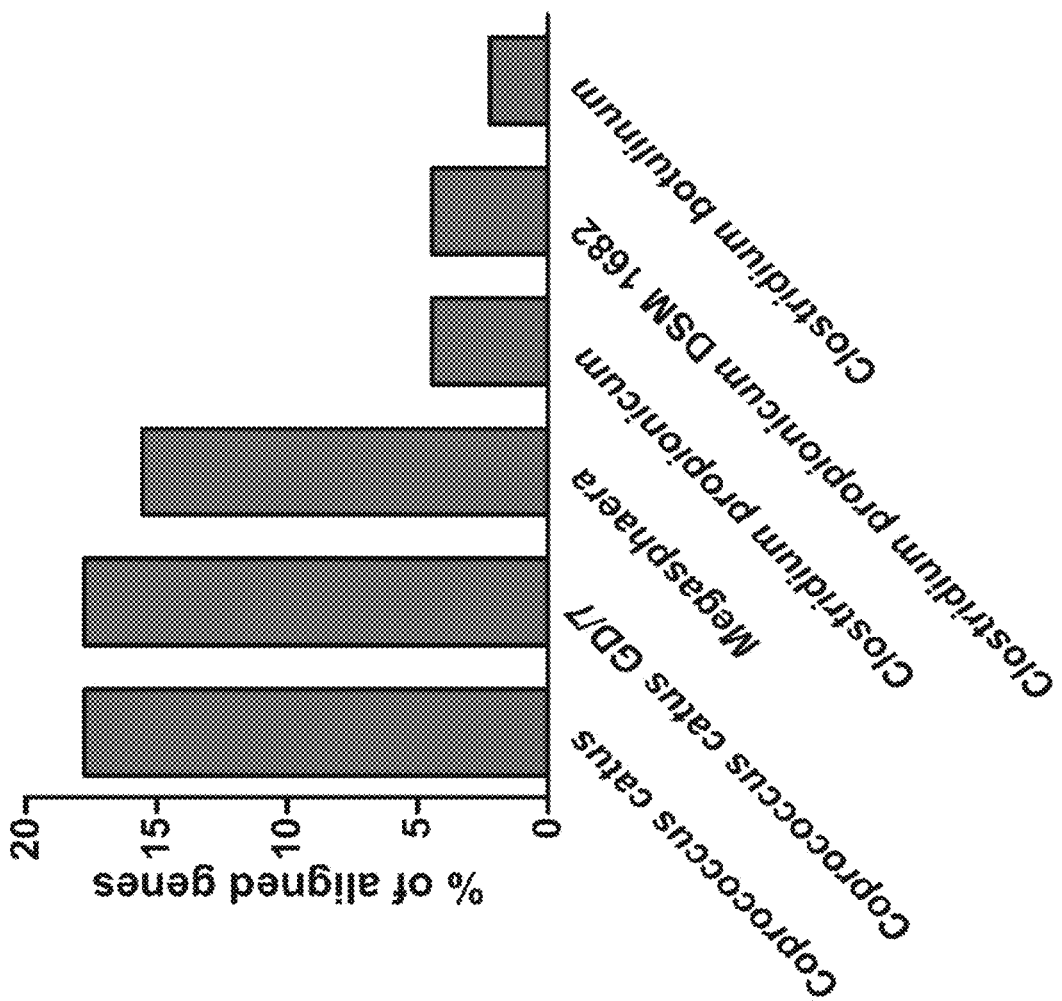

FIG. 21. Acrylate Pathway Distribution in Organisms of the Rumen Microbiome. Reads from all samples were blasted against genes of lactoyl-CoA dehydratase subunits alpha, beta and gamma (Reichardt et al. 2014). Reads that passed a cutoff of 60% identity were gathered and annotated using the NR database. The percentage of each annotation in the overall reads is presented.

DESCRIPTION OF THE PREFERRED EMBODIMENTS

The present invention, in some embodiments thereof, relates to rumen microflora and uses thereof. In one embodiment, the present invention relates to rumen microflora in order to regulate feed efficiency and methane production in ruminating animals.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Ruminants are completely dependent on their microbiota for feed digestion and consequently, their viability. The present inventors hypothesized that a connection between the composition and abundance of resident rumen bacterial taxa and the physiological parameters of the host may exist.

Feed efficiency was measured in 146 milking cows and analyses of the taxonomic composition, gene content, microbial activity and metabolomic composition was performed on the rumen microbiomes from the 78 most extreme animals. Lower richness of microbiome gene content and taxa was tightly linked to higher feed-efficiency. Microbiome genes and species accurately predicted the animals' feed-efficiency phenotype. Specific enrichment of microbes and metabolic pathways in each of these microbiome groups resulted in better energy and carbon channeling to the animal, while lowering methane emissions to the atmosphere. This ecological and mechanistic understanding of the rumen microbiome could lead to an increase in available food resources and environmentally friendly livestock agriculture.

Thus, according to a first aspect of the present invention there is provided a method of determining the feed efficiency or methane production of a ruminating animal comprising analyzing the number and/or diversity of a bacterial taxon of a microbiome of the animal, wherein a number and/or diversity of the taxon below a predetermined level is indicative of an animal having a high feed efficiency and low methane production.

As used herein, the term "feed efficiency" refers to the ability of the animal to extract energy from its food. The feed efficiency is the difference between an animal's actual feed intake and its predicted feed intake based on its production level and body weight. Thus, an animal with "a high" feed efficiency is one that produces more milk or weighs more that what is predicted based on its feed intake. An animal with "a negative" feed efficiency is one that produces less milk or weighs less than what is predicted based on its feed intake. In one embodiment, the energy efficiency is measured using the residual feed intake (RFI) method (Koch et al., 1963) and may be calculated according to national Research Council 2001 formulas. The expected RFI values for each cow may be calculated based on a multiple regression equation.

According to one embodiment, an animal can be classified as having a low RFI (or high feed efficiency) when it has at least 0.05 standard deviations below the average RFI of the herd (with a herd being at least 15 animals).

According to one embodiment, an animal can be classified as having a low RFI (or high energy efficiency) when it has at least 0.05 standard deviations below the average RFI of the herd (with a herd being at least 15 animals).

According to one embodiment, an animal can be classified as having a low RFI (or high energy efficiency) when it has at least 1 standard deviations below the average RFI of the herd (with a herd being at least 15 animals).

According to one embodiment, an animal can be classified as having a low RFI (or high energy efficiency) when it has at least 2 standard deviations below the average RFI of the herd, with a herd being at least 15 animals.

According to one embodiment, an animal can be classified as having a low RFI (or high energy efficiency) when it has at least 3 standard deviations below the average RFI of the herd, with a herd being at least 15 animals.

According to one embodiment, an animal can be classified as having a low RFI (or high energy efficiency) when it has at least 4 standard deviations below the average RFI of the herd (with a herd being at least 15 animals).

According to one embodiment, an animal can be classified as having a low RFI (or high energy efficiency) when it has at least 5 standard deviations below the average RFI of the herd (with a herd being at least 15 animals).

According to one embodiment, an animal can be classified as having a low RFI (or high energy efficiency) when it has at least 6 standard deviations below the average RFI of the herd (with a herd being at least 15 animals).

According to one embodiment, an animal can be classified as having a high RFI (or low feed efficiency) when it has at least 0.05 standard deviations above the average RFI of the herd (with a herd being at least 15 animals).

According to one embodiment, an animal can be classified as having a high RFI (or low energy efficiency) when it has at least 0.05 standard deviations above the average RFI of the herd (with a herd being at least 15 animals).

According to one embodiment, an animal can be classified as having a high RFI (or low energy efficiency) when it has at least 1 standard deviations above the average RFI of the herd (with a herd being at least 15 animals).

According to one embodiment, an animal can be classified as having a high RFI (or low energy efficiency) when it has at least 2 standard deviations above the average RFI of the herd, with a herd being at least 15 animals.

According to one embodiment, an animal can be classified as having a high RFI (or low energy efficiency) when it has at least 3 standard deviations above the average RFI of the herd, with a herd being at least 15 animals.

According to one embodiment, an animal can be classified as having a high RFI (or low energy efficiency) when it has at least 4 standard deviations above the average RFI of the herd (with a herd being at least 15 animals).

According to one embodiment, an animal can be classified as having a high RFI (or low energy efficiency) when it has at least 5 standard deviations below the average RFI of the herd (with a herd being at least 15 animals).

According to one embodiment, an animal can be classified as having a high RFI (or low energy efficiency) when it has at least 6 standard deviations above the average RFI of the herd (with a herd being at least 15 animals).

According to one embodiment, an animal can be classified as having a low RFI (or high energy efficiency) when its dry matter intake (DMI) is less than 1 kg per day than predicted according to its expected food intake (calculated as a function of weight and milk production, as described herein above).

According to one embodiment, an animal can be classified as having a low RFI (or high energy efficiency) when its dry matter intake (DMI) is less than 2 kg per day than predicted according to its expected food intake.

According to one embodiment, an animal can be classified as having a low RFI (or high energy efficiency) when its dry matter intake (DMI) is less than 4 kg per day than predicted according to its expected food intake.

According to one embodiment, an animal can be classified as having a low RFI (or high energy efficiency) when its dry matter intake (DMI) is less than 8 kg per day than predicted according to its expected food intake.

According to one embodiment, an animal can be classified as having a low RFI (or high energy efficiency) when its dry matter intake (DMI) is less than 16 kg per day than predicted according to its expected food intake.

According to one embodiment, an animal can be classified as having a low RFI (or high energy efficiency) when its dry matter intake (DMI) is less than 32 kg per day than predicted according to its expected food intake.

According to one embodiment, an animal can be classified as having a low RFI (or high energy efficiency) when it produces 1.5 fold the amount of milk or weighs 1.5 fold the weight than predicted according to its feed intake.

According to one embodiment, an animal can be classified as having a low RFI (or high energy efficiency) when it produces 2 fold the amount of milk or weighs 2 fold the weight than predicted according to its feed intake.

According to one embodiment, an animal can be classified as having a low RFI (or high energy efficiency) when it produces 2.5 fold the amount of milk or weighs 2.5 fold the weight than predicted according to its feed intake.

According to one embodiment, an animal can be classified as having a low RFI (or high energy efficiency) when it produces 3 fold the amount of milk or weighs 3 fold the weight than predicted according to its feed intake.

According to one embodiment, an animal can be classified as having a low RFI (or high energy efficiency) when it produces 3.5 fold the amount of milk or weighs 3.5 fold the weight than predicted according to its feed intake.

According to one embodiment, an animal can be classified as having a low RFI (or high energy efficiency) when it produces 4 fold the amount of milk or weighs 4 fold the weight than predicted according to its feed intake.

According to one embodiment, an animal can be classified as having a low RFI (or high energy efficiency) when it produces 4.5 fold the amount of milk or weighs 4.5 fold the weight than predicted according to its feed intake.

According to one embodiment, an animal can be classified as having a low RFI (or high energy efficiency) when it produces 5 fold the amount of milk or weighs 5 fold the weight than predicted according to its feed intake.

The term "methane production" refers to an amount of methane emitted by the animals per se or produced by the microbiome. It may be measured in units of g per day or g per kg of dry matter intake.

According to one embodiment, an animal can be classified as "high methane producer" when it has at least 0.05 standard deviations above the average methane production of the herd.

According to one embodiment, an animal can be classified as "high methane producer" when it has at least 0.5 standard deviations above the average methane production of the herd.

According to one embodiment, an animal can be classified as "high methane producer" when it has at least 1 standard deviations above the average methane production of the herd.

According to one embodiment, an animal can be classified as "high methane producer" when it has at least 2 standard deviations above the average methane production of the herd.

According to one embodiment, an animal can be classified as "high methane producer" when it has at least 3 standard deviations above the average methane production of the herd.

According to one embodiment, an animal can be classified as "high methane producer" when it has at least 4 standard deviations above the average methane production of the herd.

According to one embodiment, an animal can be classified as "high methane producer" when it has at least 5 standard deviations above the average methane production of the herd.

According to one embodiment, an animal can be classified as "high methane producer" when it has at least 6 standard deviations above the average methane production of the herd.

The term "low methane production" refers to an amount less than 100 g per day or 10 g per kg per dry matter intake produced in the microbiome (e.g. rumen microbiome/fecal microbiome) of the animal.

According to one embodiment, an animal can be classified as "low methane producer" when it has at least 0.05 standard deviations below the average methane production of the herd.

According to one embodiment, an animal can be classified as "low methane producer" when it has at least 0.5 standard deviations below the average methane production of the herd.

According to one embodiment, an animal can be classified as "low methane producer" when it has at least 1 standard deviations below the average methane production of the herd.

According to one embodiment, an animal can be classified as "low methane producer" when it has at least 2 standard deviations below the average methane production of the herd.

According to one embodiment, an animal can be classified as "low methane producer" when it has at least 3 standard deviations below the average methane production of the herd.

According to one embodiment, an animal can be classified as "low methane producer" when it has at least 4 standard deviations below the average methane production of the herd.

According to one embodiment, an animal can be classified as "low methane producer" when it has at least 5 standard deviations below the average methane production of the herd.

According to one embodiment, an animal can be classified as "low methane producer" when it has at least 6 standard deviations below the average methane production of the herd.

Ruminating animals contemplated by the present invention include for example cattle (e.g. cows), goats, sheep, giraffes, American Bison, European Bison, yaks, water buffalo, deer, camels, alpacas, llamas, wildebeest, antelope, pronghorn, and nilgai.

According to a particular embodiment, the ruminating animal is a cow.

The present invention contemplates determining feed efficiency in ruminating animals of all ages. According to a particular embodiment, the animals whose phenotype is altered are newborns, typically not more than one day old. According to another embodiment, the animals are not more than two days old. According to another embodiment, the animals are not more than three days old. According to another embodiment, the animals are not more than 1 week old. According to another embodiment, the animals are not more than 2 week old. According to another embodiment, the animals are not more than 1 month old. According to another embodiment, the animals are not more than 3 months old. According to still another embodiment, the animals are adult.

The term "microbiome" as used herein, refers to the totality of microbes (bacteria, fungi, protists), their genetic elements (genomes) in a defined environment.

According to a particular embodiment, the microbiome is a rumen microbiome.

According to another embodiment, the microbiome is derived from a healthy animal (i.e. the microbiome is a non-pathogenic microbiome).

A microbiota sample comprises a sample of microbes and or components or products thereof from a microbiome.

In some embodiments, a microbiota sample is collected by any means that allows recovery of microbes or components or products thereof of a microbiome and is appropriate to the relevant microbiome source e.g. rumen.

Rumen may be collected using methods known in the art and include for example use of a stomach tube with a rumen vacuum sampler. Typically rumen is collected after feeding.

In some embodiments, in lieu of analyzing a rumen sample, a fecal sample is used which mirrors the microbiome of the rumen. Thus, in this embodiment, a fecal microbiome is analyzed.

According to one embodiment of this aspect of the present invention, the number of bacterial taxa in the microbiota sample are analyzed and/or the number of genes in the microbiota sample are analyzed. This analysis corresponds to the richness of the microbiota sample.

Optionally, the abundance of each of the taxa/genes are also analyzed so as to obtain a measure of the diversity or dominance of the sample.

Taxon diversity consists of two components: taxon (e.g. species) richness and tax (e.g. species) evenness. Species richness is a simple count of species, whereas species evenness quantifies how equal the abundances of the species are Dominance: Measures the probability that two individuals randomly selected from a sample will belong to the same taxon, it ranges from 0 (all taxon are equally present) to 1 (one taxon dominates the community completely).

Dominance: $sum((n_i/n)^2)$ where $n_i$ is number of individuals of taxon i.

The rumen microflora may be analyzed on a quantitative level and/or a qualitative level.

Methods of quantifying levels of genes and microbes (e.g. bacteria) of various taxa are described herein below.

In some embodiments, determining a level or set of levels of one or more types of microbes or components or products thereof comprises determining a level or set of levels of one or more DNA sequences. In some embodiments, one or more DNA sequences comprise any DNA sequence that can be used to differentiate between different microbial types. In certain embodiments, one or more DNA sequences comprise 16S rRNA gene sequences. In certain embodiments, one or more DNA sequences comprise 18S rRNA gene sequences. In some embodiments, 1, 2, 3, 4, 5, 10, 15, 20, 25, 50, 100, 1,000, 5,000 or more sequences are amplified.

Taxonomy assignment of species may be performed using a suitable computer program (e.g. BLAST) against the appropriate reference database (e.g. 16S rRNA reference database).

In determining whether a nucleic acid or protein is substantially homologous or shares a certain percentage of sequence identity with a sequence of the invention, sequence similarity may be defined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed.

According to one embodiment, in order to classify a microbe as belonging to a particular genus, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular genus. According to a particular embodiment, the sequence homology is at least 95%.

According to another embodiment, in order to classify a microbe as belonging to a particular species, it must comprise at least 90% sequence homology, at least 91% sequence homology, at least 92% sequence homology, at least 93% sequence homology, at least 94% sequence homology, at least 95% sequence homology, at least 96% sequence homology, at least 97% sequence homology, at least 98% sequence homology, at least 99% sequence homology to a reference microbe known to belong to the particular species. According to a particular embodiment, the sequence homology is at least 97%.

In some embodiments, a microbiota sample is directly assayed for a level or set of levels of one or more DNA sequences. In some embodiments, DNA is isolated from a microbiota sample and isolated DNA is assayed for a level or set of levels of one or more DNA sequences. Methods of isolating microbial DNA are well known in the art. Examples include but are not limited to phenol-chloroform extraction and a wide variety of commercially available kits, including QJAamp DNA Stool Mini Kit (Qiagen, Valencia, Calif.).

In some embodiments, a level or set of levels of one or more DNA sequences is determined by amplifying DNA sequences using PCR (e.g., standard PCR, semi-quantitative, or quantitative PCR). In some embodiments, a level or set of levels of one or more DNA sequences is determined by amplifying DNA sequences using quantitative PCR. These and other basic DNA amplification procedures are well known to practitioners in the art and are described in Ausebel et al. (Ausubel F M, Brent R, Kingston R E, Moore D D, Seidman J G, Smith J A, Struhl K (eds). 1998. Current Protocols in Molecular Biology. Wiley: New York).

In some embodiments, DNA sequences are amplified using primers specific for one or more sequence that differentiate(s) individual microbial types from other, different microbial types. In some embodiments, 16S rRNA gene sequences or fragments thereof are amplified using primers specific for 16S rRNA gene sequences. In some embodiments, 18S DNA sequences are amplified using primers specific for 18S DNA sequences.

In some embodiments, a level or set of levels of one or more 16S rRNA gene sequences is determined using phylochip technology. Use of phylochips is well known in the art and is described in Hazen et al. ("Deep-sea oil plume enriches indigenous oil-degrading bacteria." Science, 330, 204-208, 2010), the entirety of which is incorporated by reference. Briefly, 16S rRNA genes sequences are amplified and labeled from DNA extracted from a microbiota sample. Amplified DNA is then hybridized to an array containing probes for microbial 16S rRNA genes. Level of binding to each probe is then quantified providing a sample level of microbial type corresponding to 16S rRNA gene sequence probed. In some embodiments, phylochip analysis is performed by a commercial vendor. Examples include but are not limited to Second Genome Inc. (San Francisco, Calif.).

In some embodiments, determining a level or set of levels of one or more types of microbes or components or products thereof comprises determining a level or set of levels of one or more microbial RNA molecules (e.g., transcripts). Methods of quantifying levels of RNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York).

In some embodiments, determining a level or set of levels of one or more types of microbes or components or products thereof comprises determining a level or set of levels of one or more microbial proteins. Methods of quantifying protein levels are well known in the art and include but are not limited to western analysis and mass spectrometry. These and all other basic protein detection procedures are described in Ausebel et al. (Ausubel F M, Brent R, Kingston R E, Moore D D, Seidman J G, Smith J A, Struhl K (eds). 1998. Current Protocols in Molecular Biology. Wiley: New York). In some embodiments, determining a level or set of levels of one or more types of microbes or components or products thereof comprises determining a level or set of levels of one or more microbial metabolites. In some embodiments, levels of metabolites are determined by mass spectrometry. In some embodiments, levels of metabolites are determined by nuclear magnetic resonance spectroscopy. In some embodiments, levels of metabolites are determined by enzyme-linked immunosorbent assay (ELISA). In some embodiments, levels of metabolites are determined by colorimetry. In some embodiments, levels of metabolites are determined by spectrophotometry.

In some embodiments, what is determined is the distribution of microbial families within the microbiome. However, characterization may be carried to more detailed levels, e.g. to the level of genus and/or species, and/or to the level of strain or variation (e.g. variants) within a species, if desired (including the presence or absence of various genetic elements such as genes, the presence or absence of plasmids, etc.). Alternatively, higher taxanomic designations can be used such as Phyla, Class, or Order. The objective is to identify which microbes (usually bacteria, but also optionally fungi (e.g. yeasts), protists, etc.) are present in the sample from the ruminating animal and the relative distributions of those microbes, e.g. expressed as a percentage of the total number of microbes that are present, thereby establishing a micro floral pattern or signature for the animal being tested.

In other embodiments of the invention, when many taxa are being considered, the overall pattern of microflora is assessed, i.e. not only are particular taxa identified, but the percentage of each constituent taxon is taken in account, in comparison to all taxa that are detected and, usually, or optionally, to each other. Those of skill in the art will recognize that many possible ways of expressing or compiling such data exist, all of which are encompassed by the present invention. For example, a "pie chart" format may be used to depict a microfloral signature; or the relationships may be expressed numerically or graphically as ratios or percentages of all taxa detected, etc. Further, the data may be manipulated so that only selected subsets of the taxa are considered (e.g. key indicators with strong positive correlations). Data may be expressed, e.g. as a percentage of the total number of microbes detected, or as a weight percentage, etc.

In one embodiment, a nonparametric multivariate test such as Metastats, Analysis of Similarity, Principle Component Analysis, Non-Parametric MANOVA (Kruskal-Wallace) etc. can be used to associate a microbiome signature with a particular phenotype with a statistical significant (P value) of less than 0.05. Such tests are known in the art and are described, for example, by White J R, Nagarajan N, Pop M (2009) Statistical Methods for Detecting Differentially Abundant Features in Clinical Metagenomic Samples. PLoS Computational Biology 5(4): 1-11; and Clarke K R, Gorley R N (2001) PRIMER v5: User Manual and Tutorial, PRIMER-E Ltd. Plymouth Marine Laboratory, UK.

In other embodiments, phylogenetic methods such as Unifrac can be used to associate microbiome signature with a particular phenotype with a statistically significant (P value) of less than 0.05. See, for example, Lozupone C, Knight R (2005) UniFrac: a new phylogenetic method for comparing microbial communities. Appl Environ Microbiol 71:8228-8235.

In other embodiments, support vector machines can be used to associate microbiome signature with a particular phenotype with sufficiently high classification measure (F-measure) and appropriate sensitivity and specificity that is accepted in the state of the art. See, for example, Yang C, Mills D, Mathee K, Wang Y, Jayachandran K, Sikaroodi M, Gillevet P, Entry J, Narasimhan G (2006). An ecoinformatics tool for microbial community studies: Supervised classification of Amplicon Length Heterogeneity (ALH) profiles of 16S rRNA. Journal of Microbiological Methods 65(1):49-62.

In other embodiments, correlation network and correlation difference network methods can be used to associate microbiome signature with a particular phenotype with a statistical significant (P value) of less than 0.05. See, for example, Weckwerth W, Loureiro M E, Wenzel, Fiehn O (2004) Differential metabolic networks unravel the effects of silent plant phenotypes. PNAS 101(20):7809-7814.

As mentioned, when the number of a bacterial taxon of a microbiome of the ruminating animal is below a predetermined level, it is indicative of an animal having a high feed efficiency and low methane production.

The term "indicative" as used herein, refers to the probability of being associated with a particular phenotype being above 50%, 60%, 70%, 80%, 90% or higher.

The number of bacterial taxon may be analyzed at the level of species, genus, family, order, class or phylum.

In addition, when the number of genes of a microbiome of the ruminating animal is below a predetermined level, it is indicative of an animal having a high feed efficiency and low methane production.

In one embodiment, when the number of bacterial species present in the microbiome sample is below 6000, it is indicative that the animal has a high feed efficiency.

In another embodiment, when the number of bacterial species present in the microbiome sample is below 5000, it is indicative that the animal has a high feed efficiency.

In still another embodiment, when the number of bacterial species is below 4000, it is indicative that the animal has a high feed efficiency.

In one embodiment, when the number of bacterial genes present in the microbiome sample is below $4 \times 10^6$, it is indicative that the animal has a high feed efficiency.

In another embodiment, when the number of bacterial genes present in the microbiome sample is below $3.5 \times 10^6$, it is indicative that the animal has a high feed efficiency.

In another embodiment, when the number of bacterial genera present in the microbiome sample is below 120, it is indicative that the animal has a high feed efficiency.

In still another embodiment, when the number of bacterial genera is below 100, it is indicative that the animal has a high feed efficiency.

In another embodiment, when the number of bacterial families present in the microbiome sample is below 70, it is indicative that the animal has a high feed efficiency.

In still another embodiment, when the number of bacterial families is below 60, it is indicative that the animal has a high feed efficiency.

In still another embodiment, when the number of bacterial orders is below 35, it is indicative that the animal has a high feed efficiency.

In still another embodiment, when the number of bacterial classes is below 25, it is indicative that the animal has a high feed efficiency.

In still another embodiment, when the number of bacterial phyla is below 14, it is indicative that the animal has a high feed efficiency.

Furthermore, when the diversity of a taxon (e.g. species) and/or genes are below a predetermined level, it is indicative of an animal having a high feed efficiency and low methane production.

Still further, when the dominance of a taxon (e.g. species) and/or genes is above a predetermined level, it is indicative of an animal having a high feed efficiency and low methane production.

Using sophisticated sequencing and screening techniques, the present inventors have uncovered bacterial populations that may be used to predict parameters including feed efficiency (e.g. as measured by RFI), which is inversely proportional to rumen microbiome methane production.

Thus, according to another aspect of the present invention there is provided a method of determining feed efficiency and/or methane production in a ruminating animal comprising quantifying at least one bacterial species as set forth in Tables 4 and 5 in a microbiome of the animal, wherein when the level of at least one bacterial species in Table 4 is above a predetermined level it is indicative of a high feed efficiency or a low methane production and when the level of at least one bacterial species set forth in Table 5 is below a predetermined level, it is indicative of a high feed efficiency or a low methane production.

Tables 4 and 5 appear at the end of the Examples section herein below.

It will be appreciated that, in some cases, particular strains of bacteria appear in Tables 4 and 5. However, the present invention contemplates analyzing all strains of the species to which it belongs. Mentioning of a particular strain should not be limiting in any way.

Thus for example, in the case of *Methanobrevibacter smithii* ATCC 35061, although only the strain number appears in Table 4, the present inventors contemplate analyzing any strain of *Methanobrevibacter smithii* species.

When orders higher than species are recited in Tables 4 and 5, the 16S identifier is recited, so that the exact species should be considered to be fully disclosed.

The predetermined level may be ascertained using control samples derived from animals which have been pre-classified as a high methane producer/low methane producer or high RFI/low RFI. Thus for example when the amount of a bacterial species from Table 4 is at least 1.5 fold, 2 fold, 3 fold, 4 fold, 5 fold or higher than the amount which is present in a microbiome of an animal pre-classified as an average RFI animal, then the animal can be classified as a low RFI (high energy efficiency) animal. When the amount of a bacterial species from Table 5 is at least 1.5 fold, 2 fold, 3 fold, 4 fold, 5 fold or lower than the amount which is present in a microbiome of an animal pre-classified as an average RFI animal, then the animal can be classified as a high RFI animal (low energy efficiency).

It will be appreciated that the classification need not be limited to a binary classification (high/low) since the present inventors have shown that the amount of the bacteria is correlative with the RFI. Thus, the animal may be scored using many non-binary systems as well.

Methods of quantifying level of bacterial species are known to those skilled in the art, including sequencing methods and quantification of species specific genes as described herein above.

When comparing genes and taxonomic profiles between the microbiomes of efficient and inefficient animals, the present inventors found that genes belonging to the acrylate pathway were enriched in the efficient animals when compared to the inefficient animals.

Thus, according to another aspect of the present invention the bacterial species that is analyzed is one that utilizes the acrylate pathway.

As used herein, the phrase "bacteria which utilizes the acrylate pathway" refers to a bacteria that is capable of generating propionic acid from lactic acid. The bacteria thus expresses genes encoding enzymes having the following EC numbers: EC 1.3.8.7, 2.8.3.1 and 4.2.1.54.

Exemplary species which utilize the acrylate pathway include, but are not limited to *Megasphaera elsdenii, Coprococcus catus, Clostridium propionicum* and *Clostridium botulinum*.

The present inventors contemplate classification of animals based on the level of at least one of, at least two of, at least three, at least four, at least 5, at least 6, at least 7, at least 8, at least 9, at least 10, at least 15, at least 20, at least 30, at least 40, at least 50, at least 100 of or all of the species disclosed in Tables 4 and 5.

According to a particular embodiment, a plurality of bacterial species are analyzed so as to obtain a bacterial signature. The signature is then compared with the signature derived from an animal which has already been classified according to its feed efficiency/methane production. For example, if the test signature is statistically significantly similar to the control signature known to be a high methane producer, that animal can then be classified as a high methane producer. If the test signature is statistically significantly similar to the control signature known to be a low methane producer, that animal can then be classified as a low methane producer. If the test signature is statistically significantly dissimilar to the control signature known to be a low methane producer, that animal can then be classified as a high methane producer. If the test signature is statistically significantly dissimilar to the control signature known to be a high methane producer, that animal can then be classified as a low methane producer.

According to one embodiment of this aspect of the present invention two microbiome signatures can be have a statistically significant similar signature when they comprise at least 50% of the same species, at least 60% of the same species, at least 70% of the same species, at least 80% of the same species, at least 90% of the same species, at least 91% of the same species, at least 92% of the same species, at least 93% of the same species, at least 94% of the same species, at least 95% of the same species, at least 96% of the same species, at least 97% of the same species, at least 98% of the same species, at least 99% of the same species or 100% of the same species.

Additionally, or alternatively, microbiomes may have a statistically significant similar signature when the quantity (e.g. occurrence) in the microbiome of at least one of the bacterial species set forth in Tables 4 and 5 is identical. According to another embodiment, microbiomes may have a statistically significant similar signature when the relative ratio in the microbiome of at least 10% of the bacteria set forth in Tables 4 and 5 are identical. According to another embodiment, microbiomes may have a statistically significant similar signature when the relative ratio in the microbiome of at least 20% of the bacteria set forth in Tables 4 and 5 are identical. According to another embodiment, microbiomes may have a statistically significant similar signature when the relative ratio in the microbiome of at least 30% of the bacteria set forth in Tables 4 and 5 identical. According to another embodiment, microbiomes may have a statistically significant similar signature when the relative ratio in the microbiome of at least 40% of the bacteria set forth in Tables 4 and 5 are identical. According to another embodiment, microbiomes may have a statistically significant similar signature when the relative ratio in the microbiome of at least 50% of the bacteria set forth in Tables 4 and 5 are identical. According to another embodiment, microbiomes may have a statistically significant similar signature when the relative ratio in the microbiome of at least 60% of the bacteria set forth in Tables 4 and 5 are identical. According to another embodiment, microbiomes may have a statistically significant similar signature when the relative ratio in the microbiome of at least 70% of the bacteria set forth in Tables 4 and 5 are identical. According to another embodiment, microbiomes may have a statistically significant similar signature when the relative ratio in the microbiome of at least 80% of the bacteria set forth in Tables 4 and 5 are identical. According to another embodiment, microbiomes may have a statistically significant similar signature when the relative ratio in the microbiome of at least 90% of the bacteria set forth in Tables 4 and 5 are identical. Thus, the fractional percentage of microbes (e.g. relative amount, ratio, distribution, frequency, percentage, etc.) of the total may be statistically similar.

The present inventors have further noted that analysis of the full genus of *Megasphaera* can be used to predict methane emission and/or RFI.

Thus according to yet another aspect of the present invention there is provided a method of determining feed efficiency and/or methane production in a ruminating animal comprising quantifying at least one bacterial species of the genus *Megasphaera* in a microbiome of the animal, wherein when the level of the at least one bacterial species is above a predetermined level it is indicative of a high feed efficiency or a low methane production.

The method of this aspect of the present invention can be carried out using methods known in the art for quantifying bacteria (as detailed herein above) or by analyzing the DNA sequences, as discussed herein above.

The predetermined level of this aspect of the present invention can be determined as described herein above.

PCR kits for detection of *Megasphaera elsdenii* are disclosed in Advanced kit handbook HB 10.03.07—Quantification of *Megasphaera cerevisiae/Megasphaera elsdenii* genomes. 7.

As mentioned, as well as measuring bacteria and genes present in the microbiome, the present inventors have also shown that measuring metabolites present in the microbiome (i.e. the metabolome) can also provide an indication as to the status of the feed efficiency and microbiome methane production of the ruminating animal.

More specifically, the present inventors have shown that the levels of short chain fatty acids in the metabolome of the ruminating animal can be used to gauge the feed efficiency and methane production of the animals.

In one embodiment, the metabolome of the rumen is measured. In another embodiment, the metabolome of the feces of the animal is measured.

As used herein, a "metabolite" is an intermediate or product of metabolism. The term metabolite is generally restricted to small molecules and does not include polymeric compounds such as DNA or proteins greater than 100 amino acids in length. A metabolite may serve as a substrate for an enzyme of a metabolic pathway, an intermediate of such a pathway or the product obtained by the metabolic pathway.

In one embodiment, no more than 5 metabolites are analyzed. In another embodiment, no more than 10 metabolites are measured. In still another embodiment, no more than 15 metabolites are measured. In still another embodiment, no more than 20 metabolites are measured. In still another embodiment, no more than 30 metabolites are measured. In still another embodiment, no more than 40 metabolites are measured. In still another embodiment, no more than 50 metabolites are measured. In still another embodiment, no more than 60 metabolites are measured. In still another embodiment, no more than 100 metabolites are measured.

According to a particular embodiment, the metabolite is one that alters the composition or function of the microbiome.

In preferred embodiments, metabolites include but are not limited to sugars, organic acids, amino acids, fatty acids, hormones, vitamins, as well as ionic fragments thereof. In another embodiment, the metabolite is an oligopeptides (less than about 100 amino acids in length).

In particular, the metabolites are less than about 3000 Daltons in molecular weight, and more particularly from about 50 to about 3000 Daltons.

Preferably, the metabolite is present in the microbes of the microbiome or secreted from the microbes of the microbiome.

The metabolite of this aspect of the present invention may be a primary metabolite (i.e. essential to the microbe for growth) or a secondary metabolite (one that does not play a role in growth, development or reproduction, and is formed during the end or near the stationary phase of growth.

Representative examples of metabolic pathways in which the metabolites of the present invention are involved include, without limitation, citric acid cycle, respiratory chain, photosynthesis, photorespiration, glycolysis, gluconeogenesis, hexose monophosphate pathway, oxidative pentose phosphate pathway, acrylate pathway, succinate pathway, methanogenesis pathway, propanediol pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including, e.g., flavonoids and isoflavonoids), isoprenoids (including, e.g., terpenes, sterols, steroids, carotenoids, xanthophylls), carbohydrates, phenylpropanoids and derivatives, alkaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs.

According to a particular embodiment, the metabolite is a short chain fatty acid (e.g. selected from the group consisting of proprionate, butyrate, valerate and isovalerate).

According to this embodiment, when at least one of, at least two of, at least three of, or all of proprionate, butyrate, valerate and isovalerate are above a predetermined level, it is indicative that the animal has a high feed efficiency and a low methane production.

The present inventors have further found that measurement of the total number of short chain fatty acids (SCFAs) in the metabolome of the animal can be used to gauge feed efficiency. Thus, when the amount of all the SCFAs is above a predetermined level (e.g. 0.05 ppm), it is indicative of the animal having a high feed efficiency and a low methane production.

Furthermore, when the ratio of proprionate: acetate in the metabolome of the animal is higher than a predetermined amount (e.g. 1.1 or 1.2), it is indicative of the animal having a high feed efficiency and a low methane production.

In one embodiment, metabolites are identified using a physical separation method.

The term "physical separation method" as used herein refers to any method known to those with skill in the art sufficient to produce a profile of changes and differences in small molecules produced in hSLCs, contacted with a toxic, teratogenic or test chemical compound according to the methods of this invention. In a preferred embodiment, physical separation methods permit detection of cellular metabolites including but not limited to sugars, organic acids, amino acids, fatty acids, hormones, vitamins, and oligopeptides, as well as ionic fragments thereof and low molecular weight compounds (preferably with a molecular weight less than 3000 Daltons, and more particularly between 50 and 3000 Daltons). For example, mass spectrometry can be used. In particular embodiments, this analysis is performed by liquid chromatography/electrospray ionization time of flight mass spectrometry (LC/ESI-TOF-MS), however it will be understood that metabolites as set forth herein can be detected using alternative spectrometry methods or other methods known in the art for analyzing these types of compounds in this size range.

Certain metabolites can be identified by, for example, gene expression analysis, including real-time PCR, RT-PCR, Northern analysis, and in situ hybridization.

In addition, metabolites can be identified using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry (e.g., MS/MS, MS/MS/MS, ESI-MS/MS etc.), secondary ion mass spectrometry (SIMS), or ion mobility spectrometry (e.g. GC-IMS, IMS-MS, LC-IMS, LC-IMS-MS etc.).

Mass spectrometry methods are well known in the art and have been used to quantify and/or identify biomolecules, such as proteins and other cellular metabolites (see, e.g., Li et al., 2000; Rowley et al., 2000; and Kuster and Mann, 1998).

In certain embodiments, a gas phase ion spectrophotometer is used. In other embodiments, laser-desorption/ionization mass spectrometry is used to identify metabolites. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI").

In MALDI, the metabolite is mixed with a solution containing a matrix, and a drop of the liquid is placed on the surface of a substrate. The matrix solution then co-crystallizes with the biomarkers. The substrate is inserted into the mass spectrometer. Laser energy is directed to the substrate surface where it desorbs and ionizes the proteins without significantly fragmenting them. However, MALDI has limitations as an analytical tool. It does not provide means for fractionating the biological fluid, and the matrix material can interfere with detection, especially for low molecular weight analytes.

In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the biomarker of interest and that contain a photolytic bond that is broken upon application of the laser. In each of these methods, the derivatizing agent generally is localized to a specific location on the substrate surface where the sample is applied. The two methods can be combined by, for example, using a SELDI affinity surface to capture an analyte (e.g. biomarker) and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

In some embodiments, the data from mass spectrometry is represented as a mass chromatogram. A "mass chromatogram" is a representation of mass spectrometry data as a chromatogram, where the x-axis represents time and the y-axis represents signal intensity. In one aspect the mass chromatogram is a total ion current (TIC) chromatogram. In another aspect, the mass chromatogram is a base peak chromatogram. In other embodiments, the mass chromatogram is a selected ion monitoring (SIM) chromatogram. In yet another embodiment, the mass chromatogram is a selected reaction monitoring (SRM) chromatogram. In one embodiment, the mass chromatogram is an extracted ion chromatogram (EIC).

In an EIC, a single feature is monitored throughout the entire run. The total intensity or base peak intensity within a mass tolerance window around a particular analyte's mass-to-charge ratio is plotted at every point in the analysis. The size of the mass tolerance window typically depends on the mass accuracy and mass resolution of the instrument collecting the data. As used herein, the term "feature" refers to a single small metabolite, or a fragment of a metabolite. In some embodiments, the term feature may also include noise upon further investigation.

Detection of the presence of a metabolite will typically involve detection of signal intensity. This, in turn, can reflect the quantity and character of a biomarker bound to the substrate. For example, in certain embodiments, the signal strength of peak values from spectra of a first sample and a second sample can be compared (e.g., visually, by computer analysis etc.) to determine the relative amounts of particular metabolites. Software programs such as the Biomarker Wizard program (Ciphergen Biosystems, Inc., Fremont, Calif.) can be used to aid in analyzing mass spectra. The mass spectrometers and their techniques are well known.

A person skilled in the art understands that any of the components of a mass spectrometer, e.g., desorption source, mass analyzer, detect, etc., and varied sample preparations can be combined with other suitable components or preparations described herein, or to those known in the art. For example, in some embodiments a control sample may contain heavy atoms, e.g. $^{13}C$, thereby permitting the test sample to be mixed with the known control sample in the same mass spectrometry run. Good stable isotopic labeling is included.

In one embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In one embodiment of the invention, levels of metabolites are detected by MALDI-TOF mass spectrometry.

Methods of detecting metabolites also include the use of surface plasmon resonance (SPR). The SPR biosensing technology has been combined with MALDI-TOF mass spectrometry for the desorption and identification of metabolites.

Data for statistical analysis can be extracted from chromatograms (spectra of mass signals) using softwares for statistical methods known in the art. "Statistics" is the science of making effective use of numerical data relating to groups of individuals or experiments. Methods for statistical analysis are well-known in the art.

In one embodiment a computer is used for statistical analysis.

In one embodiment, the Agilent MassProfiler or MassProfilerProfessional software is used for statistical analysis. In another embodiment, the Agilent MassHunter software Qual software is used for statistical analysis. In other embodiments, alternative statistical analysis methods can be used. Such other statistical methods include the Analysis of Variance (ANOVA) test, Chi-square test, Correlation test, Factor analysis test, Mann-Whitney U test, Mean square weighted derivation (MSWD), Pearson product-moment correlation coefficient, Regression analysis, Spearman's rank correlation coefficient, Student's T test, Welch's T-test, Tukey's test, and Time series analysis.

In different embodiments signals from mass spectrometry can be transformed in different ways to improve the performance of the method. Either individual signals or summaries of the distributions of signals (such as mean, median or variance) can be so transformed. Possible transformations include taking the logarithm, taking some positive or negative power, for example the square root or inverse, or taking the arcsin (Myers, Classical and Modern Regression with Applications, 2nd edition, Duxbury Press, 1990).

It will be appreciated that once the animal has been classified with a particular phenotype (e.g. high feed efficiency, low methane producer), it may be selected (e.g.

separated from the rest of the herd) and classified as having that phenotype. According to one embodiment, the animal branded such that it is clear that it comprises this phenotype.

In one embodiment, the animal is selected as being a candidate for breeding. In another embodiment, the animal is selected as being a candidate for meat production. In the case where the animal is found as having a non-desirable phenotype (e.g. low feed efficiency, high methane producer), the animal may be selected as being a candidate for therapy.

Thus, according to another aspect of the present invention there is provided a method of increasing the feed efficiency or decreasing the methane production of a ruminating animal comprising administering to the animal an agent which increases the amount of at least one bacterial species set forth in Table 4 in the rumen microbiome of the animal, thereby increasing the feed efficiency or decreasing the methane production of a ruminating animal. Alternatively, in order to increase feed efficiency (or decrease methane production) an agent may be provided which increases the amount of at least one species of the bacterial genus *Megasphaera*, at least two species of the bacterial genus *Megasphaera*, at least three species of the bacterial genus *Megasphaera*, at least four species of the bacterial genus *Megasphaera*, at least five species of the bacterial genus *Megasphaera*, at least six species of the bacterial genus *Megasphaera*, at least seven species of the bacterial genus *Megasphaera*, at least eight species of the bacterial genus *Megasphaera*, at least nine species of the bacterial genus *Megasphaera*, at least ten or more species of the bacterial genus *Megasphaera*.

The present invention contemplates increasing the feed energy or decreasing methane production of ruminating animals of all ages. According to a particular embodiment, the animals whose feed energy is altered are newborns, typically not more than one day old. According to another embodiment, the animals are not more than two days old. According to another embodiment, the animals are not more than three days old. According to another embodiment, the animals are not more than 1 week old. According to another embodiment, the animals are not more than 2 week old. According to another embodiment, the animals are not more than 1 month old. According to another embodiment, the animals are not more than 3 months old. According to another embodiment, the animals are not more than 6 months old. According to another embodiment, the animals are not more than I, 2, or 3 years old. According to still another embodiment, the animals are adult.

In one embodiment, the agent is a composition comprising bacteria (microbial composition). It may comprises at least one, at least two, at least three, at least four, at least five, at least six, at least seven, at least, eight, at least nine, at least ten, at least 11, at least 12, at least 13, at least 14, at least 15, at least 16, at least 17 or all of the microbial species mentioned in Table 4.

Preferably, the microbial compositions of this aspect of the present invention comprise at least two microbial species. In one embodiment, the microbial compositions of this aspect of the present invention comprise less than 100 microbial species, less than 500 microbial species, less than 400 microbial species, less than 300 microbial species. Exemplary ranges of microbial species include 2-1000, 2-500, 2-250, 2-200, 2-150.2-100, 2-90, 2-80, 2-70, 2-60, 2-50, 2-40, 2-30, 2-25, 2-20, 2-15, 2-10.

Preferably, the composition comprises at last one species of *Megasphaera* (e.g. *M. elsdenii*) and/or the species having a 16S rRNA gene sequence as set forth in SEQ ID NO: 4 or 12.

The relative amounts of each bacterial population in the composition may be determined using appropriate assay systems. In one embodiment, the relative amount of *Megasphaera* bacteria is greater than what exists in a fecal or rumen microbiome of a high energy efficient animal/low methane producer.

The microbial composition may be derived directly from a microbiota sample of the high energy efficient animal. Alternatively, the microbial composition may be artificially created by adding known amounts of different microbes. It will be appreciated that the microbial composition which is derived from the microbiota sample of an animal may be manipulated prior to administrating by increasing the amount of a particular species (e.g. increasing the amount of/or depleting the amount of a particular species such as *Megasphaera*). In another embodiment, the microbial compositions are not treated in any way which serves to alter the relative balance between the microbial species and taxa comprised therein. In some embodiments, the microbial composition is expanded ex vivo using known culturing methods prior to administration. In other embodiments, the microbial composition is not expanded ex vivo prior to administration.

According to one embodiment, the microbial composition is not derived from fecal material.

According to still another embodiment, the microbial composition is devoid (or comprises only trace quantities) of fecal material (e.g, fiber).

The present inventors contemplate agents other than the microbes themselves which increase the ratio of any of the beneficial bacteria set forth in Table 4. Such agents may be metabolites. Metabolites can include lactate or succinate or short-chain fatty acids, which can be a subgroup of fatty acids with 6 or less carbons in their aliphatic tails, for example, acetate, propionate, isobutyrate, isovaleric acid, 3-methylbutanoic acid, valeric acid, pentanoic acid, delphinic acid, isopentanoic acid, and butyrate. Preferably, the short-chain fatty acid is propionate, butyrate, valerate and/or isovalerate. Additional agents that are contemplated include glycans such as starch, cellulose, hemicellulose, pectin, animal-derived cartilage, tissue (glycosaminoglycans and N-linked glycans), and endogenous glycans from host mucus (O-linked glycans).

Following administration of the agents of the present invention, the residual feed intake/methane production can be measured so as to monitor the change. In this way the dose of the agent may be calibrated/regulated according to the needs of the animal. Other parameters that can be rechecked include metabolites, volatile fatty acids.

Prior to administration, the animal may be pretreated with an agent which reduces the number of naturally occurring rumen microbiome (e.g. by antibiotic treatment). According to a particular embodiment, the treatment significantly eliminates the naturally occurring rumen microflora by at least 20%, 30% 40%, 50%, 60%, 70%, 80% or even 90%.

As well as increasing the above mentioned bacterial populations in the rumen microbiome of the animals, the present inventors further contemplate decreasing any one of the bacterial species set forth in Table 5, herein below.

Thus, according to another aspect of the present invention there is provided method of increasing the feed efficiency or decreasing the methane production of a ruminating animal comprising administering to the animal a composition comprising at least one agent which specifically down-regulates an amount of at least one bacteria set forth in Table 5, thereby increasing the feed efficiency or decreasing the methane production of a ruminating animal.

According to a particular embodiment, the agent is not an antibiotic agent.

According to another embodiment, the agent is an antimicrobial peptide.

According to still another embodiment, the agent is a bacteriophage.

According to still another embodiment, the agent is capable of downregulating an essential gene of at least one of the bacterial species described herein below.

Thus, for example, the present inventors contemplate the use of meganucleases, such as Zinc finger nucleases (ZFNs), transcription-activator like effector nucleases (TALENs) and CRISPR/Cas system to downregulate the essential gene.

CRISPR-Cas system—Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of Streptococcus pyogenes have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. Science (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

The microbial composition may be administered per se (e.g. using a catheter or syringe) or may be administered together in the feed (e.g. as a feed additive) of the animal or the drink of the animal.

These ruminants may be fed the feed additive composition of the present invention at any time and in any amount during their life. That is, the ruminant may be fed the feed additive composition of the present invention either by itself or as part of a diet which includes other feedstuffs. Moreover, the ruminant may be fed the feed additive composition of the present invention at any time during their lifetime. The ruminant may be fed the feed additive composition of the present invention continuously, at regular intervals, or intermittently. The ruminant may be fed the feed additive composition of the present invention in an amount such that it accounts for all, a majority, or a minority of the feed in the ruminant's diet for any portion of time in the animal's life. According to one embodiment, the ruminant is fed the feed additive composition of the present invention in an amount such that it accounts for a majority of the feed in the animal's diet for a significant portion of the animal's lifetime.

Examples of additional rumen active feed additives which may be provided together with the feed additive of the present invention include buffers, fermentation solubles, essential oils, surface active agents, monensin sodium, organic acids, and supplementary enzymes.

Also contemplated is encapsulation of the microbes in nanoparticles or microparticles using methods known in the art including those disclosed in EP085805, EP1742728 A1, WO2006100308 A2 and U.S. Pat. No. 8,449,916, the contents of which are incorporated by reference.

The compositions may be administered orally, rectally or any other way which is beneficial to the animal such that the microbes reach the rumen of the animal.

In another embodiment, the present invention provides novel processes for raising a ruminant by feeding the ruminant such a feed additive composition Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Trial design: A total of 146 Holstein Friesian dairy cows were selected for the experiment. Cows with history of diseases, miscarriages and twin pregnancies or that were above first trimester were not included in the experiment. The experimental dairy farm is equipped with a facility that is specially designed to individually monitor all of the animal's functions, feed intake and different physiological parameters. The animals were divided into 7 groups according to lactation period such that each cow was between 50 and 150 d of lactation when monitored. Each group contained between 19 and 21 cows that were monitored for 42 to 49 d. The animals were fed ad libitum a standard lactating cow diet consisting of 30% roughage and 70% concentrate and had free access to water. The cows were habituated with the aforementioned diet for 3 weeks prior to the start of the experiment so that they would become accustomed to their individual feeding station.

The following parameters were automatically monitored three times a day during the experiment: dry matter intake (DMI; kg), weight (kg), milk yield (kg), milk lactose, fat and protein (g) and somatic cell count using the Afimilk program (Afimilk Ltd., Kibbutz Afikim, Israel). Milk samples were sent to an authorized milk quality lab (National Service for Udder Health and Milk Quality, Caesarea, Israel) three times for each group to verify the Afimilk program analysis. Body conditioning score (BCS) was measured once a week by the same person throughout the experiment.

Feed-efficiency parameters, residual feed intake (RFI) and conversion ratio (CR) were calculated according to National Research Council (2001) formulas. In order to increase the statistical power compared to random sampling, extreme phenotypes sampling approach (Li et al., 2011) was applied. Twelve cows with the most extreme and stable RFI values were selected from each group for rumen fluid sampling, six with low and six with high RFI values. Tukey's test was used to verify that the RFI value of each cow was steady throughout the experiment and significantly different from cows in the reciprocal efficiency group. Overall, 78 cows were chosen for sampling and represented the 25% most efficient and 25% most inefficient animals of the whole cohort ($P<0.0001$; FIG. 8).

Sample collection: Rumen samples were collected on 3 consecutive days. The cows were sampled 6 h after feeding in which they were not offered feed; 500 ml of rumen contents were collected using a stainless-steel stomach tube with a rumen vacuum sampler, and pH was immediately determined. Samples for DNA and metabolite extraction were snap-frozen in liquid nitrogen and stored at −80° C. until analysis. Rumen samples for metabolic assays were filtered through six layers of cheese cloth to remove big feed particles, transferred to $CO_2$-containing bottles and flushed with $CO_2$ to maintain anaerobic conditions. Immediately after collection, the rumen samples were maintained at 39° C. up to 1 h until use, and processed in the laboratory, located 100 m away.

Fresh fecal samples were obtained 3 times a day for 4 consecutive days. Samples were immediately frozen at −20° C.

In-vitro digestibility assay: The in-vitro digestibility of plant cell wall fibers, represented by neutral detergent fiber (NDF) or total feed polymers (in dry matter), was determined accordi006Eg to the two-stage technique by Tilley and Terry (Tilley & Terry, 1963). Briefly, cows' feed was dried for 72 h in an aerated 60° C. oven and then ground to pass a 1-mm screen. The feed was incubated with rumen fluid and artificial rumen buffer, in sealed glass tubes.

Artificial rumen buffer was formulated as described previously (McDougall, 1948, Tilley & Terry, 1963). Briefly, 100 ml of buffer A [98 g $NaHCO_3$, 93 g $NaHPO_4.12H_2O$, 5.7 g KCl, 4.7 g NaCl, 1.2 g $MgSO_4.7H_2O$, added to DDW to final volume of 1 liter], was added to 800 ml DDW. The solution was flushed with $CO_2$ to reduce the pH to 6.8-7.0. Then, 1 ml of buffer B [40 g $CaCl_2$ added to DDW to final volume of 1 liter], 50 ml of buffer C [30 g $NH_4HCO_3$ added to DDW to final volume of 1 liter] and 100 μl of buffer D [10 g $MnCl_2.4H_2O$, 1 g $CoCl_2.6H_2O$, 8 g $FeCl_3.6H_2O$ added to DDW to final volume of 1 liter] were added and the buffer was brought to a final volume of 1 liter with DDW.

The tubes were flushed with $CO_2$ and closed with a unidirectional valve cap which only allowed emission of gas from the tube. The tubes were incubated for 24 or 48 h at 39° C. and were shaken five times a day, followed by incubation with acid pepsin. At the end of this procedure, the undigested solids were precipitated by centrifugation at 1,000 g for 10 min and dried in an aerated oven at 60° C. for 72 h. The precipitates were used for residual dry matter (DM) determination by weighing or for residual NDF determination by following the procedure of Van Soest et al. (Van Soest et al., 1991). The results are expressed as mean feed digestibility in the rumen from two consecutive sampling days.

In-vivo digestibility: Fecal grab samples were pooled for each cow, dried at 60° C. for 72 h in a forced-air oven and ground to pass a 1-mm screen. The indigestible NDF content was determined in the ration and in the fecal samples according to a previously reported method (Lippke et al., 1986) after incubation with rumen fluid for 72 h and was used as an internal marker for the apparent total-tract DM digestibility analysis. Each cow's in-vivo DM and NDF digestibility of the ration was calculated using its average DM intake and fecal output.

In-Vitro Methane Emission Assay

Samples were diluted 1:2 (v/v) with artificial rumen buffer. Duplicates of 5 ml aliquots from each diluted sample were transferred to screw-cap glass tubes (ISI, Israel Scientific Instruments Ltd., Petah-Tikva, Israel) suitable for methane measurement using a GC system (HP-5890 series II, FID detector). The samples were incubated at 39° C. for 24 h with 0.5 g DM feed, and then analyzed by GC for methane emission. Samples of 0.5 ml gas from the tube headspace were injected into a 182.88 cm×0.3175 cm×2.1 mm packed Supelco analytical-45/60 Molecular sieve 5A column (Sigma-Aldrich) with helium carrier gas set to a flow rate of 10 ml/min and an oven temperature of 200° C. The oven temperature remained steady for a total run time of 5 min. A standard curve was generated using pure methane gas.

Methane production was quantified for 36 rumen microbiome samples of the most extreme animals of the feed-efficiency groups (18 efficient and 18 inefficient), with two biological repeats of each animal.

Identification and quantification of rumen fluid metabolites: Frozen rumen fluid samples were thawed at 25° C. and centrifuged at 10,000 g for 15 min. The supernatant was filtered through a sterile 0.45 μm filter (EMD Millipore). Rumen fluid samples were kept on ice during metabolite extraction in the GC-MS and GC metabolite identification and quantification pipelines to minimize metabolite degradation.

The rumen samples were analyzed by GC-MS for polar metabolites and by GC with a FID detector for SCFAs. The extraction and derivatization protocol for the GC-MS analysis was adapted from a previously described method (Saleem et al., 2013). Derivatized extracts were analyzed using an Agilent 5975C GC and an Agilent 7890A MS operating in electron impact (EI) ionization mode. Aliquots (1 μl) were injected (splitless) into a 30 m×0.25 mm×0.25 μm HP-5MS Ultra Inert column (Agilent Technologies) with helium carrier gas set to a flow rate of 1 ml/min and initial oven temperature of 70° C. The oven temperature was held constant at the initial temperature for 2 min, and thereafter increased at 10° C./min to a final temperature of 310° C., and a final run time of 45 min. Samples were run using full scan in a mass range of 50-500 m/z (1.7 scan/s) with a detection delay of 4 min. Retention indices were calculated using a C8-C20 alkane standard mixture solution (Sigma-Aldrich) as the external standard. Quantification and identification of trimethylsilylated metabolites were performed using the NIST database and HPLC-grade standards.

For SCFA identification and quantification, 400 μl of filtered rumen fluid was mixed with 100 μl of 25% metaphosphoric acid solution (w/v in double-distilled water) and vortexed for 1 min. The samples were incubated at 4° C. for 30 min and subsequently centrifuged for 15 min at 10,600 g. The supernatant was decanted into new tubes, then 250 μl methyl tert-butyl ether (MTBE) (Sigma-Aldrich) was added and the tubes were vortexed for 30 s. Another cycle of centrifugation was performed for 1 min at 10,600 g. The upper phase, which contained MTBE+SCFAs, was analyzed using an Agilent 7890B GC system with a FID detector. The temperatures at the inlet and detector were 250° C. and 300° C., respectively. Aliquots (1 μl) were injected with a split ratio of 1:25 into a 30 m×0.32 mm×0.25 μm ZB-FFAP column (ZEBRON) with helium carrier gas set to a flow rate of 2.4 ml/min and initial oven temperature of 100° C. The oven temperature was held constant at the initial temperature for 5 min, and thereafter increased at 10° C./min to a final temperature 125° C., and a final run time of 12.5 min.

Quantification and identification of metabolites were performed using HPLC-grade standards. All metabolites were normalized to the organic matter content of the rumen fluid they were extracted from. Rumen samples were filtered through a sterile 0.45 μm Supor Membrane filter (PALL Life Sciences). The organic C in the rumen samples was analyzed with a Formacs, combustion total organic carbon (TOC) analyzer (Skalar, De Breda, Netherlands).

Microbial DNA extraction: The rumen microbial fraction was separated according to Stevenson and Weimer (Stevenson & Weimer, 2007), with minor modifications to suit the needs of these experiments as described in Jami et al. (Jami et al., 2013). The DNA extraction was performed as described by Stevenson and Weimer (Stevenson & Weimer, 2007).

Shotgun DNA sequencing and analysis: Metagenomic DNA libraries were constructed with the TruSeq DNA Sample Prep kit (Illumina). Libraries were pooled and sequenced on two lanes for 151 cycles from each end on a HiSeq2500 (Illumina) and processed with Casava 1.8.2 (Illumina). On average, 35,581,041±6,899,269 paired end reads were obtained from each sample and 2,775,321,186 paired end reads were obtained overall. 18.6% of the reads did not pass artifact filtering and trimming using MOCAT pipeline (Kultima et al., 2012).

To obtain a more comprehensive metagenome, a joint assembly of all data from the 78 cows was created. This compensated for the lower sequencing depth of each individual sample and any bias caused by assembly of individual samples. Reads from all samples were pooled and assembled into one metagenome using CLC Bio, package CLC Assembly Cell version 3.2.2 with K-mer=21 and default parameters; 16,784,830 contigs were obtained. A QC pipeline of dereplication and screening for Bos taurus reads was performed using the MG-RAST pipline. No redundancies were found and 0.43% of the contigs were discarded after removing Bos taurus contaminants. The phylogenetic origin of each contig was annotated with RefSeq database (Pruitt et al., 2007) ($E \leq 10^{-5}$) using the MG-RAST pipeline (Meyer et al., 2008).

Gene calling was performed on the contigs using FragGeneScan (Rho et al., 2010); 21,531,511 genes were identified over all. Each sample's reads were recruited against the overall genes using BWA (Li & Durbin, 2009) with 98% identity and default parameters; a threshold of one read for gene identification was chosen to include rare genes in the analysis. On average, 52.4% of the reads from each sample were mapped to the obtained genes, without differences between the efficiency groups (FIG. 9). An average of 4,079,212 genes were identified in each sample, the abundance of a specific gene was calculated by the number of reads uniquely recruited, normalized to the length of the gene and total reads obtained from the sample. The number of genes detected had no dependence on the number of mapped reads (FIG. 10).

16S rDNA Sequencing and Analysis

The 16S V3 region was amplified using the primers 357F CCTACGGGAGGCAGCAG (SEQ ID NO: 20) and 926R CCGTCAATTCMTTTRAGT (SEQ ID NO: 21) (Peterson et al., 2009). The libraries were pooled and sequenced on one MiSeq flowcell (Illumina) for 251 cycles from each end of the fragments and analyzed with Casava 1.8. Overall, 49,760,478 paired end reads were obtained for all 3 sampling days, with an average of 212,652 reads per sample per day.

Data quality control and analyses were performed using the QIIME pipeline version 1.7.0 (Caporaso et al., 2010). Species were defined at 97% identity using UCLUST (Edgar, 2010). Taxonomy assignment of species was performed using BLAST against the 16S rRNA reference database RDP (version 10) (Cole et al., 2003). All singletons and doubletons were removed from the dataset, resulting in 81,000 species with an average of 5,039 per sample. Species were binned at different taxonomic levels to receive taxon abundances for each phylogenetic level (FIG. 11).

Biodiversity analysis: Within-sample (alpha) diversity was calculated using Shannon index and dominance was determined according to 1—Simpson index (Harper, 1999). The indices of 16S rRNA gene profiles were calculated using bootstrapping with 9,999 replicates. Richness of genes and taxa are presented as simple counts of genes and taxa.

Identifying differential species and genes: The statistical significance of differences in species and gene abundance between the efficiency groups was tested by Wilcoxon rank-sum test coupled with a bootstrapping approach adopted from Le Chatelier et al. (Le Chatelier et al., 2013): 70% of the whole sampled cohort was randomly chosen 30 times and significance was determined at P<0.05 with bootstrap=0.8 as a threshold. This process was repeated with another 30 iterations on the 48 most extreme cows (24 efficient and 24 inefficient). Overall, 18 significantly different species and 34,166 significantly different genes common to all 60 tests were further analyzed (P<0.05). Species and genes that were significantly different were correlated to the RFI parameter using Spearman correlation. Functional annotation of significant genes was achieved using BLASTP with $E \leq 10^{-6}$ against KEGG PATHWAY, MODULE, BRITE, GENES and ORTHOLOGY databases (2014; 46% annotation) (Kanehisa et al., 2011). These genes were also blasted against the NR database (Pruitt et al., 2007), and their phylogenetic annotation was determined according to the best hit (BLASTP with $E \leq 10^{-6}$; 89% annotation).

Statistical tests and estimation of false discovery rate: Tukey's, Student t and Wilcoxon rank-sum tests were conducted depending on the normality of distribution of the input data. All tests were corrected for false discovery rate using the method described by Benjamini et al. (Benjamini & Hochberg, 1995) unless otherwise noted. In permutation t-test, significance of the difference between means was inferred by performing t-test between the two groups and comparing the resulting t-statistic to the t-statistics resulting from 9,999 permutations of random group assignments (two-tailed, P<0.05) (Davis, 1986). For multiple hypothesis correction, the distribution of t-test P-values was compared to the lowest P-values distribution resulting from 9,999 permutations of random group assignments according to Westfall & Young (Westfall & Young, 1993). This procedure was performed using the R bioconductor package multtest (K. S. Pollard et al., 2005), function mt.maxT, individually for each metabolic or activity test, namely polymers, SCFAs, methane and all other measured metabolites. Variance similarity was tested where required by the statistical test.

Predictions of different physiological parameters: Feature selection of microbial species and genes was conducted by choosing species or genes that were significantly different in their presence/absence using the Fisher's exact test. Species and genes were sorted separately according to their P-value in ascending order and grouped into bins of 100 features. Each bin was used as predictive features for the feed-efficiency phenotype using the KNN algorithm (Aha, 1997) with k=3. The mean accuracy of the prediction was calculated using cross-validation of 1,000 iterations for each bin, in which 70% of the samples were used as a training set and the remaining 30% were used as a test set to measure the accuracy of the prediction. Changing the bin size (bins ranging in size from 50 to 1,000 features per bin) did not affect the accuracy of the prediction. To check the significance of the classifications accuracy a permutations technique was employed. The classification procedure was repeated 100 times, each time after randomly shuffling (permutating) the sample labels. The P-value for each classification accuracy was then obtained by the percentage of permutation runs in which the accuracy achieved was greater than the classification accuracy achieved with the original non-permutated data. The same prediction methodology, accuracy and P-value determination were applied to several other metabolic parameters—CR, milk yield, milk energy, milk lactose, milk fat, milk protein, BCS, pH and DMI. For each metabolic parameter prediction test, the cows were separated into two groups, by the physiological parameter's mean value.

For each physiological index, Receiver Operation Characteristics (ROC) curves and Area Under Curve (AUC) measures were obtained based on the average of 1,000 KNN cross-validation iterations. The analysis was performed with the Metrics class that is part of the SKLEARN python machine-learning framework.

Recruitment to microbial genomes and metabolic pathways: Reads from each sample were sub-sampled according to the sample with lowest number of reads (21,000,000). The reads from each sample were aligned using BWA program to a dataset of 59 microbial genomes downloaded from NCBI using BWA with 98% identity and default parameters. Reads were also recruited to metabolic pathways of the significantly different metabolites (P<0.05) using the same method. Our database consisted of all possible KEGG enzymes for each metabolic pathway. The EC numbers used for each metabolic pathway are described in Table 1, herein below.

TABLE 1

| Acetate | Butyrate | Propionate | Valerate | Isovalerate | Lactate | Methane |
|---|---|---|---|---|---|---|
| 2.8.3.8 | 2.7.2.7 | 1.3.8.7 | 1.2.1.19 | 1.1.1.26 | 1.1.1.27 | 1.12.98.1 |
|  | 2.8.3.8 | 2.8.3.1 | 1.2.1.3 | 1.2.1.24 | 1.1.1.28 | 1.12.982 |
|  |  | 4.1.1.41 | 1.2.1.5 | 1.2.1.3 | 1.13.12.4 | 1.2.99.5 |
|  |  | 4.2.1.54 | 1.2.1.47 | 1.2.1.4 | 1.2.1.2 | 1.5.1 |
|  |  | 5.4.99.2 | 1.2.3.1 | 1.2.1.5 | 3.1.2.6 | 1.5.98.1 |
|  |  | 51.99.1 | 1.2.1.8 | 1.2.1.77 | 4.2.1.130 | 1.5.98.2 |
|  |  |  | 2.8.3.8 | 1.2.1.8 |  | 1.8.98.1 |
|  |  |  | 3.1.1.1 | 1.2.7.5 |  | 2.1.1.86 |
|  |  |  | 3.1.1.22 | 3.1.1.8 |  | 2.8.4.1 |
|  |  |  | 3.1.1.8 | 3.1.2.20 |  | 23.1.101 |
|  |  |  |  | 3.5.5.5 |  | 3.5.4.27 |
|  |  |  |  | 3.5.5.7 |  |  |

The existence of the propionate production acrylate pathway in the genomes of the examined lactate utilizers *Selenomonas ruminantium* and *Anaerovibrio lipolyticus* was additionally tested by blasting them against all possible KEGG enzymes belonging to the acrylate pathway (EC 1.3.8.7, 2.8.3.1 and 4.2.1.54) using a threshold of above 70% identity, 70% alignment length of the subject gene and $E \leq 10^{-5}$.

Results

Construction of a Rumen Metagenome Reference Dataset

To determine whether there are microbiome features that are associated with the cow's energetic efficiency, the individual feed-efficiency of 146 Holstein Friesian cows was first determined. Each animal was automatically monitored for multiple parameters used to calculate feed-efficiency (using the RFI approach). For further analyses, the upper and lower 25% of the animals that exhibited extreme feed-efficiency values were chosen, for a total of 78 animals—40 efficient and 38 inefficient (FIG. 8). Metagenomic DNA samples of these animals' rumen microbiomes were subjected to 16S rRNA gene sequencing and whole-genome shotgun sequencing. The metagenomics reads of all samples were pooled and assembled, and the predicted genes served as a reference dataset (Materials and Methods). The metagenome contained 96.72% bacterial sequences, 1.73% archaeal sequences and 1.34% eukaryotic sequences, similar to what was previously described for rumen microbiome metagenomes (Brulc et al., 2009). None of the eukaryotic sequences showed significance in the analyses.

Microbiome Features Differ and can Predict Feed-Efficiency Phenotype

Figure 1B:
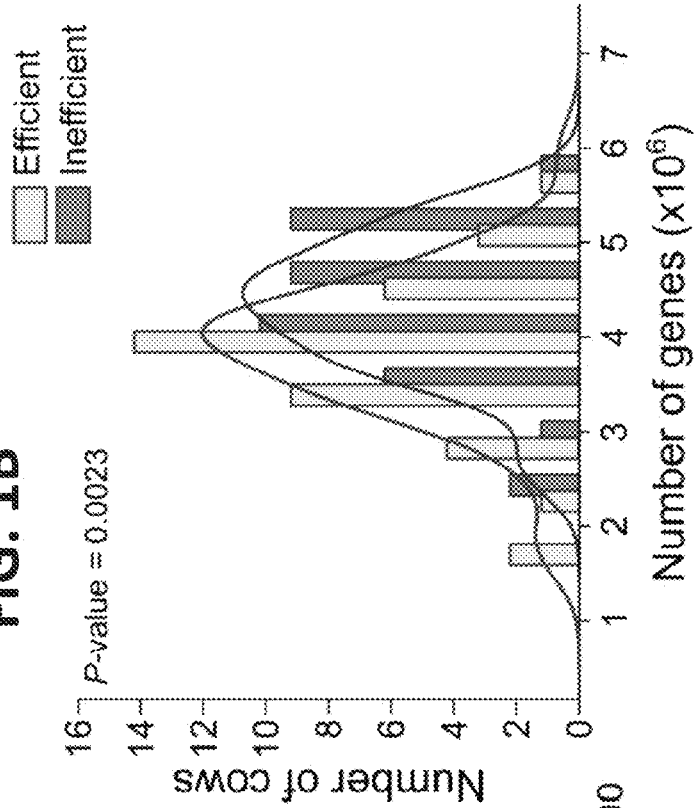
Figure 1A:
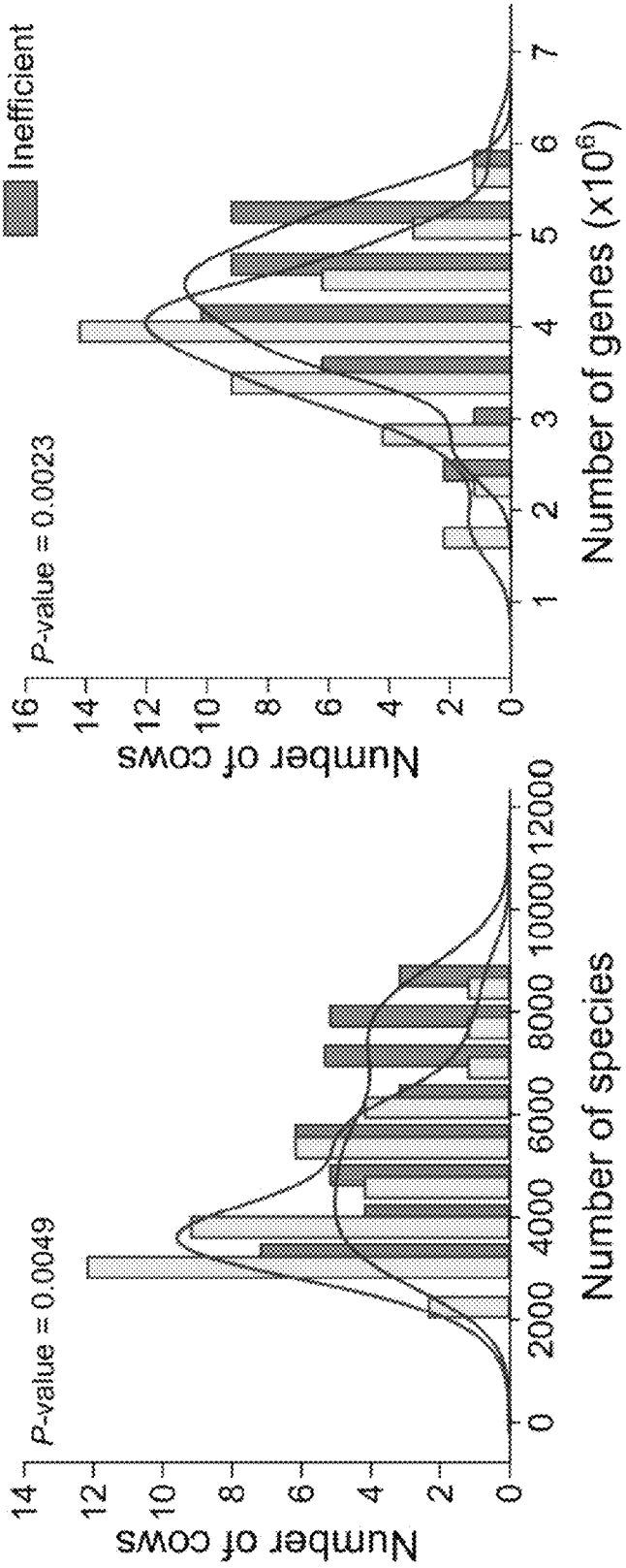
Figure 1C:
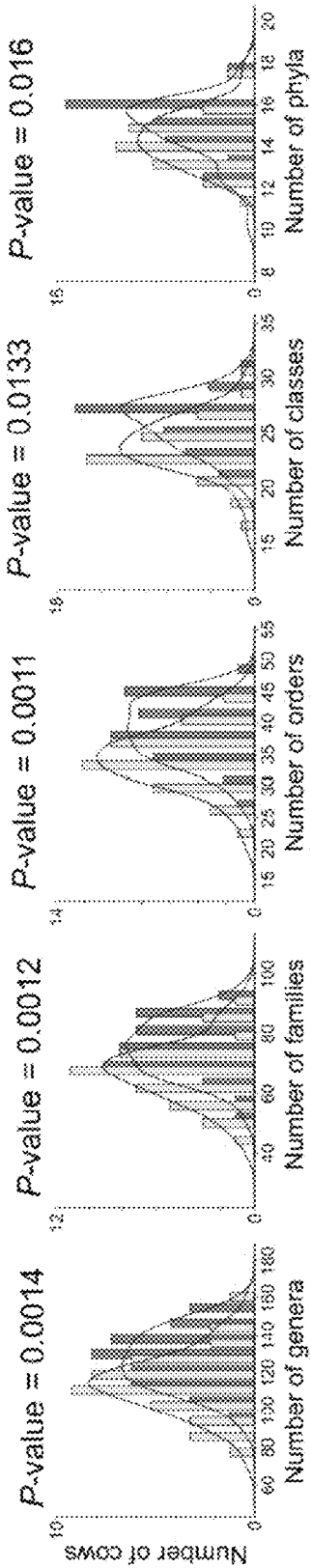
Figure 1E:
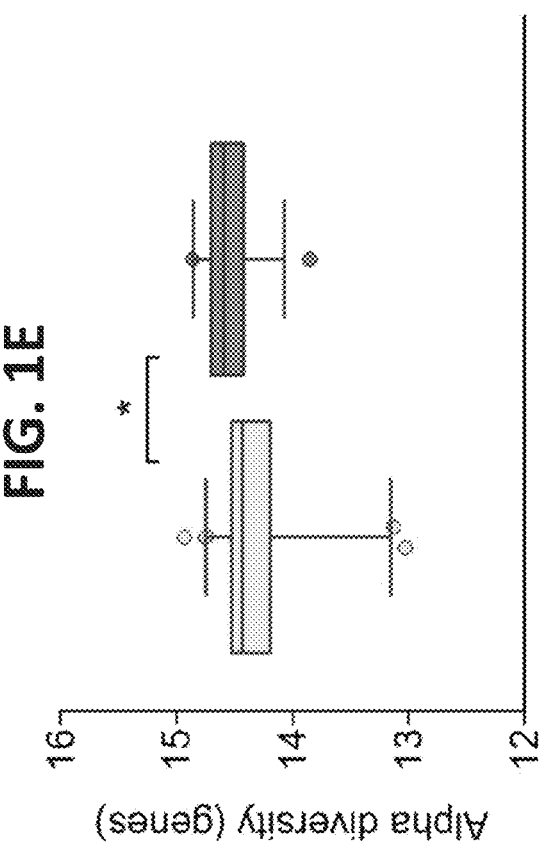
Figure 1G:
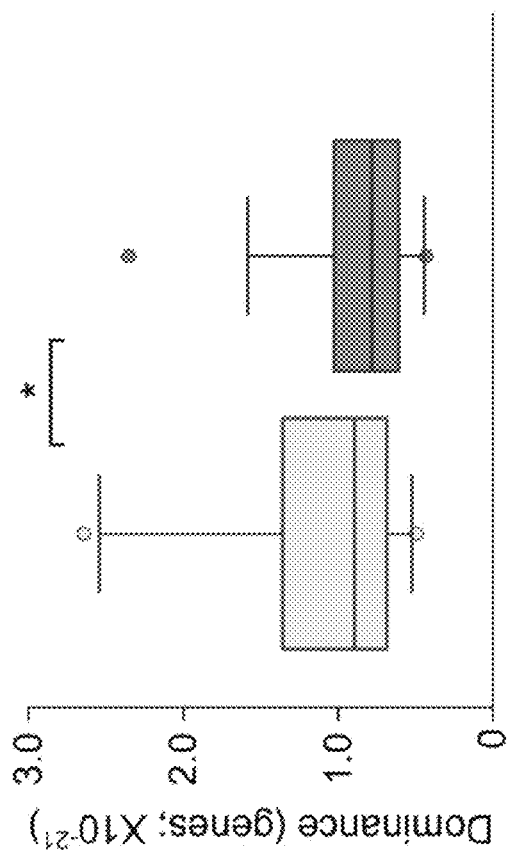
Figure 1D:
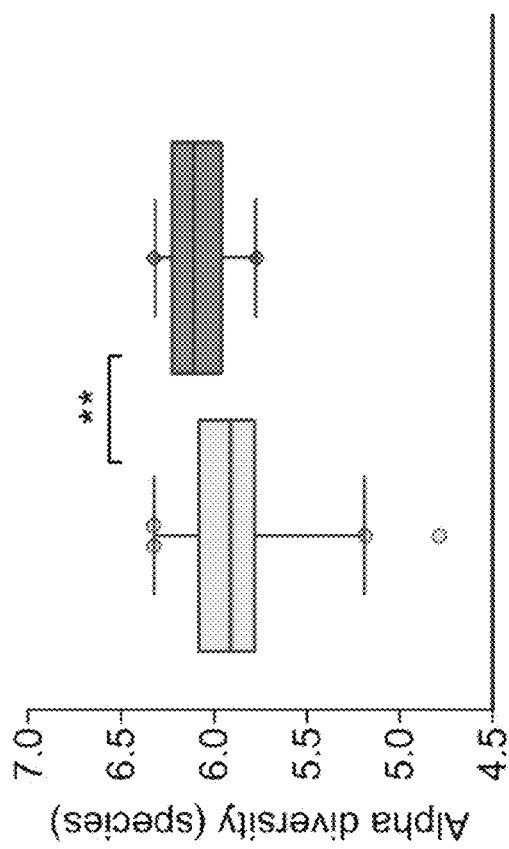
Figure 1F:
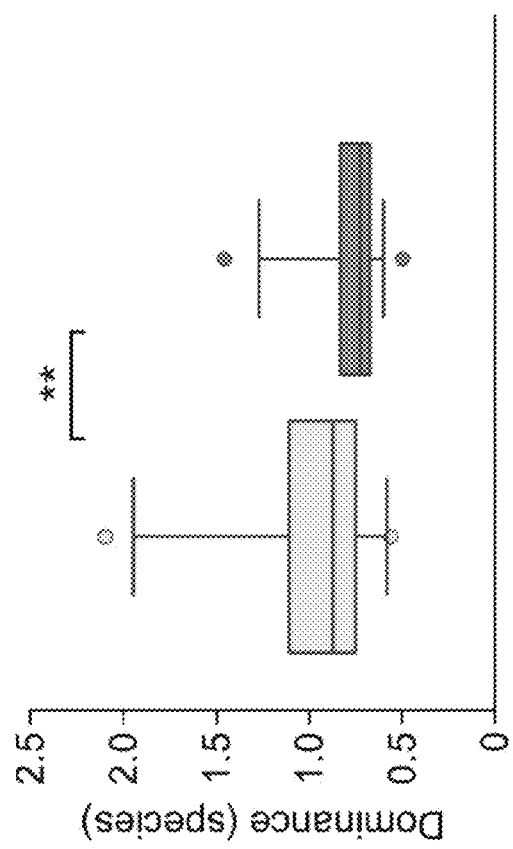

A comparison of microbiome richness across the animals revealed significantly lower richness in the efficient cows' microbiomes in both species (P=0.0049) and gene content (P=0.0023; FIGS. 1A-B). The differences in taxon richness were apparent up to the phylum level (FIG. 1C), further stressing the intensity of this phenomenon. Taxon composition and gene content were derived from two different procedures of sequencing and analysis, and therefore the agreement between these findings highlights the robustness of the observation. The differences in richness were also accompanied by significantly lower diversity and higher dominance in the efficient animals' microbiomes at the species and gene levels (P<0.01 and P<0.05 respectively, for both diversity and dominance; FIGS. 1D and 1G and Table 2).

TABLE 2

| Inefficient | Efficient | Diversity index |
|---|---|---|
| 6.092 ± 0.03 | 5.87 ± 0.05 | Alpha diversity species** |
| 14.53 ± 0.028 | 14.32 ± 0.06 | Alpha diversity genes** |
| 0.0079 ± 0.0003 | 0.01 ± 0.001 | Dominance species* |
| $0.86 \times 10^{-21} \pm 6.15 \times 10^{-23}$ | $1.14 \times 10^{-21} \pm 9.72 \times 10^{-23}$ | Dominance genes* |

These differences were apparent up to the family level (FIGS. 12A-B). These differences in microbiomes of efficient and inefficient cows begged the question of whether microbiome features could be used as markers for the feed-efficiency trait.

Thereupon, the species and gene composition of the rumen microbiomes were used to successfully predict the animals' feed-efficiency phenotypes with up to 91% accuracy using the k-Nearest Neighbors (KNN) algorithm (Aha, 1997). For the feature-selection process, a Fisher's Exact test was used to measure differences in presence/absence between microbiomes of efficient and inefficient animals. The species and genes were ranked separately according to their P-values in ascending order and divided into bins of 100 features to be used for prediction. Each bin was tested for its ability to predict high or low feed-efficiency. The mean prediction accuracy was calculated using cross-validation for each bin (1,000 iterations). The first species bin's prediction accuracy was 80%, while the first gene bin reached an accuracy of 91% (FIGS. 2A-B). The species prediction accuracy declined to 50% (accuracy of a random guess) after the fifth bin, while the decline in prediction accuracy for the genes followed a much more moderate slope, with the first four predictive bins at above 90% accuracy with highly significant P-values. These differences in the slope of prediction accuracy could stem from the fact that each species represents a single genome containing thousands of genes therefore declining more rapidly compared bins composed of hundreds of single genes.

The microbiome features were also highly predictive of other physiological parameters, such as milk lactose content and milk yield (FIGS. 13A-I and 14A-I). The sensitivity and specificity of the predictive bins was further assessed by performing Receiver Operating Characteristic (ROC) analysis for the first five bins, for both the species and genes data of each physiological parameter (FIGS. 15A-J and 16A-J). This analysis showed high sensitivity and specificity of the predictions of the host physiological traits based on these microbiome features, as the area under curve (AUC) index had high values that are considered to be good for the species data, and excellent for the genes data (AUC>0.8, AUC>0.9 respectively). This high prediction accuracy indicated that the differences in microbiome gene content and taxonomic composition could be used to classify and predict the cow's energetic efficiency.

Microbiome Metabolic Activity Varies in Cows with Different Feed-Efficiencies

Diversity, richness and dominance are key ecological determinants that, when altered in a given ecosystem, are expected to have a marked effect on its functionality (Hooper et al., 2005). Hence, following the findings of evident differences in these parameters (FIGS. 1A-G, FIGS. 12A-B and Table 2), the functionality of the rumen ecosystem was further investigated. Several microbial activity assays as well as a series of 41 metabolites were targeted and measured, representing the processes and products of different trophic levels of the rumen microbiome from efficient and inefficient cows, starting from degradation of the ingested plant fiber to the end products (FIG. 3).

Significant differences were discovered in most SCFAs. Out of the six SCFAs measured, four—propionate, butyrate, valerate and isovalerate—were at higher concentrations in the rumen of efficient cows (FIG. 3, metabolic end products and Table 3).

that propionate and butyrate production competes with methanogenesis for hydrogen and presents an alternative mechanism that serves as an electron sink (Ungerfeld, 2015). The production of more SCFAs and less methane by the efficient cows' microbiomes is in agreement with the higher energetic efficiency.

The analysis did not reveal any significant differences in the microbiomes' ability to degrade the plant cell wall in the diet, in vitro or in vivo (FIG. 3, polymers and FIGS. 17A-D).

Differential Abundance of Rumen Microbes and Metabolic Pathways

The lower diversity and higher dominance in gene content and taxonomic composition apparent in the microbiome of efficient cows, together with changes in metabolite assortments, suggested that the flux through collective metabolic pathways is different in this microbiome group. This raised the hypothesis that this might be due to changes in the occupancy of specific rumen microbial niches, defined by metabolic and physical characteristics, by functional groups that differ in their resource demands or output products.

To explore this hypothesis, a permutative Wilcoxon rank-sum test was conducted in which gene and taxonomic profiles were compared between the microbiomes of efficient and inefficient animals (Materials and Methods). Overall, 18 species and 34,166 genes differentiated the microbiomes of efficient and inefficient cows (FIGS. 18 and 19); of these, 2 species and 227 genes were more abundant in efficient cows. These species and genes were not only differentially abundant in cows with different RFI values, but were also significantly correlated to the intensity of the phenotype (FIG. 5A). The lower numbers of species and genes that were more abundant in the efficient cows' microbiomes are compatible with the higher dominance and lower

TABLE 3

| Metabolite | Efficient (mM) | Inefficient (mM) | Efficient (mM per g/L OM) | Inefficient (mM per g/L OM) |
| --- | --- | --- | --- | --- |
| Acetate | 35.61 ± 1.24 | 33.26 ± 1.55 | 11.84 ± 0.26 | 11.1 ± 0.42 |
| Propionate | 22.32 ± 0.82 | 19.45 ± 0.84 | 7.45 ± 0.23$^a$ | 6.49 ± 0.22$^b$ |
| Isobutyrate | 1.5 ± 0.05 | 1.35 ± 0.06 | 0.5 ± 0.01 | 0.45 ± 0.02 |
| Butyrate | 22.03 ± 1.16 | 19.6 ± 0.9 | 7.25 ± 0.27$^a$ | 6.52 ± 0.22$^b$ |
| Isovalerate | 2.94 ± 0.15 | 2.5 ± 0.13 | 0.97 ± 0.03$^a$ | 0.84 ± 0.04$^b$ |
| Valerate | 3.75 ± 0.14 | 3.15 ± 0.14 | 1.25 ± 0.04$^a$ | 1.05 ± 0.04$^b$ |
| Total VFAs | 88.14 ± 3.13 | 79.3 ± 3.28 | 29.26 ± 0.62$^a$ | 26.46 ± 0.82$^b$ |
| Lactate | 0.028 ± 0.007 | 0.073 ± 0.02 | 0.009 ± 0.002 | 0.03 ± 0.009 |
| Succinate | 0.29 ± 0.03 | 0.33 ± 0.03 | 0.1 ± 0.01 | 0.11 ± 0.01 |

In addition, the total concentration of SCFAs was higher in the efficient animals showing an increase of 10% between the two efficiency groups (P<0.01; FIG. 4A). These differences are considered to have a marked effect on animal productivity, given that approximately 70% of the net energy requirements of the animal are supplied by SCFAs (Seymour et al., 2005).

Interestingly, the propionate-to-acetate ratio in the efficient animals was also significantly higher than in the inefficient ones (P<0.05; FIG. 4B); an increase in this ratio is associated with a decline in methane production and increased energy retention by cattle (Russell, 1998). This finding was congruent with the measurements of the microbiomes' methanogenesis potential, where it was evident that the efficient cows' microbiomes produce significantly less methane than their inefficient counterparts (P<0.01; FIG. 3, metabolic end products). The finding of higher concentrations of SCFAs and lower methane emission from the efficient rumen microbiomes is consistent with the notion richness in species and gene composition of these microbiomes. The annotation and analysis of the differentiating genes against the KEGG database (Kanehisa et al., 2011) were also in agreement with these findings, as well as with the metabolomic analysis. Among the KEGG pathways and resultant metabolites that were enriched in the inefficient cows' microbiomes were enzymes from the protein digestion and absorption category, amino acid biosynthesis and the Methane metabolism category.

Furthermore, a significantly lower number of KEGG pathways were enriched in the efficient cows' microbiomes, resulting in a significantly lower number of potential products.

These findings suggest that there is more diverse use of resource compounds, such as dietary proteins, pyruvate, acetyl-CoA and hydrogen, in the inefficient cows' microbiomes, resulting in a more diverse array of produced metabolites, some of which affect the animal's energy harvest in a negative manner or cannot be utilized by the animal for its energy requirements. In the efficient cows' microbiomes, the use of these compounds is dominated by a limited number of metabolic pathways that are more relevant and valuable for the energy needs of the animal.

The phylogenetic annotations of genes that were enriched in the efficient cows' microbiomes were dominated by the rumen bacterial species *Megasphaera elsdenii*, a highly potent utilizer of lactate for the production of butyrate and propionate (FIG. 5B). This annotation, or any other closely related annotation, did not appear in the inefficient cow microbiomes' enriched genes. Overall, the inefficient cows' microbiomes were less dominated by a specific taxon unique to that microbiome group (FIG. 5B), further supporting the hypothesis of higher dominance of specific functional groups in the microbiomes of efficient cows. This was also reinforced by the annotation of the two species that were significantly more abundant in the efficient cows' microbiomes in the 16S rRNA gene analysis. One annotation that appeared exclusively in this group was of the genus *Megasphaera*. The other abundant species belonged to the family Lachnospiraceae, which also had a representative in the species that were more abundant in the inefficient cows' microbiomes (FIG. 5A).

*M. elsdenii* was also highly enriched in the efficient cows' microbiomes using a different genomic analysis, in which reads from all samples were aligned to a database of 59 sequenced rumen and gut microbial genomes that are known to be involved in various metabolic processes and were also identified in the previous analysis. Here again, inefficient microbiomes were significantly enriched in several microbial genomes, among them *Methanobrevibacter ruminantium* (P<0.01), a methanogenic archaeon of the most abundant genus in the rumen (FIG. 6A and FIG. 20). This exploration was further expanded by asking whether these observations are true not only for genomes of specific microbes but for all possible KEGG enzymes belonging to rumen end product metabolic pathways by using the same read-alignment approach (Materials and Methods). In agreement with the previous results, the methanogenesis pathway was significantly enriched in the inefficient cows' microbiomes (P<0.01). Out of all examined pathways for propionate production only the acrylate pathway that utilizes lactate to propionate was enriched in the efficient cows' microbiomes (P<0.01; FIG. 6B). It should be noted that this pathway is encoded in the genome of *M. elsdenii* (Prabhu et al., 2012) and *Coprococcus catus* (Reichardt et al., 2014) which were both found by the analyses to be significantly enriched in efficient animals' microbiomes (FIGS. 5A-B, 6A, FIG. 20), and not in the other examined lactate utilizing microbial genomes (*S. ruminantium* and *A. lipolyticus*). Furthermore, reads aligned to this pathway are predominantly annotated as *M. elsdenii* and *C. catus*, however annotations of *Clostridium propionicum* and *Clostridium botulinum* were also detected (FIG. 21). This highlights the acrylate pathway as the main contributor to the increase in propionate and decrease in lactate observed in the metabolomic analysis of the efficient cows' microbiome group (FIG. 3).

Table 4 provides a list of bacteria that positively correlate with high energy efficiency, low methane production, as gleaned from the experiments described herein above.

TABLE 4

| | Sequence_id | SEQ ID NO: |
|---|---|---|
| (Clostridiales)genus *Megasphaera* | denovo133121 | 4 |
| family Lachnospiraceae | denovo613908 | 12 |
| *Prevotella bryantii* B14 | | |
| *Prevotella albensis* DSM 11370 JCM 12258 | | |
| *Ruminococcus flavefaciens* ND2009 | | |
| *Megasphaera elsdenii* DSM 20460 | | |
| *Megasphaera elsdenii* | | |
| *Megasphaera elsdenii* T81 | | |
| *Streptococcus bovis* ATCC 700338 | | |
| *Coprococcous catus* GD/7 | | |
| *Methanobrevibacter smithii* ATCC 35061 | | |
| *Bacteroides* sp. AR29 | | |
| *Prevotella* sp. AGR2160 | | |
| *Allisonella histaminiformans* DSM 15230 | | |
| *Olsenella* sp. KH2P3 | | |
| *Bacteroides* sp. AR20 | | |
| *Prevotella* sp. HUN102 | | |
| *Olsenella umbonata* DSM 22619 | | |

Table 5 provides a list of bacteria that positively correlate with low energy efficiency, high methane production, as gleaned from the experiments described herein above.

TABLE 5

| | Sequence_id | SEQ ID NO: |
|---|---|---|
| family Lachnospiraceae | denovo167490 | 5 |
| order Clostridiales | denovo108376 | 2 |
| (Bacteroidales)genus *Prevotella* | denovo255270 | 6 |
| (Clostridiales) family Mogibacteriaceae | denovo540895 | 9 |
| order Bacteroidales | denovo1028257 | 1 |
| (Bacteroidales) genus *Prevotella* | denovo428724 | 8 |
| order Clostridiales | denovo110296 | 3 |
| order Bacteroidales | denovo582030 | 11 |
| order Bacteroidales | denovo747362 | 14 |
| (Bacteroidales)genus *Prevotella* | denovo976950 | 18 |
| order Clostridiales | denovo963919 | 17 |
| (Bacteroidales) family S24-7 | denovo565357 | 10 |
| (Bacteroidales) genus CF231 | denovo358968 | 7 |
| order Clostridiales | denovo640035 | 13 |
| order Clostridiales | denovo865633 | 16 |
| (Clostridiales) family Ruminococcaceae | denovo855267 | 15 |
| order Clostridiales | denovo980934 | 19 |
| *Prevotella ruminocola* Ga6b6 | | |
| *Prevotella ruminocola* 23 | | |
| *Prevotella brevis* P6B11 | | |
| *Prevotella brevis* ATCC 19188 | | |
| *Fibrobacter succinogenes* S85 | | |
| *Succinimonas amylolytica* DSM 2873 | | |
| *Ruminobacter* sp. RM87 | | |
| *Succinivibrio dextrinoslvens* H5 | | |
| *Ruminococcus flavefaciens* FD-1 | | |
| *Ruminococcus flavefaciens* 17 | | |
| *Ruminococcus albus* 8 | | |
| *Ruminococcu albus* AD2013 | | |
| *Ruminococcu albus* 7 | | |
| *Butryvibrio fibrisolvens* YRB2005 | | |
| *Butryvibrio fibrisolvens* WTE3004 | | |
| *Butryvibrio fibrisolvens* MD2001 | | |
| *Butryvibrio fibrisolvens* FE2007 | | |
| *Butryvibrio fibrisolvens* 164 | | |
| *Bifidobacterium pseudolongum* DSM 20092 | | |
| *Bifidobacterium pseudolongum* AGR2145 | | |
| *Bifidobacterium pseudolongum* PV8 2 | | |
| *Bifidobacterium adolescentis* 22L | | |
| *Bifidobacterium adolescentis* L2 32 | | |
| *Bifidobacterium thermophilum* RBL67 | | |
| *Bifidobacterium thermophilum* DSM 20212 | | |
| *Bifidobacterium thermophilum* DSM 20210 | | |
| *Anaerovibrio lipolyticus* | | |
| *Anaerovibrio lipolyticus* LB2005 | | |
| *Selenomonas ruminantium* ATCC 12561 | | |
| *Selenomonas ruminantium* AC2024 | | |

TABLE 5-continued

| Sequence_id | SEQ ID NO: |
|---|---|
| Selenomonas ruminantium AB3002 | |
| Streptococcus bovis B315 | |
| Lachnospira multipara MC2003 | |
| Lachnospira multipara LB2003 | |
| Lachnospira multipara ATCC 19207 | |
| Lactobacillus reuten strain TMW1.112 | |
| Lactobacillus reuten LTH5448 | |
| Lactobacillus reuten LTH2584 | |
| Pseudobutyrivibrio ruminis HUN009 | |
| Pseudobutyrivibrio ruminis CF1b | |
| Pseudobutyrivibrio ruminis AD2017 | |
| Lactobacillus plantarum strain AG30 | |
| Peptostreptococcus anaerobius 653 L | |
| Peptostreptococcus anaerobius VPI 4330 DSM 2949 | |
| Clostridium aminophilum DSM 10710 | |
| Clostridium sticklandii | |
| Methanobrevibacter ruminantium M1 | |
| Methanomicrobium mobile BP T502 | |
| Methanobacterium formicicicum | |
| Methanosphaera stadtmanae DSM 3091 | |
| Anaerovibrio sp. RM50 | |
| Bacteroides sp. Ga6A1 | |
| Bacteroides sp. Ga6A2 | |
| Blautia schinkii DSM 10518 | |
| Blautia sp. SF-50 | |
| Blautia wexlerae AGR2146 | |
| Butyrivibrio fibrisolvens AB2020 | |
| Butyrivibrio fibrisolvens ND3005_2 | |
| Butyrivibrio proteoclasticus FD2007 | |
| Butyrivibrio proteoclasticus P6B7 | |
| Butyrivibrio sp. AC2005 | |
| Butyrivibrio sp. AD3002 | |
| Butyrivibrio sp. AE2015_2 | |
| Butyrivibrio sp. AE3004_2 | |
| Butyrivibrio sp. AE3006_2 | |
| Butyrivibrio sp. FC2001_2 | |
| Butyrivibrio sp. INlla14 | |
| Butyrivibrio sp. INlla16 | |
| Butyrivibrio sp. INlla18 | |
| Butyrivibrio sp. LC3010 | |
| Butyrivibrio sp. MB2005 | |
| Butyrivibrio sp. MC2021_2 | |
| Butyrivibrio sp. NC2002 | |
| Butyrivibrio sp. NC2007 | |
| Butyrivibrio sp. OB235 | |
| Butyrivibrio sp. Su6 | |
| Butyrivibrio sp. TB | |
| Butyrivibrio sp. VCB2001 | |
| Butyrivibrio sp. VCB2006 | |
| Butyrivibrio sp. WCD2001_2 | |
| Butyrivibrio sp. WCE2006 | |
| Butyrivibrio sp. XBB1001_2 | |
| Butyrivibrio sp. XPD2002_2 | |
| Butyrivibrio sp. XPD2006_2 | |
| Butyrivibrio sp. YAB3001 | |
| Clostridium aminophilum F | |
| Clostridiales bacterium NK3B98 | |
| Clostridiales bacterium WTE2008 | |
| Clostridium polysaccharolyticum DSM1801 | |
| Enterobacter sp. KPR-6 | |
| Erysipelotrichaceae bacterium NK3D112 | |
| Eubacterium ruminatium HUN269 | |
| Lachnospiraceae bacterium AC2014_2 | |
| Lachnospiraceae bacterium AC2028_2 | |
| Lachnospiraceae bacterium AC2029_2 | |
| Lachnospiraceae bacterium AD3010 | |
| Lachnospiraceae bacterium C6A11 | |
| Lachnospiraceae bacterium G41 | |
| Lachnospiraceae bacterium KH1P17 | |
| Lachnospiraceae bacterium MA2020_2 | |
| Lachnospiraceae bacterium MC2017_2 | |
| Lachnospiraceae bacterium MD2004 | |
| Lachnospiraceae bacterium NK4A144 | |
| Lachnospiraceae bacterium P6A3 | |
| Lachnospiraceae bacterium XBB2008 | |
| Lachnospiraceae bacterium XBD2001 | |

TABLE 5-continued

| Sequence_id | SEQ ID NO: |
|---|---|
| Methanobrevibacter olleyae DSM 16632 | |
| Oribacterium sp. FC2011 | |
| Oribacterium sp. P6A1 | |
| Prevotella sp. FD3004 | |
| Prevotella sp. KHP7 | |
| Propionibacterium sp. MB3007 | |
| Pseudobutyrivibrio sp. ACV-2 | |
| Pseudobutyrivibrio sp. MD2005 | |
| Pseudobutyrivibrio sp. OR37 | |
| Pseudobutyrivibrio sp. UC1225 | |
| Pseudobutyrivibrio xylanivorans DSM 10317 | |
| Ruminococcaceae bacterium AE2021 | |
| Ruminococcaceae bacterium D5 | |
| Ruminococcaceae bacterium KHP2 | |
| Ruminococcus sp. NK3A76 | |
| Ruminococcus sp. YE71 | |
| Sarcina sp. DSM 11001 | |
| Streptococcus bovis 2B | |
| Streptococcus bovis AG46_2 | |
| Streptococcus bovis SN033 | |
| Streptococcus equinus GA-1 | |
| Streptococcus equinus pGA-7 | |
| Streptococcus equinus pR5 | |

CONCLUSION

The analyses of multiple animals feeding on the exact same diet and kept under the same conditions showed that there are large variations in the individual animals' ability to extract energy from their feed. These variations are tightly linked to several microbiome features that include a decrease in richness and increase in dominance of taxonomic and coding capacity in the efficient cow's microbiome. They are reflected as changes in this ecosystem's functionality, where changes in the dominance of specific functional components affect the overall availability of ecosystem goods that are of high value to the hosting animal. Higher microbiome richness and changes in specific functional groups have been recently described to affect host productivity in plants (Wagg et al., 2014) as well as humans, where lower diversity and richness has been associated with higher energy harvesting from feed in obese humans (Turnbaugh et al., 2009, Le Chatelier et al., 2013). A possible explanation for this phenomenon could stem from a more diverse use of resource compounds in the inefficient cow's microbiomes that are enriched in species, genes and KEGG pathways resulting in a wider array of output metabolites (FIGS. 3, 6A-B and 7A-B); this was also confirmed by significantly higher KEGG output metabolites. On the other hand, in the efficient cow's microbiome, simpler metabolic pathway networks result in increased dominance of specific functional components, which leads to higher concentrations of ecosystem goods that are relevant to the host (FIG. 7B). Therefore, the efficient microbiomes are less complex but more specialized to support the host's energy requirements.

This notion is exemplified by the finding of higher concentrations of SCFAs which are valuable to the hosting animal, SCFAs are absorbed through the rumen wall to serve the energetic needs of the animals; propionate, for example, is the main precursor for gluconeogenesis in animals (Russell & Wilson, 1996, Mizrahi, 2011, Mizrahi, 2013). This is not the case with methane as the energy retained in it cannot be absorbed by the animals, and is lost to the atmosphere. Such metabolic changes are usually achieved via the use of antibiotic growth promoters that increase the animal's feed-efficiency (Duffield et al., 2012). Such is the case with monensin, a carboxylic polyether ionophore that selectively affects some of the rumen microbes, therefore changing the structure of the rumen microbiome and subsequently the ratio of SCFAs in the rumen, increasing propionic acid and decreasing methane production (Thornton & Owens, 1981, Callaway et al., 2003, Weimer et al., 2008, Duffield et al., 2012). It has been shown that when administered orally, monensin improves feed-efficiency in cattle in a dose dependent manner. Therefore it has been used for this purpose extensively since its approval for cattle agriculture in the mid-1970s (Duffield et al., 2012). This effect of rumen microbiome manipulation achieved via antibiotics further supports the connection of the rumen microbiome with the feed-efficiency of the animal.

Here we show that these metabolomic changes are the outcome of microbiome structures that are naturally occurring and are highly correlated with, and predictive of the feed-efficiency phenotype. Therefore, these findings could be harnessed to reduce the use of antibiotic growth promoters in agriculture.

From an ecological perspective, the lower abundance of methanogenesis pathways and methanogenic archaea in the efficient cow's low-richness microbiome concurs with the notion that processes that are performed by small taxonomic groups, such as the methanogenic archaea that occupy only small percentages of the rumen microbiome, are more sensitive to changes in diversity and richness (Hooper et al., 1995). These changes are usually accompanied by occupation and dominance of the available niche by different species using the same resources (Grime, 1998). Such is the case with *M. elsdenii* and *C. catus*, independently found to be enriched in the efficient animals' microbiomes in different analyses (FIGS. 5A-B, 6A and 20), which use electrons for the production of the valuable SCFAs propionate and butyrate, thereby diverting them from reducing $CO_2$ to methane (Prabhu et al., 2012, Ungerfeld, 2015). A similar principle was shown to apply in Tammar wallabies, where *Succinivibrio* bacteria were suggested to utilize hydrogen for the production of succinate, therefore lowering its availability for methanogenesis (Pope et al., 2011). It is also possible that the Lachnospiraceae detected in the efficient animals' microbiomes are butyrate-producers (FIGS. 5A-B) and are contributing further to this effect (Louis & Flint, 2009, Meehan & Beiko, 2014). Nevertheless, as other SCFAs are enriched in this microbiome group and most of the carbon flux in the system goes to acetyl CoA, formate or hydrogen and carbon dioxide, it is likely that more genes and pathways are involved in this effect.

A cardinal point that emerges from the findings is that the functional characteristics of a small number of species can have a large impact on community structure and ecosystem functioning. This, in turn, can change the productivity of the supraorganism—the host and its residing rumen microbiome.

These findings could potentially be harnessed to increase the production of food resources for mankind in a more sustainable manner, as well as to understand the underlying ecological mechanisms that govern complex microbial communities and their interactions with their hosts.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Aha D W. (1997). Lazy learning. Springer Science & Business Media.

Ajmone-Marsan P, Garcia J F, Lenstra J A. (2010). On the origin of cattle: How aurochs became cattle and colonized the world. Evol Anthropol Issues News Rev, 19, 148-157.

Archer J A, Richardson E C, Herd R M, Arthur P F. (1999). Potential for selection to improve efficiency of feed use in beef cattle. Aust J Agric Res 50, 147-162.

Benjamini Y, Hochberg Y. (1995). Controlling the false discovery rate: a practical and powerful approach to multiple testing. J R Stat Soc Series B (Methodological), 289-300.

Bradford G E. (1999). Contributions of animal agriculture to meeting global human food demand. Livest Prod Sci, 59, 95-112.

Brulc J M, Antonopoulos D A, Miller M E, Wilson M K, Yannarell A C, Dinsdale E A, et al. (2009). Gene-centric metagenomics of the fiber-adherent bovine rumen microbiome reveals forage specific glycoside hydrolases. Proc Natl Acad Sci USA, 106, 1948-53.

Callaway T R, Edrington T S, Rychlik J L, Genovese K J, Poole T L, Jung Y S, et al. (2003). Ionophores: their use as ruminant growth promotants and impact on food safety. Curr Issues Intest Microbiol, 4, 43-51.

Caporaso J G, Kuczynski J, Stombaugh J, Bittinger K, Bushman F D, Costello E K, et al. (2010). QIIME allows analysis of high-throughput community sequencing data. Nature Methods, 7, 335-336.

Cole J R, Chai B, Marsh T L, Farris R J, Wang Q, Kulam S A, et al. (2003). The Ribosomal Database Project (RDP-II): previewing a new autoaligner that allows regular updates and the new prokaryotic taxonomy. Nucleic Acids Res, 31, 442-443.

Conesa A, Götz S, Garcia-Gómez J M, Terol J, Talon M, Robles M. (2005). Blast2GO: a universal tool for annotation, visualization and analysis in functional genomics research. Bioinformatics, 21, 3674-3676.

Gene Ontology Consortium. (2004). The Gene Ontology (GO) database and informatics resource. Nucleic Acids Res, 32, D258-D261.

Davis J C. (1986). Statistics and data analysis in geology. Wiley.

Duffield T F, Merrill J K, Bagg R N. (2012). Meta-analysis of the effects of monensin in beef cattle on feed efficiency, body weight gain, and dry matter intake. J Anim Sci, 90, 4583-92.

Duncan S H, Louis P, Thomson J M, Flint H J. (2009). The role of pH in determining the species composition of the human colonic microbiota. Environ Microbiol, 11, 2112-2122.

Edgar R C. (2010). Search and clustering orders of magnitude faster than BLAST. Bioinformatics, 26, 2460-2461.

Grime J. (1998). Benefits of plant diversity to ecosystems: immediate, filter and founder effects. J Ecol, 86, 902-910.

Halachmi I, Edan Y, Maltz E, Peiper U, Moallem U, Brukental I. (1998). A real-time control system for individual dairy cow food intake. Comput Electron Agr, 20, 131-144.

Harper D. (1999). Numerical palaeobiology. Wiley.

Henderson G, Cox F, Ganesh S, Jonker A, Young W, Collaborators G R C, et al. (2015). Rumen microbial community composition varies with diet and host, but a core microbiome is found across a wide geographical range. Scientific reports, 5.

Herd R M, Arthur P F. (2009). Physiological basis for residual feed intake. J Anim Sci, 87, E64-E71.

Hernandez-Sanabria E, Goonewardene L A, Wang Z, Durunna O N, Moore S S. (2012). Impact of feed efficiency and diet on adaptive variations in the bacterial community in the rumen fluid of cattle. Appl Environ Microb, 78, 1203-1214.

Hess M, Sczyrba A, Egan R, Kim T W, Chokhawala H, Schroth G, et al. (2011). Metagenomic discovery of biomass-degrading genes and genomes from cow rumen. Science, 331, 463-467.

Holdman L V, Moore W E C. (1974). New genus, *Coprococcus*, twelve new species, and emended descriptions of four previously described species of bacteria from human feces. Int J Syst Evol Micr, 24, 260-277.

Hooper D U, Hawksworth D, Dhillion S. (1995). Microbial diversity and ecosystem processes. Global biodiversity assessment. UNEP. Cambridge Univ. Press, Cambridge, pp 433-443.

Hooper D U, Chapin F S, Ewel J J, Hector A, Inchausti P, Lavorel S, et al. (2005). Effects of biodiversity on ecosystem functioning: a consensus of current knowledge. Ecol Monogr, 75, 3-35.

Jami E, Israel A, Kotser A, Mizrahi I. (2013). Exploring the bovine rumen bacterial community from birth to adulthood. ISME J, 7, 1069-1079.

Jami E, Mizrahi I. (2012). Composition and similarity of bovine rumen microbiota across individual animals. PLoS ONE, 7, e33306.

Jami E, White B A, Mizrahi I. (2014). Potential role of the bovine rumen microbiome in modulating milk composition and feed efficiency. PLoS ONE, 9, e85423.

Pollard K S, Dudoit S, van der Laan M J. (2005). Multiple Testing Procedures: the multtest Package and Applications to Genomics. In: Gentleman R, Carey V, Huber W, Irizarry R, Dudoit S (eds). Bioinformatics and Computational Biology Solutions Using R and Bioconductor. Springer New York, pp 249-271

Kanehisa M, Goto S, Sato Y, Furumichi M, Tanabe M. (2011). KEGG for integration and interpretation of large-scale molecular data sets. Nucleic Acids Res, gkr988.

Kittelmann S, Pinares-Patilio C S, Seedorf H, Kirk M R, Ganesh S, Mcewan J C, et al. (2014). Two different bacterial community types are linked with the low-methane emission trait in sheep. PLoS One, 9, e103171.

Koch R M, Swiger L A, Chambers D, Gregory K E. (1963). Efficiency of feed use in beef cattle. J Anim Sci, 22, 486-494.

Kultima J R, Sunagawa S, Li J, Chen W, Chen H, Mende D R, et al. (2012). MOCAT: a metagenomics assembly and gene prediction toolkit. PLoS One, 7, e47656.

Le Chatelier E, Nielsen T, Qin J, Prifti E, Hildebrand F, Falony G, et al. (2013). Richness of human gut microbiome correlates with metabolic markers. Nature, 500, 541-546.

Li D, Lewinger J P, Gauderman W J, Murcray C E, Conti D. (2011). Using extreme phenotype sampling to identify the rare causal variants of quantitative traits in association studies. Genet Epidemiol, 35, 790-9.

Li H, Durbin R. (2009). Fast and accurate short read alignment with Burrows-Wheeler transform. Bioinformatics, 25, 1754-1760.

Lippke H, Ellis W C, Jacobs B F. (1986). Recovery of indigestible fiber from feces of sheep and cattle on forage diets. J Dairy Sci, 69, 403-412.

Louis P, Flint H J. (2009). Diversity, metabolism and microbial ecology of butyrate-producing bacteria from the human large intestine. FEMS Microbiol Lett, 294, 1-8.

McDougall E. (1948). Studies on ruminant saliva. 1. The composition and output of sheep's saliva. Biochem J, 43, 99.

McMichael A J, Powles J W, Butler C D, Uauy R. (2007). Food, livestock production, energy, climate change, and health. The Lancet, 370, 1253-1263.

Meehan C J, Beiko R G. (2014). A Phylogenomic View of Ecological Specialization in the Lachnospiraceae, a Family of Digestive Tract-Associated Bacteria. Genome Biol Evol, 6, 703-713.

Meyer F, Paarmann D, D'souza M, Olson R, Glass E, Kubal M, et al. (2008). The metagenomics RAST server—a public resource for the automatic phylogenetic and functional analysis of metagenomes. BMC Bioinformatics, 9, 386.

Mizrahi I. (2011). The Role of the Rumen Microbiota in Determining the Feed Efficiency of Dairy Cows. In: Rosenberg E, Gophna U (eds). Beneficial Microorganisms in Multicellular Life Forms. Springer Science & Business Media, pp 203-210.

Mizrahi I. (2013). Rumen symbioses. In: Rosenberg E, DeLong F, Lory S, Stackebrandt E, Thompson F (eds). The Prokaryotes. Springer Science & Business Media, pp 533-544.

Moore S S, Mujibi F D, Sherman E L. (2009). Molecular basis for residual feed intake in beef cattle. J Anim Sci, 87, E41-7.

Nkrumah J D, Okine E K, Mathison G W, Schmid K, Li C, Basarab J A, et al. (2006). Relationships of feedlot feed efficiency, performance, and feeding behavior with metabolic rate, methane production, and energy partitioning in beef cattle. J Anim Sci, 84, 145-53.

Peterson J, Garges S, Giovanni M, Mcinnes P, Wang L, Schloss J A, et al. (2009). The NIH human microbiome project. Genome Res, 19, 2317-2323.

Pope P B, Smith W, Denman S E, Tringe S G, Barry K, Hugenholtz P, et al. (2011). Isolation of Succinivibrionaceae implicated in low methane emissions from Tammar wallabies. Science, 333, 646-8.

Prabhu R, Altman E, Eiteman M A. (2012). Lactate and acrylate metabolism by *Megasphaera elsdenii* under batch and steady-state conditions. Appl Environ Microbiol, 78, 8564-70.

Pruitt K D, Tatusova T, Maglott D R. (2007). NCBI reference sequences (RefSeq): a curated non-redundant sequence database of genomes, transcripts and proteins. Nucleic Acids Res, 35, D61-D65.

Pryce J, Arias J, Bowman P, Davis S, Macdonald K, Waghorn G, et al. (2012). Accuracy of genomic predictions of residual feed intake and 250-day body weight in growing heifers using 625,000 single nucleotide polymorphism markers. J Dairy Sci, 95, 2108-2119.

Reichardt N, Duncan S H, Young P, Belenguer A, Mcwilliam Leitch C, Scott K P, et al. (2014). Phylogenetic distribution of three pathways for propionate production within the human gut microbiota. ISME J, 8, 1323-35.

Rho M, Tang H, Ye Y. (2010). FragGeneScan: predicting genes in short and error-prone reads. Nucleic Acids Res.

Russell J B. (1998). The Importance of pH in the Regulation of Ruminal Acetate to Propionate Ratio and Methane Production In Vitro. J Dairy Sci, 81, 3222-3230.

Russell J B, Rychlik J L. (2001). Factors that alter rumen microbial ecology. Science, 292, 1119-1122.

Russell J B, Wilson D B. (1996). Why are ruminal cellulolytic bacteria unable to digest cellulose at low pH? J Dairy Sci, 79, 1503-1509.

Saleem F, Bouatra S, Guo A C, Psychogios N, Mandal R, Dunn S M, et al. (2013). The bovine ruminal fluid metabolome. Metabolomics, 9, 360-378.

Seymour W M, Campbell D R, Johnson Z B. (2005). Relationships between rumen volatile fatty acid concentrations and milk production in dairy cows: a literature study. Anim Feed Sci Tech, 119, 155-169.

Shi W, Moon C D, Leahy S C, Kang D, Froula J, Kittelmann S, et al. (2014). Methane yield phenotypes linked to differential gene expression in the sheep rumen microbiome. Genome Res, 24, 1517-1525.

Stevenson D M, Weimer P J. (2007). Dominance of *Prevotella* and low abundance of classical ruminal bacterial species in the bovine rumen revealed by relative quantification real-time PCR. Appl Microbiol Biotechnol, 75, 165-74.

Thornton J H, Owens F N. (1981). Monensin supplementation and in vivo methane production by steers. J Anim Sci, 52, 628-34.

Thornton P K. (2010). Livestock production: recent trends, future prospects. Philos Trans R Soc Lond B Biol Sci, 365, 2853-67.

Tilley J, Terry R. (1963). A two-stage technique for the in vitro digestion of forage crops. Grass Forage Sci, 18, 104-111.

Turnbaugh P J, Hamady M, Yatsunenko T, Cantarel B L, Duncan A, Ley R E, et al. (2009). A core gut microbiome in obese and lean twins. Nature, 457, 480-484.

Ungerfeld E M. (2015). Shifts in metabolic hydrogen sinks in the methanogenesis-inhibited ruminal fermentation: a meta-analysis. Front Microbiol, 6, 37.

van Soest P J, Robertson J B, Lewis B A. (1991). Methods for dietary fiber, neutral detergent fiber, and nonstarch polysaccharides in relation to animal nutrition. J Dairy Sci, 74, 3583-97.

Wagg C, Bender S F, Widmer F, van der Heijden M G. (2014). Soil biodiversity and soil community composition determine ecosystem multifunctionality. Proc Natl Acad Sci USA, 111, 5266-70.

Wallace R J, Rooke J A, Mckain N, Duthie C A, Hyslop J J, Ross D W, et al. (2015). The rumen microbial metagenome associated with high methane production in cattle. BMC Genomics, 16, 1.

Weimer P J, Stevenson D M, Mertens D R, Thomas E E. (2008). Effect of monensin feeding and withdrawal on populations of individual bacterial species in the rumen of lactating dairy cows fed high-starch rations. Appl Microbiol Biotechnol, 80, 135-45.

Westfall P H, Young S S. (1993). Resampling-based multiple testing: Examples and methods for p-value adjustment, John Wiley & Sons.

---

What is claimed is:

1. A method of increasing the feed efficiency or decreasing the methane production of a ruminating animal comprising administering to the animal a bacterial composition which comprises the bacteria of the bacterial genus *Megasphaera* and of the species *Coprococcus catus*, wherein the composition comprises between 2-30 microbial species, thereby increasing the feed efficiency or decreasing the methane production of a ruminating animal.

2. The method of claim 1, wherein the ruminating animal is younger than 6 months old.

3. The method of claim 1, wherein said agent is comprised in a feed.

4. The method of claim 1, wherein said agent is comprised in a silage.

5. The method of claim 1, wherein said agent is comprised in an enema.

6. The method of claim 1, wherein said animal is treated with an antibiotic composition prior to the administering.

7. The method of claim 1, wherein the bacterial composition further comprises bacteria of the species *Clostridium propionicum*.

* * * * *

SEQUENCE LISTING

```
<160> NUMBER OF SEQ ID NOS: 21

<210> SEQ ID NO 1
<211> LENGTH: 250
<212> TYPE: DNA
<213> ORGANISM: Unknown
<220> FEATURE:
<223> OTHER INFORMATION: Bacteroidales 16S ribosomal RNA   sequence

<400> SEQUENCE: 1
tgaggaatat tggtcaatgg acggaagtct gaaccagcca tgccgcgtgg aggaagaagg      60
tcctatgggt tgtaaactcc ttttgctccg gagtaataag agccttgcga ggcttgatga     120
gagtacgggg cgaataagca tcggctaact ccgtgccagc agccgcggta atacggagga     180
tgcgagcgtt atccggattt attgggttta aagggtgcgc aggcggcgcg ttaagtcagc     240
ggtgaaatgt                                                            250

<210> SEQ ID NO 2
<211> LENGTH: 250
<212> TYPE: DNA
<213> ORGANISM: Unknown
<220> FEATURE:
<223> OTHER INFORMATION: Clostridiales 16S ribosomal RNA   sequence

<400> SEQUENCE: 2
tcgggaatat tgcgcaatgg aggaaactct gacgcagtga cgccgcgtat aggaagaagg      60
tcttcggatt gtaaactatt gtcgttaggg aagagaaagg acagtaccta aggaggaagc     120
tccggctaac tacgtgccag cagccgcggt aatacgtagg gagcgagcgt tatccggatt     180
tattgggtgt aaagggtgcg tagacgggaa gttaagttag ttgtgaaatc cccaggctca     240
```

```
acttgggaac                                                             250

<210> SEQ ID NO 3
<211> LENGTH: 250
<212> TYPE: DNA
<213> ORGANISM: Unknown
<220> FEATURE:
<223> OTHER INFORMATION: Clostridiales 16S ribosomal RNA   sequence

<400> SEQUENCE: 3
tcgggaattt tgcgcaatgg aggaaactct gacgcagtga cgccgcgtat aggaagaagg      60
ttttcggatt gtaaactatt gtcgttaggg aagaaatttg acagtaccta aggaggaagc     120
tccggctaac tatgtgccag cagccgcggt aatacatagg gagcaagcgt tatccggatt    180
tattgggtgt aaagggtgcg tagacgggaa tacaagttgg ttgtgaaatc cctcggctta    240
actgaggaac                                                             250

<210> SEQ ID NO 4
<211> LENGTH: 250
<212> TYPE: DNA
<213> ORGANISM: Unknown
<220> FEATURE:
<223> OTHER INFORMATION: Clostridiales Megasphaera 16S ribosomal RNA
      sequence

<400> SEQUENCE: 4
tggggaatct tccgcaatgg acgaaagtct gacggagcaa cgccgcgtga acgatgacgg      60
ccttcgggtt gtaaagttct gttatacggg acgaatggta cgacggtcaa tacccgtcgt    120
aagtgacggt accgtaagag aaagccacgg ctaactacgt gccagcagcc gcggtaatac    180
gtaggtggca agcgttgtcc ggaattattg ggcgtaaagg cgcgcaggc ggcgtcgtaa     240 gtcggtctta                                                             250

<210> SEQ ID NO 5
<211> LENGTH: 250
<212> TYPE: DNA
<213> ORGANISM: Unknown
<220> FEATURE:
<223> OTHER INFORMATION: Lachnospiraceae 16S ribosomal RNA   sequence

<400> SEQUENCE: 5
tggggaatat tgcacaatgg ggggaaccct gatgcagcaa cgccgcgtga gtgaagaagt      60
atttcggtat gtaaagctct atcagcaggg aagagattga cggtacctga ctaagaagcc    120
ccggctaact acgtgccagc agccgcggta atacgtaggg ggcaagcgtt atccggattt    180
actgggtgta aagggagcgc agacggaagt gcaagtcaga agtgaaagcc gcggcccaa     240 ctgcgggact                                                             250

<210> SEQ ID NO 6
<211> LENGTH: 250
<212> TYPE: DNA
<213> ORGANISM: Unknown
<220> FEATURE:
<223> OTHER INFORMATION: Bacteroidales Prevotella 16S ribosomal RNA
      sequence

<400> SEQUENCE: 6
tgaggaatat tggtcaatgg acgagagtct gaaccagcca agtagcgtgc aggaagacgg      60
ccctatgggt tgtaaactgc ttttgcaggg gaataaagtg acgtacgtgt acgttttgt     120 atgtaccctg agaataagga ccggctaatt ccgtgccagc agccgcggta atacggaagg    180
```

```
tccgggcgtt atccggattt attgggttta aagggagcgc aggccggctg ttaagcgtga        240
cgtgaaatgc                                                               250

<210> SEQ ID NO 7
<211> LENGTH: 250
<212> TYPE: DNA
<213> ORGANISM: Unknown
<220> FEATURE:
<223> OTHER INFORMATION: Bacteroidales CF231 16S ribosomal RNA sequence

<400> SEQUENCE: 7
tgaggaatat tggtcaatgg tcgagagact gaaccagcca agtagcgtgc aggatgactg         60
ccctatgggt tgtaaactgc ttttgtttgg gaataaagtg ggtcacgcgt ggcttttttgt       120 atgtaccata cgaataagca tcggctaatt ccgtgccagc agccgcggta atacggaaga       180
tgcgagcgtt atccggattt attgggttta aagggagcgt aggcggcctg ttaagtcagc       240
ggttaaatgt                                                               250

<210> SEQ ID NO 8
<211> LENGTH: 250
<212> TYPE: DNA
<213> ORGANISM: Unknown
<220> FEATURE:
<223> OTHER INFORMATION: Bacteroidales Prevotella 16S ribosomal RNA
      sequence

<400> SEQUENCE: 8
tgaggaatat tggtcaatgg gcgcgagcct gaaccagcca agtagcgtga gggacgactg         60
ccctatgggt tgtaaacctc ttttgttcgg gaataacatg cgggacgtgt cccgtattgc       120
atgtaccgtt cgaataagga ccggctaatt ccgtgccagc agccgcggta atacggaagg       180
tccgggcgtt atccggattt attgggttta aagggagcgc aggcggtttt tcaagcgtga       240
cgtgaaatgc                                                               250

<210> SEQ ID NO 9
<211> LENGTH: 250
<212> TYPE: DNA
<213> ORGANISM: Unknown
<220> FEATURE:
<223> OTHER INFORMATION: Clostridiales Mogibacteriaceae16S ribosomal RNA
      sequence

<400> SEQUENCE: 9
tggggaatat tgcacaatgg agggaactct gatgcagcaa cgccgcgtga gtgaagaagg        60
tcttcggatt gtaaaactct gtccttggga aagaaattga tgacggtacc caagaagaaa      120
gccccggcta actacgtgcc agcagccgcg gtaatacgta gggggcgagc gttatccgga       180
attattgggc gtaaagagta cgtaggtggc cgtgtaagcg tgaggtgaag gcctggagct      240
taactccagt                                                              250

<210> SEQ ID NO 10
<211> LENGTH: 250
<212> TYPE: DNA
<213> ORGANISM: Unknown
<220> FEATURE:
<223> OTHER INFORMATION: Bacteroidales family S24-7 16S ribosomal RNA
      sequence

<400> SEQUENCE: 10
tgaggaatat tggtcaatgg gcgatagcct gaaccagcca agtcgcgtgc gggatgaagg        60
```

```
ccctatgggt cgtaaaccgc ttttgtcggg gagcaaagtg cgtcacgtgt ggcgtattgc        120
gagtacccga agaaaagca tcggctaact ccgtgccagc agccgcggta atacggagga         180
tgcgagcgtt atccggattt attgggttta aagggtgcgc aggcggcgtg tcaatcagcg        240
gttaaaatgc                                                               250

<210> SEQ ID NO 11
<211> LENGTH: 250
<212> TYPE: DNA
<213> ORGANISM: Unknown
<220> FEATURE:
<223> OTHER INFORMATION: Bacteroidales 16S ribosomal RNA   sequence

<400> SEQUENCE: 11
tgaggaatat tggtcaatgg gcggaagcct gaaccagcca agtcgcgtga aggatgaagg         60
cattatgtgt tgtaaacttc tttagctgtg gagaaataag gtggtcgaga ccaccgatgc        120
tagtacacag agaataagga tcggctaact ccgtgccagc agccgcggta atacggagga        180
tccgagcgtt atccggattc attgggttta aagggtgcgc aggcggtgcc ttaagtcagc        240
ggtaaaatcg                                                               250

<210> SEQ ID NO 12
<211> LENGTH: 250
<212> TYPE: DNA
<213> ORGANISM: Unknown
<220> FEATURE:
<223> OTHER INFORMATION: Lachnospiraceae 16S ribosomal RNA   sequence

<400> SEQUENCE: 12
tggggaatat tgcacaatgg gcgcaagcct gatgcagcga cgccgcgtga aggacgaagt         60
atttcggtat gtaaacttct atcagcgggg aagaagatga cggtacccga ctaagaagcc        120
ccggctaact acgtgccagc agccgcggta atacgtaggg ggcaagcgtt atccggattt        180
actgggtgta aagggagcgt agccggtgag gcaagtccga tgtgaaaacc cgtggctcac        240
ccccgggatt                                                               250

<210> SEQ ID NO 13
<211> LENGTH: 250
<212> TYPE: DNA
<213> ORGANISM: Unknown
<220> FEATURE:
<223> OTHER INFORMATION: Clostridiales 16S ribosomal RNA   sequence

<400> SEQUENCE: 13
tggggaatat tgtacaatgg aggaaactct gatgcagcga cgccgcgtga gtgaagaagg         60
atttcggtat gtaaagctct atcagcagga aagaaaatga cggtacctga ctaagaagcc        120
ccggctaact acgtgccagc agccgcggca atacgtaggg ggcaagcgtt atccggattt        180
actgggtgta aggggagcgt agacggccat gcaagtctga agtgaaagct cggggctcaa        240
ccccggaact                                                               250

<210> SEQ ID NO 14
<211> LENGTH: 250
<212> TYPE: DNA
<213> ORGANISM: Unknown
<220> FEATURE:
<223> OTHER INFORMATION: Bacteroidales 16S ribosomal RNA   sequence

<400> SEQUENCE: 14
```

-continued

```
tgaggaatat tggtcaatgg agggaactct gaaccagcca tgccgcgtgg aggaagaagg    60
tcctatgggt tgtaaactcc ttttgttccg gagtaataag tgccttgcga ggcacgatga   120
gagtacggga cgaataagca tcggctaact ccgtgccagc agccgcggta atacggagga   180
tgcaagcgtt atccggattt attgggttta aagggtgcgc aggcggactg ttaagtcagc   240
ggtgaaatgt                                                          250
```

<210> SEQ ID NO 15
<211> LENGTH: 250
<212> TYPE: DNA
<213> ORGANISM: Unknown
<220> FEATURE:
<223> OTHER INFORMATION: Clostridiales Ruminococcaceae 16S ribosomal RNA
      sequence <400> SEQUENCE: 15

```
tgagggatat tgcacaatgg gcgaaagcct gatgcagcaa cgccgcgtga gggatgacgg    60
ttttcggatt gtaaacctct gtcttcggtg aagataatga cattagccga ggaggaagcc   120
acggctaact acgtgccagc agccgcggta atacgtaggt ggcaagcgtt gtccggattt   180
actgggtgta aagggagcgc aggcgggaca gcaagtcagc ggtgaaatgc atgggcttaa   240
cccatgaact                                                          250
```

<210> SEQ ID NO 16
<211> LENGTH: 250
<212> TYPE: DNA
<213> ORGANISM: Unknown
<220> FEATURE:
<223> OTHER INFORMATION: Clostridiales 16S ribosomal RNA  sequence
<400> SEQUENCE: 16

```
tggggaatat tgggcaatgg gcgaaagcct gacccagcaa cgccgcgtga gggaagaagg    60
gtttcggctc gtaaacctct gtccttaggg acgaagaagg gacggtactt taggaggaag   120
ccccggctaa ctacgtgcca gcagccgcgg taatacgtag ggggcgagcg ttgtccggaa   180
tgattgggcg gaaagggcgg gtaggggcc cgttaagtct ggagtgaaag tcctgctttc    240
aaggtgggaa                                                          250
```

<210> SEQ ID NO 17
<211> LENGTH: 250
<212> TYPE: DNA
<213> ORGANISM: Unknown
<220> FEATURE:
<223> OTHER INFORMATION: Clostridiales 16S ribosomal RNA  sequence
<400> SEQUENCE: 17

```
tcgggaatat tgcgcaatgg aggaaactct gacgcagtga cgccgcgtat aggatgaagg    60
ttttcggatt gtaaactatt gtcgttaggg aagaaatttg acagtaccta aggaggaagc   120
tccggctaac tatgtgccag cagccgcggt aatacatagg gagcaagcgt tatccggatt   180
tattgggtgt aaagggtgcg tagacggaga agcaagttag ttgtgaaagc cctcggctta   240
actgaggaac                                                          250
```

<210> SEQ ID NO 18
<211> LENGTH: 250
<212> TYPE: DNA
<213> ORGANISM: Unknown
<220> FEATURE:
<223> OTHER INFORMATION: Bacteroidales Prevotella 16S ribosomal RNA
      sequence

```
<400> SEQUENCE: 18
tgaggaatat tggtcaatgg gcggaagcct gaaccagcca agtagcgtgt gggatgacgg      60
ccctacgggt tgtaaaccac ttttgcgcgg ggataaccgg cggcacgcgt gccgccctgc     120
aggtaccgcg cgaataagga ccggctaatt ccgtgccagc agccgcggta atacggaagg    180
tccgggcgtt atccggattt attgggttta aagggagcgt aggcgggatg ctaagcgtgc    240
tgtgaaatcc                                                            250

<210> SEQ ID NO 19
<211> LENGTH: 250
<212> TYPE: DNA
<213> ORGANISM: Unknown
<220> FEATURE:
<223> OTHER INFORMATION: Clostridiales 16S ribosomal RNA  sequence

<400> SEQUENCE: 19
tcgggaatat tgcgcaatgg aggaaactct gacgcagtga cgccgcgtat aggaagaagg     60
ttttcggatt gtaaactatt gtcgtagggg aagataaaag acagtaccct aggaggaagc    120
tccggctaac tacgtgccag cagccgcggt aatacgtagg gagcaagcgt tatccggatt    180
tattgggtgt aaagggtgcg tagacgggag agcaagttag ttgtgaaatc cctcggctta   240
actgaggaac                                                            250

<210> SEQ ID NO 20
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 20
cctacgggag gcagcag                                                    17

<210> SEQ ID NO 21
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 21
ccgtcaattc mtttragt                                                   18
```